US009783599B2

(12) United States Patent
Vollmers et al.

(10) Patent No.: US 9,783,599 B2
(45) Date of Patent: Oct. 10, 2017

(54) LM-ANTIBODIES, FUNCTIONAL FRAGMENTS, LM-1 TARGET ANTIGEN, AND METHODS FOR MAKING AND USING SAME

(71) Applicant: Patrys Limited, Melbourne, Victoria (AU)

(72) Inventors: Heinz Peter Vollmers, Wurzburg (DE); Stephanie Ute Brandlein, Zellingen (DE); Andreas Thalheimer, Wurzburg (DE); Leodevico L. Ilag, Balwyn (AU); Barbara E. Power, Blackburn (AU); Lishanthi Udabage, Rowville (AU); Frank Hensel, Wurzburg (DE); Frank Schoenen, Wurzburg (DE); Arndt-Rene Kelter, Alfter (DE); Christopher Garth Hosking, Nunawading (AU)

(73) Assignee: Patrys Limited, Melbourne (AU)

( * ) Notice: Subject to any disclaimer, the term of this patent is extended or adjusted under 35 U.S.C. 154(b) by 0 days.

(21) Appl. No.: 14/211,283

(22) Filed: Mar. 14, 2014

(65) Prior Publication Data

US 2015/0071931 A1    Mar. 12, 2015

Related U.S. Application Data

(62) Division of application No. 12/484,476, filed on Jun. 15, 2009, now abandoned.

(60) Provisional application No. 61/143,351, filed on Jan. 8, 2009, provisional application No. 61/061,881, filed on Jun. 16, 2008.

(51) Int. Cl.
| | |
|---|---|
| *A61K 39/00* | (2006.01) |
| *A61K 39/395* | (2006.01) |
| *C07K 16/28* | (2006.01) |
| *C07K 16/18* | (2006.01) |
| *A61K 41/00* | (2006.01) |
| *A61K 51/10* | (2006.01) |
| *C07K 14/47* | (2006.01) |
| *C07K 16/30* | (2006.01) |
| *C12N 15/113* | (2010.01) |
| *G01N 33/574* | (2006.01) |

(52) U.S. Cl.
CPC .......... *C07K 16/18* (2013.01); *A61K 41/0095* (2013.01); *A61K 51/1045* (2013.01); *C07K 14/47* (2013.01); *C07K 16/30* (2013.01); *C07K 16/3023* (2013.01); *C12N 15/113* (2013.01); *G01N 33/574* (2013.01); *A61K 2039/505* (2013.01); *C07K 2317/52* (2013.01); *C07K 2317/73* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 6,159,702 | A | 12/2000 | Traish |
| 7,138,501 | B2 | 11/2006 | Ruben et al. |
| 7,947,812 | B2 | 5/2011 | Mueller-Hermelink et al. |
| 8,562,995 | B2 | 10/2013 | Mueller-Hermelink et al. |
| 2004/0081027 | A1 | 9/2004 | Mueller-Hermelink et al. |
| 2006/0263366 | A1* | 11/2006 | Mueller-Hermelink ......... C07K 16/3023 424/155.1 |
| 2009/0104100 | A1 | 8/2009 | Vollmers, et al. |
| 2011/0287021 | A1* | 11/2011 | Mueller-Hermelink ......... C07K 16/3023 424/155.1 |

OTHER PUBLICATIONS

Berglund et al, 2008, Protein Science, 17:606-613.*
Tzartos et al (Methods in Molecular Biology, 1996, 66:55-66).*
Padlan (Advances in Protein Chemistry, 1996, 49:57-133).*
Berglund (Berglund et al, 2008, Protein Science, 17:606-613, of record).*
Brandlein et al. (2005) "The natural human monoclonal IgM antibody LM-1 inhibits human lung cancer growth in vitro and in vivo" Journal of Clinical Oncology 23(16S):7347 (Jun. 1 Supplement; Abstract).
Casset et al. (2003) "A peptide mimetic of an anti-C D4 monoclonal antibody by rational design" Biochemical and Biophysical Research Communications 307:198-205.
Chen et al. (1999) "Selection and analysis of an optimized anti-VEGF antibody: crystal structure of an affinity-matured fab in complex with antigen" Journal of Molecular Biology 293:865-881.
Lamminmaki et al. (2001) "Crystal structure of a recombinant anti-estradiol fab fragment in complex with 17B-Estradiol" Journal of Biological Chemistry 276:36687-36694.
Mac Callum et al. (1996) "Antibody-antigen interactions: contact analysis and binding site topography" Journal of Molecular Biology 262:732-745.
Padlan et al. (1989) "Structure of an antibody-antigen complex: crystal structure of the HyHEL-10 fab-lysozyme complex" Proceedings of the National Academy of Sciences 86:5938-5942.

(Continued)

*Primary Examiner* — Julie Wu
(74) *Attorney, Agent, or Firm* — Carol L. Francis; Bozicevic, Field & Francis LLP

(57) ABSTRACT

The invention provides LM-1 antibodies, functional fragments, modified and variant forms, nucleic acid and other compositions. The invention also provides antibodies, functional fragments, modified and variant forms that bind to LM-1 antigen (e.g., NONO/nmt55). Antibodies, functional fragments, modified and variant forms, nucleic acid and other compositions are useful in treatment and diagnostic methods. One method includes treating metastasis of a neoplasia, tumor or cancer in a subject in need of treatment by administering to the subject an amount of a LM-1 antibody, an antibody that binds to LM-1 antigen, or a functional fragment thereof, effective to treat metastasis of the neoplasia, tumor or cancer in the subject.

4 Claims, 19 Drawing Sheets

(56) References Cited

OTHER PUBLICATIONS

Pascalis et al. (2002) "Grafting of 'abbreviated' complementarity-determining regions containing specificity-determining residues essential for ligand contact to engineer a less immunogenic humanized monoclonal antibody" The Journal of Immunology 169:3076-3084.
Rudikoff et al. (1982) "Single amino acid substitution altering antigen-binding specificity" Proceedings of the National Academy of Science USA 79:1979.
Skolnick et al. (2000) "From genes to protein structure and function: novel applications of computational approaches in the genomic era" Trends in Biotechnology 18:34-39.
Vajdos et al. (2002) "Comprehensive functional maps of the antigen binding site of an anti-ErbB2 antibody obtained with shotgun scanning mutagenesis" Journal of Molecular Biology 320:415-428.
Wu et al. (1999) "Humanization of a murine monoclonal antibody by simultaneous optimization of framework and CDR residues" Journal of Molecular Biology 294:151-162.
Engstrom et al., NCCN Clinical Practice Guidelines in Oncology, Colon Cancer, V.1.2008, www.nccn.org, 60 pages.
Tempero et al., NCCN Clinical Practice Guidelines in Oncology, Pancreatic Adenocarcinoma, V.2.2006, www.nccn.org, 41 pages.
Talheimer, Andreas, et al., (2009) "The intraportal injection model: A practical animal model for hepatic metastases and tumor cell dissemination in human colon cancer", BMC Cancer, 9(29):1-7.

* cited by examiner

A

B

Figure 5 (con't)
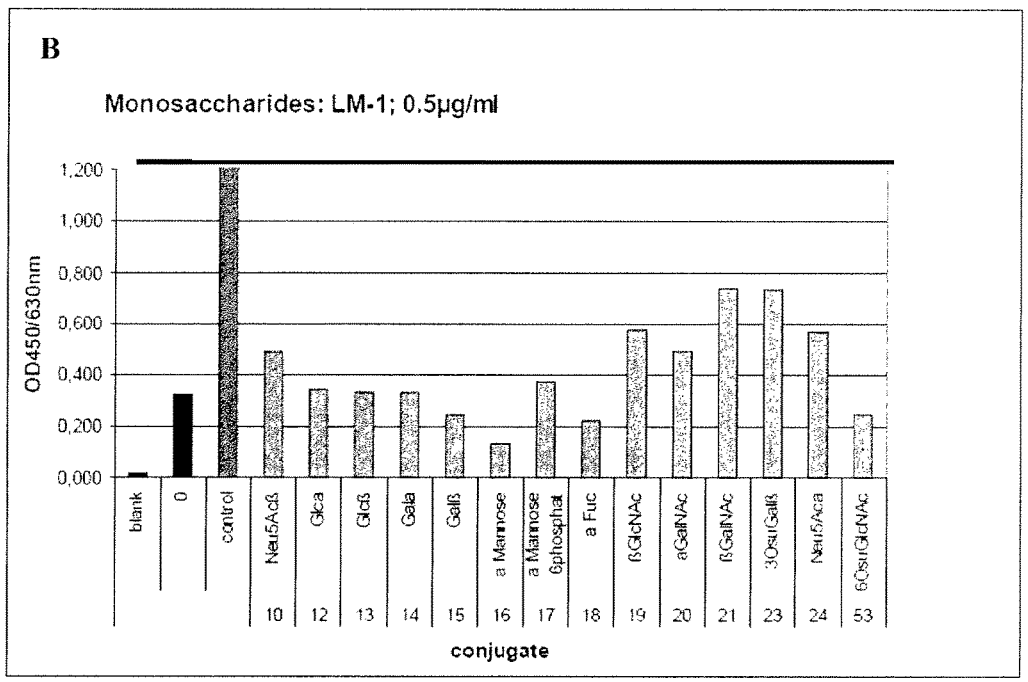
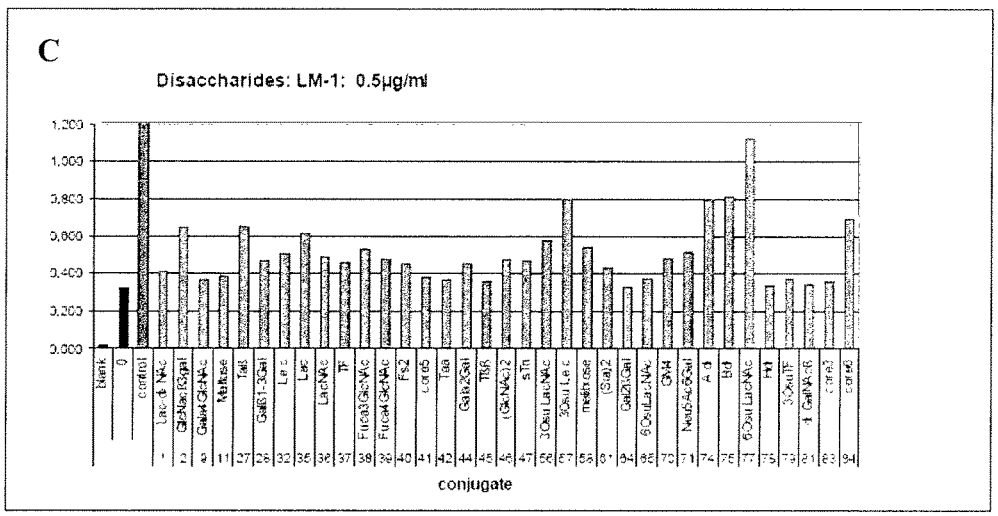

Figure 5 (con't)
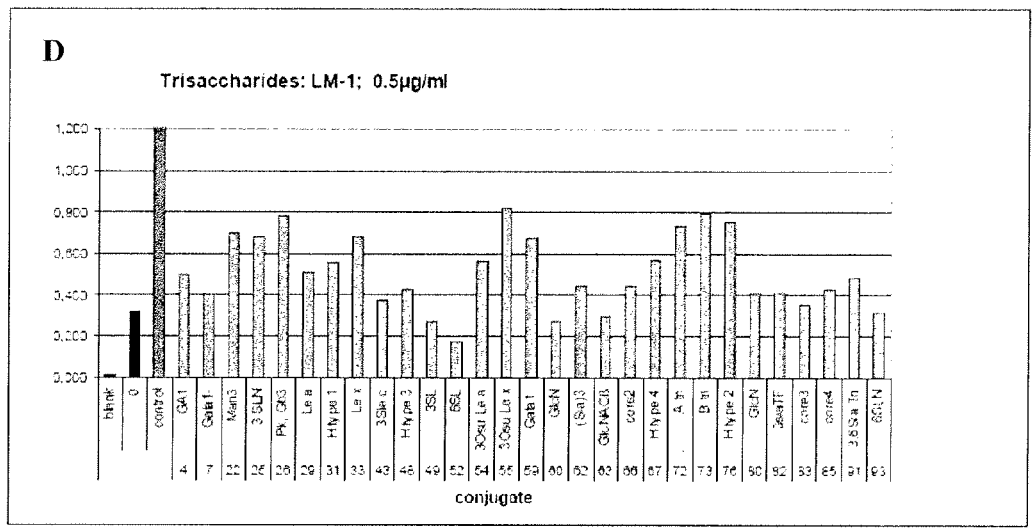
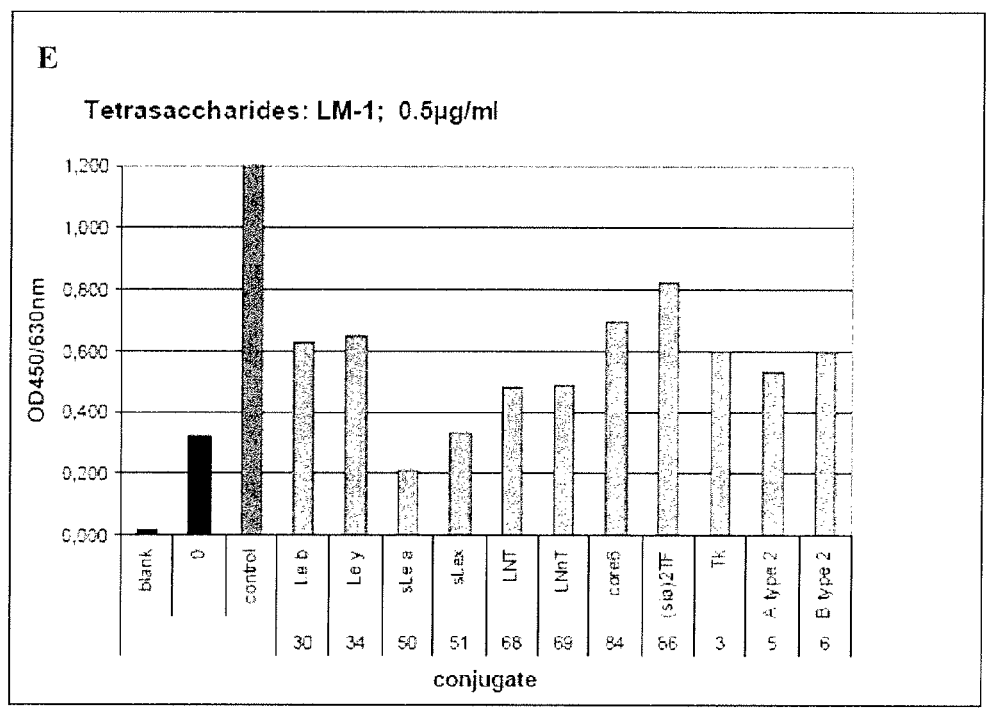

Figure 5 (con't)
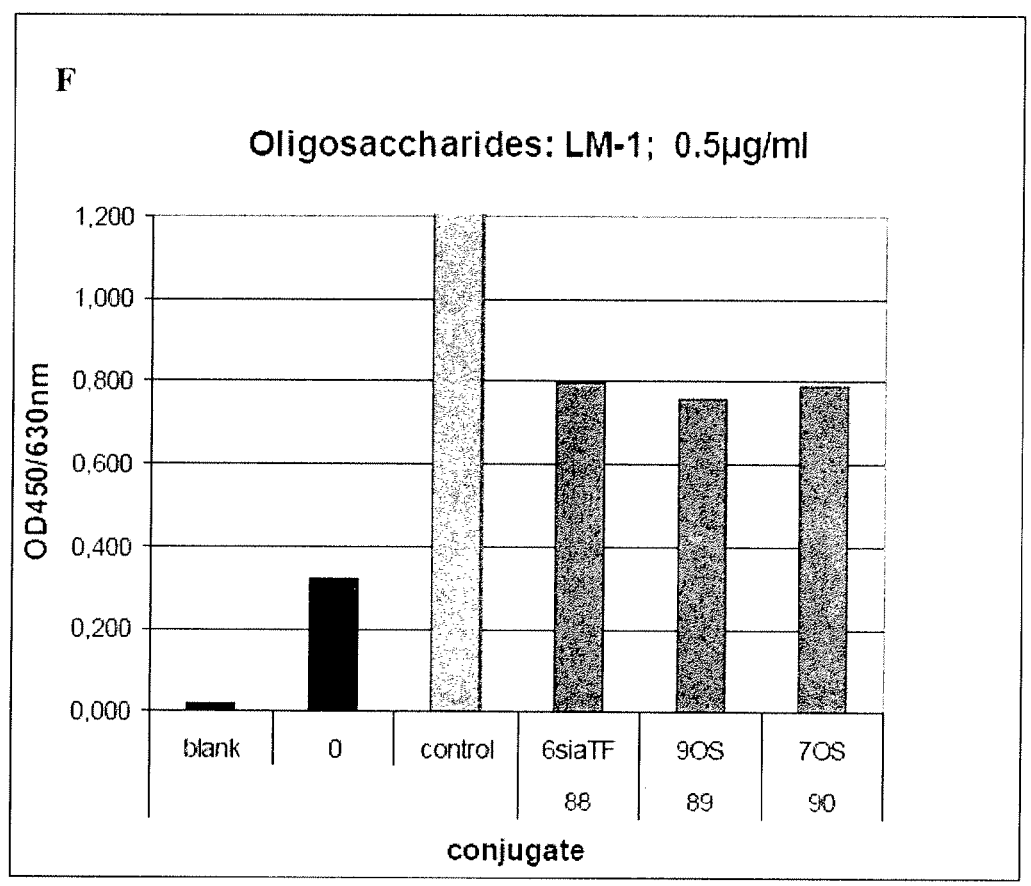

Silverstain-Gel

LM-1

LM-ANTIBODIES, FUNCTIONAL FRAGMENTS, LM-1 TARGET ANTIGEN, AND METHODS FOR MAKING AND USING SAME

RELATED APPLICATIONS

This application is a divisional of application Ser. No. 12/484,476, filed Jun. 15, 2009, which application claims the benefit of priority of application Ser. No. 61/143,351, filed Jan. 8, 2009, and application Ser. No. 61/061,881, filed Jun. 16, 2008, all of which applications are expressly incorporated herein by reference in their entirety.

FIELD OF THE INVENTION

The invention relates to an antibody, known as LM-1 and a target, known as LM-1 Target or Antigen. The antibody denoted LM-1 is an IgM and binds to different types of neoplasia, cancer, tumor and metastasis. LM-1 inhibits growth of various types of cancer cells and stimulates or induces apoptosis of various types of cancer cells. LM-1 also reduces formation or establishment of metastases at one or more sites arising from a primary neoplasia, tumor or cancer, or growth or proliferation of a metastasis that has formed or been established at one or more other sites.

INTRODUCTION

Metastatic disease at sites peripheral to the primary cancer potentially contribute to cancer progression and relapse. Consequently, inhibition of establishment or formation of metastasis, or reduction or decrease of metastasis growth, proliferation of or progression metastatic tumors that have been established is likely to reduce or inhibit cancer progression and relapse. The invention addresses this need and provides related benefits.

SUMMARY

The invention provides isolated and purified antibodies and functional fragments that compete for binding to a cell or to an antigen that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds. In one embodiment, an antibody or functional fragment competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, for binding to an neoplastic, tumor or cancer or a metastatic cell. In another embodiment, an antibody or functional fragment thereof competes for binding of LM-1 to NONO/nmt55 protein.

In particular aspects, an antibody or functional fragment competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, for binding to an antigen (e.g., NONO/nmt55 protein) on one or more of a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphomas, and leukemias. Such polypeptides are particularly useful for the detection and treatment of stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphomas, and leukemias.

In another embodiment, an antibody or functional fragment competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, for binding to a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia. In an additional embodiment, an antibody or functional fragment competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, for binding to one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), lung squamous cell carcinoma cell line LOU-NH91 (DSMZ accession number ACC 393), HT-29 (ATCC Accession No. HTB-38; DSMZ Accession No. ACC 299), A549 (DSMZ Accession No. ACC 107) or BXPC-3 (ATCC Accession No. CRL-1687) cells. In a further embodiment, an antibody or functional fragment thereof inhibits or reduces proliferation, or stimulates or induces apoptosis, of one or more of a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia, or one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

The invention also provides isolated and purified antibodies and functional fragments thereof that bind to cells or to an antigen (e.g., NONO/nmt55 protein) that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds. In one embodiment, an antibody or functional fragment binds to an adenocarcinoma cell or a squamous cell carcinoma to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds. In particular aspects, an antibody or functional fragment binds to one or more of stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia, to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds. In another embodiment, an antibody or functional fragment binds to a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds. In an additional embodiment, an antibody or functional fragment binds to one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, binds.

The invention further provides isolated and purified antibodies and functional fragments that include a heavy or light chain variable region sequence with about 60% or more identity to a heavy or light chain sequence variable regions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In one embodiment, an antibody or subsequence thereof includes a sequence at least 60% or more (e.g., 65%, 70%, 75%, 80%, 85%, 90%, 95%, etc.) identical to a heavy chain variable region sequence set forth as SEQ ID NO:1, 3, 5, 7 or 9, or heavy chain of antibody produced by a cell line DSMZ Deposit No. DSM ACC 262, or a sequence at least 60% or more (e.g., 65%, 70%, 75%, 80%, 85%, 90%, 95%, etc.) identical to a light chain variable region sequence set forth as SEQ ID NO:9 or light chain of antibody produced by a cell line DSMZ Deposit No. DSM ACC 262. In another embodiment, an antibody or subsequence includes a sequence at least 60% or more (e.g., 65%, 70%, 75%, 80%, 85%, 90%, 95%, etc.) identical to a heavy chain variable region sequence set forth as SEQ ID NO:1, 3, 5, 7 or 9, or heavy chain of antibody produced by a cell line DSMZ Deposit No. DSM ACC 262, and a sequence at least 60% or more (e.g., 65%, 70%, 75%, 80%, 85%, 90%, 95%, etc.) identical to a light chain variable region sequence set forth as SEQ ID NO:9 or light chain of antibody produced by a cell line DSMZ Deposit No. DSM ACC 262. In a further embodiment, an antibody or subsequence includes a sequence at least 80-85%, 85-90%, 90-95%, or 95-100% identical to one or more CDRs in heavy chain variable region sequence set forth as SEQ ID NO:1, 3, 5, 7 or 9 (e.g., amino acids 24-35, 52-67, or 100-118), or one or more CDRs in a heavy chain variable region of antibody produced by a cell line DSMZ Deposit No. DSM ACC 262, or a sequence at least 80-85%, 85-90%, 90-95%, or 95-100% identical to one or more CDRs in a light chain variable region sequence set forth as SEQ ID NO:9 (e.g., amino acids 23-35, 51-58 or 90-101 of SEQ ID NO:11 or 13), or one or more CDRs in a light chain variable region of antibody produced by a cell line DSMZ Deposit No. DSM ACC 262.

The invention further provides isolated and purified antibodies and functional fragments thereof that have one or more amino acid additions, deletions or substitutions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In particular aspects, an antibody or functional fragment has sequence at least 80-85%, 85-90%, 90-95%, or 95-100% identical to a heavy chain variable region sequence set forth as SEQ ID NO:1, 3, 5, 7 or 9, and 11 or 13, or a sequence at least 80-85%, 85-90%, 90-95%, or 95-100% identical to a light chain variable region sequence set forth as SEQ ID NO:9. In further aspects, an antibody or functional fragment has a heavy or light chain sequence with 100% identity to one or more CDRs in a heavy or light chain variable region sequence set forth as SEQ ID NOs:1, 3, 5, 7 or 9, and 11 or 13 (e.g., amino acids 24-35, 52-67, 100-118 of SEQ ID NO:1, 3, 5 or 7, or amino acids 23-35, 51-58, 90-101, of SEQ ID NO:11), and has less than 100% identity to a region outside of the CDRs in a heavy or light chain variable region sequence set forth as SEQ ID NOs:1, 3, 5, 7 or 9, and 11 or 13. Such variants can bind to antigen (e.g., NONO/nmt55 protein) or epitope of an antigen to which a reference antibody (e.g., LM-1) binds.

The invention also provides antibodies and functional fragments thereof that have a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55 protein) or a cell (e.g., a neoplastic, cancer, tumor or metastatic cell). In various embodiments, antibodies and functional fragments have a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55 protein), or stomach adenocarcinoma (e.g., diffuse or intestinal), colorectal cancer such as adenocarcinoma, ovarian carcinoma, lung cancer, such as lung adenocarinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia. In additional embodiments, an antibody or functional fragment has a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55 protein), or one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells. In further embodiments, an antibody or functional fragment has a binding affinity within about KD $10^{-5}$ M to about KD $10^{-13}$ M for binding to an antigen (e.g., NONO/nmt55 protein), or one or more cells or cell lines set forth herein (e.g., stomach adenocarcinoma, colorectal cancer such as adenocarcinoma, ovarian carcinoma, lung cancer, such as lung adenocarinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia, etc., or one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

Antibodies of the invention include IgG, IgA, IgM, IgE and IgD. In various aspects, an IgG is an IgG1, IgG2, IgG3, or IgG4.

Antibody functional fragments and subsequences of the invention include functional fragments and subsequences of the various antibodies set forth herein. In a particular embodiment, a functional fragment of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 that competes with LM-1 antibody, as represented by antibody produced by a cell line DSMZ Deposit No. DSM ACC 2623, or represented by heavy and light chain sequences set forth as SEQ ID NOs:1, 3, 5 or 7, and 9 for binding to a cell or an antigen (e.g., NONO/nmt55 protein), or that retains at least partial binding to a cell or antigen to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, is provided. In particular aspects, a functional fragment or a subsequence is an Fab, Fab', F(ab')$_2$, Fv, Fd, single-chain Fv (scFv), disulfide-linked Fvs (sdFv), V$_L$, V$_H$, trispecific (Fab$_3$), bispecific (Fab$_2$), diabody ((V$_L$-V$_H$)$_2$ or (V$_H$-V$_L$)$_2$), triabody (trivalent), tetrabody (tetravalent), minibody ((scF$_V$-C$_H$3)$_2$), bispecific single-chain Fv (Bis-scFv), IgGdeltaCH2, scFv-Fc and (scFv)$_2$-Fc. In additional aspects, a functional fragment or a subsequence of a full length antibody heavy or light chain, or a heavy or light chain variable region, includes one or more CDRs of a heavy or light chain sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67 or 100-118 of SEQ ID NO:1, 3, 5, 7 or 9, or amino acids 23-35, 51-58 or 90-101 of SEQ ID NO:11). In further aspects, a functional fragment or a subsequence of a full length antibody heavy or light chain, or a heavy or light chain variable region, has a length from about 20-30, 30-50, 50-100, 100-150, 150-200, 200-250, 250-300, 300-400, 400-500, amino acid residues.

The invention also provides antibodies and subsequences that include a heterologous domain. In one embodiment, a heterologous domain includes a detectable label, tag or cytotoxic agent. In particular aspects, a detectable label or tag is an enzyme, enzyme substrate, ligand, receptor, radionuclide, a T7-, His-, myc-, HA- or FLAG-tag, electron-dense reagent, energy transfer molecule, paramagnetic label, fluorophore, chromophore, chemi-luminescent agent, or a bio-luminescent agent.

The invention moreover provides nucleic acid sequences that encode antibodies and functional fragments thereof. In one embodiment, a nucleic acid sequence is at least 75-100% complementary or identical to a nucleic acid sequence that encodes a heavy or a light chain variable region sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a subsequence thereof (e.g, amino acids 24-35, 52-67 or 100-118 of SEQ ID NO:1, 3, 5 or 7, or amino acids 23-35, 51-58 or 90-101 of SEQ ID NO:9). In another embodiment, a nucleic acid encodes a subsequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67 or 100-118 of SEQ ID NO:1, 3, 5, 7 or 9, or amino acids 23-35, 51-58 or 90-101 of SEQ ID NO:11 or 13). In particular aspects, a nucleic acid sequence has a length from about 10-20, 20-30, 30-50, 50-100, 100-150, 150-200, 200-250, 250-300, 300-400, 400-500, or 500-1000 nucleotides. In additional aspects, a nucleic acid sequence specifically hybridizes to a nucleic acid that encodes SEQ ID NO:1, 3, 5, 7 or 9, and 11 or 13, or a subsequence thereof, or specifically hybridizes to a nucleic acid sequence complementary to a nucleic acid that encodes SEQ ID NO:1, 3, 5, 7 or 9, and 11 or 13 or a subsequence SEQ ID NO:1, 3, 5, 7 or 9, and 11 or 13. In further aspects, a nucleic acid is an antisense polynucleotide, a small interfering RNA, or a ribozyme nucleic acid that specifically hybridizes to a nucleic acid sequence encoding or complementary to SEQ ID NO:1, 3, 5, 7 or 9, and 11 or 13 or a subsequence thereof. Antisense polynucleotides, small interfering RNA, and ribozyme polynucleotides can have a length from about 10-20, 20-30, 30-50, 50-100, 100-150, 150-200, 200-250, 250-300, 300-400, 400-500, 500-1000, 1000-2000 nucleotides, and be at least 90% complementary or identical to a nucleic acid sequence that encodes SEQ ID NOs:1, 3, 5, 7 or 9, and 11 or 13 or a subsequence thereof (e.g., 24-35, 52-67 or 100-118 of SEQ ID NO:1, 3, 5, 7 or 9, or amino acids 23-35, 51-58 or 90-101 of SEQ ID NO:11 or 13). In still further aspects, nucleic acid sequence can include an expression control sequence or a vector (e.g., a viral, bacterial, fungal or mammalian vector).

The invention additionally provides isolated and purified cells as well as transformed host cells that express an antibody or subsequence thereof that includes a sequence at least 60% or more (e.g., 65%, 70%, 75%, 80%, 85%, 90%, 95%, etc.) identical to a heavy or light chain variable region sequence set forth as SEQ ID NO:1, 3, 5, 7 or 9, and 11 or 13 or a sequence at least 60% or more (e.g., 65%, 70%, 75%, 80%, 85%, 90%, 95%, etc.) identical to a heavy or light chain variable region sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. Such cells include eukaryotic and non-eukaryotic cells, which can stably or transiently express antibody or subsequence thereof, or be stably or transiently transformed with the nucleic acid or vector that encodes antibody or subsequence thereof or.

The invention further provides kits. In various embodiments, a kit includes an antibody or functional fragment thereof that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55 protein) or to a cell (e.g., a neoplastic, cancer, tumor or metastatic cell). In particular aspects, a kit includes an antibody or functional fragment thereof that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia. In an additional embodiment, a kit includes an antibody or functional fragment thereof that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55 protein), or one of lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

Kits of the invention also include antibodies and functional fragments that bind to cells or an antigen (e.g., NONO/nmt55 protein) that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In one embodiment, a kit includes an antibody or functional fragment that binds to an adenocarcinoma cell or a squamous cell carcinoma to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, such as a stomach adenocarcinoma (e.g., diffuse or intestinal) cell, a lung adenocarcinoma cell, a pancreas adenocarcinoma cell, a colon adenocarcinoma cell, a breast adenocarcinoma cell, an esophagus squamous cell carcinoma, to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In another embodiment, a kit includes an antibody or functional fragment binds to a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinomas, breast cancer such as invasive ductal or lobular cancer, gastric cancer, pancreatic cancer, such as pancreatic adenocarcinomas (e.g., ductal), sarcomas, gastrointestinal cancer such as a stomach cancer, nervous tissue or brain tumor such as a glioma, esophageal cancer such as esophagial squamous cell carcinomas and adenocarcinomas, osteosarcoma, fibrosarcomas, urinary bladder cancer, prostate cancer such as prostate adenocarcinomas, kidney cancer such as renal carcinoma, ovarian cancer such as adenocarcinomas, testicular cancer, endometrial cancer, cervical cancer such as squamous cell and adenocarcinomas, uterine cancers such as adenocarcinomas, Hodgkin's disease, lymphoma, or leukemia to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In an additional embodiment, a kit includes an antibody or functional fragment that binds to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds.

Kits of the invention further include antibodies and functional fragments that include a heavy or light chain variable region sequence with about 60% or more identity to a heavy or light chain sequence variable regions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In one embodiment, a kit includes an antibody or subsequence thereof with a sequence at least 60% or more (e.g., 65%, 70%, 75%, 80%, 85%, 90%, 95%, etc.) identical to a heavy chain variable region sequence set forth as SEQ ID NO:1, 3, 5, 7 or 9, or to a sequence at least 60% or more (e.g., 65%, 70%, 75%, 80%, 85%, 90%, 95%, etc.) identical to a light chain variable region sequence set forth as SEQ ID NO:11 or 13. In another embodiment, a kit includes an antibody or subsequence with a sequence at least 60% or more (e.g., 65%, 70%, 75%, 80%, 85%, 90%, 95%, etc.) identical to a heavy chain variable region sequence set forth as SEQ ID NO: 1, 3, 5, 7 or 9, and to a sequence at least 60% or more (e.g., 65%, 70%, 75%, 80%, 85%, 90%, 95%, etc.) identical to a light chain variable region sequence set forth as SEQ ID NO:11 or 13. In further embodiments, a kit includes an antibody or subsequence with a sequence at least 80-85%, 85-90%, 90-95%, 95-100% identical to one or more CDRs in heavy chain variable region sequence set forth as SEQ ID NO:1, 3, 5, 7 or 9, (e.g., amino acids 24-35, 52-67 or 100-118 of SEQ ID NO:1, 3, 5 or 7), or one or more CDRs in a heavy chain variable region of antibody produced by a cell line DSMZ Deposit No. DSM ACC 262, or a sequence at least 80-85%, 85-90%, 90-95%, 95-100% identical to one or more CDRs in a light chain variable region sequence set forth as SEQ ID NO:11 or 13 (e.g., amino acids 23-35, 51-58 or 90-101 of SEQ ID NO:11), or one or more CDRs in a light chain variable region of antibody produced by a cell line DSMZ Deposit No. DSM ACC 262.

In additional embodiments, a kit also includes an anti-cell proliferative or immune enhancing treatment or therapeutic agent, or an anti-neoplastic, anti-cancer or anti-tumor or anti-metastatic agent, or an article of manufacture (e.g., for delivering the antibody, anti-cell proliferative or immune enhancing treatment or therapy into a subject locally, regionally or systemically). In particular aspects, the instructions are for treating undesirable cell proliferation or a cell proliferative disorder (e.g., a neoplasia, tumor cancer or metastasis).

The invention yet additionally provides pharmaceutical compositions. In one embodiment, a composition includes an antibody or functional fragment and a pharmaceutically acceptable carrier or excipient. In another embodiment, a composition includes an antibody that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or an antigen (e.g., NONO/nmt55 protein), or that binds to a cell or an antigen (e.g., NONO/nmt55 protein) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, or that includes a heavy or light chain variable region sequence with about 60% or more identity to a heavy or light chain sequence variable regions as set forth in SEQ ID NOs:1, 3, 5, 7 or 9, and 11 or 13 or a sequence at least 80-85%, 85-90%, 90-95%, 95-100% identical to one or more CDRs in a heavy chain or light chain variable region sequence set forth as SEQ ID NO:1, 3, 5, 7 or 9, and 11 or 13 (e.g., amino acids 24-35, 52-67 or 100-118 of SEQ ID NO:1, 3, 5 or 7, or amino acids 23-35, 51-58 or 90-101 of SEQ ID NO:11), and a pharmaceutically acceptable carrier or excipient. In a further embodiment, a composition includes an antigen (e.g., NONO/nmt55 protein) and a pharmaceutically acceptable carrier or excipient Antibodies, functional fragments and antigen (e.g., NONO/nmt55 protein), modified forms are useful for treating a subject in need of treatment. The invention therefore provides methods of using antibodies, functional fragments an antigen (e.g., NONO/nmt55 protein) in treatment (e.g., therapeutic or prophylactic) of a subject having or at risk of having undesirable cell proliferation, such as a cell proliferative or hyperproliferative disorder. In one embodiment, a method includes administering an antibody or functional fragment (e.g., a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13) or an antigen (e.g., NONO/nmt55 protein) to a subject having or at risk of having undesirable cell proliferation (e.g., a cell proliferative disorder) an amount effective to treat undesirable cell proliferation. In particular aspects, a cell proliferative disorder is a metastatic or non-metastatic, solid or liquid neoplasia, malignancy, tumor or cancer. In various aspects, undesirable cell proliferation (e.g., a cell proliferative disorder) affects or is present at least in part in brain, head or neck, breast, esophagus, mouth, nasopharynx, nose or sinuses, stomach, duodenum, ileum, jejunum, lung, liver, pancreas, kidney, adrenal gland, thyroid, bladder, colon, rectum, prostate, uterus, endometrium, cervix, ovary, bone marrow, lymph, blood, bone, testes, skin or muscle, or hematopoetic system. In additional aspects, undesirable cell proliferation (e.g., a cell proliferative disorder) includes a neoplasia, tumor, cancer or metastasis that affects or is at least in part present in breast, lung, thyroid, head and neck, nasopharynx, nose or sinuses, brain, spine, adrenal gland, lymph, gastrointestinal tract, mouth, esophagus, stomach, duodenum, ileum, jejunum, small intestine, colon, rectum, genito-urinary tract, uterus, endometrium, ovary, cervix, bladder, testicle, penis, prostate, kidney, pancreas, adrenal gland, liver, bone, bone marrow, lymph, blood, muscle, skin or is hematopoetic. In further particular aspects, a neoplasia, tumor, cancer or metastasis is a sarcoma, carcinoma, adenocarcinoma, melanoma, myeloma, blastoma, glioma, lymphoma or leukemia. In additional particular aspects, a neoplasia, tumor or cancer is a stomach adenocarcinoma (e.g., diffuse or intestinal), colorectal cancer such as adenocarcinoma, ovarian carcinoma, lung cancer, such as lung adenocarcinomas, squamous cell lung carcinoma and small cell lung carcinoma, melanoma, lobular and ductal mammary carcinoma, breast cancer such as invasive ductal or lobular cancer, gastric cancer, pancreatic cancer, such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma or adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell or adenocarcinoma, uterine cancer such as adenocarcinoma, or Hodgkin's disease, or a metastasis thereof.

In another embodiment, a method includes administering an antibody or functional fragment (e.g., a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13) or an antigen (e.g., NONO/nmt55 protein) to a subject having or at risk of having a metastasis an amount effective to reduce or inhibit spread or dissemination of a tumor, cancer or neoplasia to other sites, locations or regions within the subject. In various aspects, a method reduces or inhibits metastasis of a primary tumor or cancer to one or more other sites, the formation or establishment of a metastasis at one or more other sites, thereby inhibiting or reducing tumor or cancer relapse or tumor or cancer progression. In further aspects, a method reduces or inhibits growth, proliferation, mobility or invasiveness of tumor or cancer cells that potentially or do develop, form or establish metastases; reduces or inhibits formation or establishment of metastases arising from a primary tumor or cancer to one or more other sites, locations or regions distinct from the primary tumor or cancer; reduces or inhibits growth or proliferation of a metastasis at one or more other sites, locations or regions distinct from the primary tumor or cancer after the metastasis has formed or has been established; or reduces or inhibits formation or establishment of additional metastasis after the metastasis has been formed or established.

In further particular aspects, a neoplasia, tumor or cancer, or metastasis is progressively worsening or is in remission. In still additional aspects, treatment results in alleviating or ameliorating one or more adverse physical symptoms associated with a cell proliferative disorder, or a neoplasia, tumor or cancer, or reduces or decreases neoplasia, tumor or cancer volume, inhibits or prevents an increase in neoplasia, tumor or cancer volume, inhibits neoplasia, tumor or cancer progression or worsening, stimulates neoplasia, tumor or cancer cell lysis or apoptosis, or inhibits, reduces or decreases neoplasia, tumor or cancer proliferation or metastasis, or prolongs or extends lifespan of the subject, or improves the quality of life of the subject.

Methods include administration to a subject locally, regionally, or systemically. Exemplary subjects (e.g., mammals such as humans) include candidates for, and those undergoing, or having undergone an anti-cell proliferative or anti-hyperproliferative disorder (e.g., anti-neoplastic, anti-tumor, anti-cancer or anti-metastasis) or immune-enhancing treatment or therapy.

The invention yet also provides combined methods for treating a disorder in a subject in need of treatment. In one embodiment, a method includes administering to a subject an antibody that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding of to an antigen (e.g., NONO/nmt55 protein) or cell, or binds to a cell to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds and an anti-cell proliferative or immune-enhancing treatment or therapy to a subject (e.g., prior to, substantially contemporaneously with or following each other). In another embodiment, an antigen (e.g., NONO/nmt55 protein) to which LM-1 antibody binds, and an anti-cell proliferative or immune-enhancing treatment or therapy to a subject (e.g., prior to, substantially contemporaneously with or following each other). In various aspects, an anti-cell proliferative or immune-enhancing treatment or therapy includes surgical resection, radiotherapy, radiation therapy, chemotherapy, immunotherapy, hyperthermia, an alkylating agent, anti-metabolite, plant extract, plant alkaloid, nitrosourea, hormone, nucleoside or nucleotide analogue, a lymphocyte, plasma cell, macrophage, dendritic cell, NK cell or B-cell, an antibody, a cell growth factor, a cell survival factor, a cell differentiative factor, a cytokine, an interferon or a chemokine.

Antibodies and functional fragments thereof are useful for detecting, screening for and identifying the presence of cells or an antigen (e.g., NONO/nmt55 protein) that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or antigen that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. The invention therefore provides methods for detecting or screening for cells and antigens (e.g., NONO/nmt55 protein) that bind to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 methods for identifying a subject that is amenable to treatment in accordance with the methods of the invention. In one embodiment, a method includes contacting a biological material or sample with an antibody or functional fragment under conditions allowing binding between antibody or functional fragment and cell or antigen that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 and assaying for binding of the antibody or functional fragment to a cell or antigen that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. The binding of the antibody or functional fragment to a cell or antigen that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 indicates that the biological material contains the cell or antigen that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In another embodiment, a method includes analyzing a biological sample for the presence of an antigen to which LM-1 antibody binds (e.g., NONO/nmt55). The presence of a cell or antigen (e.g., NONO/nmt55) that binds to LM-1 identifies a subject that is amenable to treatment in accordance with the methods of the invention. In one aspect, the biological material or sample is obtained from a mammalian (e.g., primate, such as a human) subject.

The invention moreover provides methods for diagnosing a subject having or at increased risk of having undesirable cell proliferation or a cell proliferative disorder (e.g., neoplasia, tumor or cancer, or metastasis), methods of determining or ascertaining the presence or extent of undesirable or aberrant cell proliferation or a cellular hyperproliferative disorder (e.g., neoplasia, tumor or cancer, or metastasis), as well as methods of identifying a subject appropriate for treatment with an LM-1 antibody, or an antibody that binds to an LM-1 antigen (e.g., NONO/nmt55). In various embodiments, a method includes contacting a biological material or sample from a subject with an antibody or functional fragment that competes with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding or an antibody or functional fragment that binds to a cell or antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, or an antibody or functional fragment that includes a heavy or light chain variable region sequence with about 60% or more identity to a heavy or light chain sequence variable regions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 under conditions allowing binding of the antibody or functional fragment, and assaying for binding of the antibody to a cell or antigen (e.g., NONO/nmt55) that binds to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. The presence or amount of a cell or an LM-1 antigen (e.g., NONO/nmt55) can be correlated with the presence or extent of a neoplasia, tumor or cancer, thereby diagnosing a subject having or at increased risk of having undesirable cell proliferation or a cell proliferative disorder (e.g., neoplasia, tumor or cancer, or metastasis), or establishing the presence or extent of a neoplasia, tumor or cancer. The presence or amount of a cell or an antigen (e.g., NONO/nmt55) can also identify a subject appropriate for treatment with an LM-1 antibody, or an antibody that binds to an LM-1 antigen (e.g., NONO/nmt55), due to an increased probability of responding to treatment. In particular aspects, the methods for diagnosing a subject identify those that have (e.g., the presence or extent) or are at increased risk of having undesirable cell proliferation or a cell proliferative disorder (e.g., neoplasia, tumor or cancer, or metastasis). In one aspect, the biological material or sample is obtained from a mammalian (e.g., primate, such as a human) subject. In additional aspects, the biological material or sample comprises a biopsy, such as a lung, pancreas, stomach, breast, esophageal, ovarian or uterine biopsy.

Figure 10:
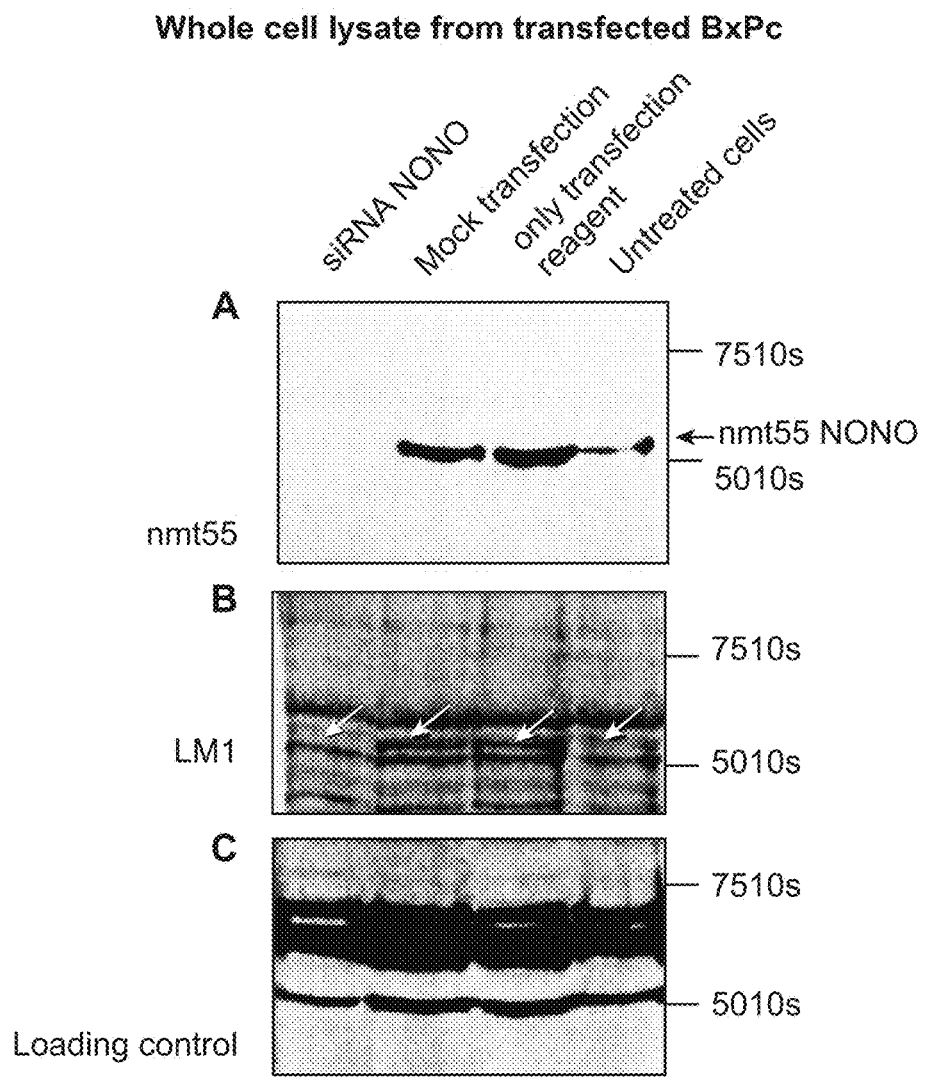

FIGS. 10A-10C show siRNA transfected BxPc-3 cells to downregulate expression of NONO/nmt55 and reduced binding of LM-1. A) siRNA downregulated NONO/nmt55 expression; B) Binding of LM-1 to siRNA transfected cells was reduced (arrow) and C) Load Control.

FIGS. 11A-11D show immunoprecipitation of MKN cells with anti nmt55 antibody, and subsequent staining with A) anti NONO/nmt55 Mouse mAb/anti mouse IgG HRP; B), anti mouse IgG HRP; C), LM-1/anti human IgM HR; and D), anti human IgM HRP. The top (higher molecular weight) arrow is NONO, and the bottom (lower molecular weight) arrow is mouse heavy chain.

FIGS. 12A-12B show immunoprecipitation of BxPC-3 cells with anti nmt55, and subsequent staining with A) LM-1; and B) anti NONO/nmt55. Arrows indicate nmt55 and mouse IgG heavy chain.

FIGS. 13A-13B show immunoprecipitation of A549 cells with anti nmt55 and subsequent staining with A) anti NONO/nmt55; and B) LM-1. Arrows indicate positions of nmt55 and mouse IgG heavy chain.

Figure 14:
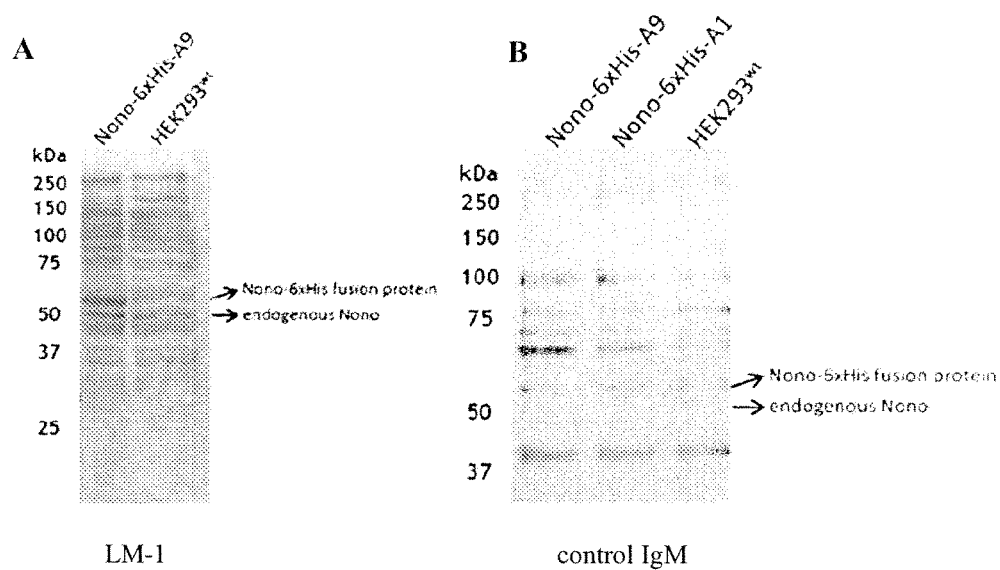

FIGS. 14A-14B show data indicative of LM-1 binding to recombinantly expressed NONO/nmt55-6×His protein.

Figure 15:
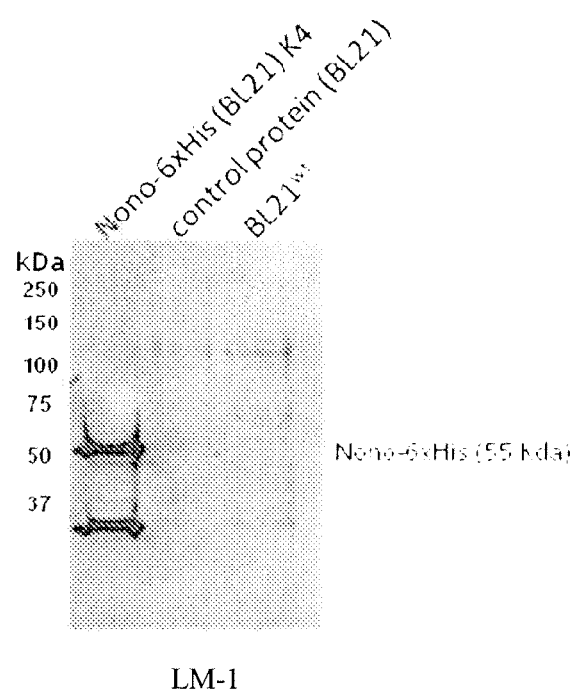

FIG. 15 show data indicative of LM-1 binding to bacterially expressed NONO/nmt55-6×His protein.

Figure 16:
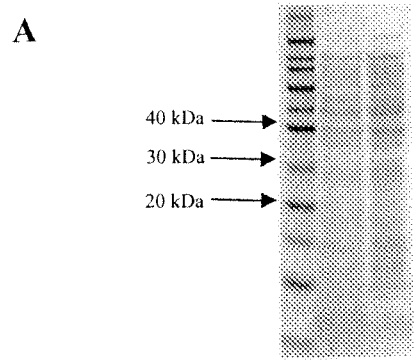
Figure 16:
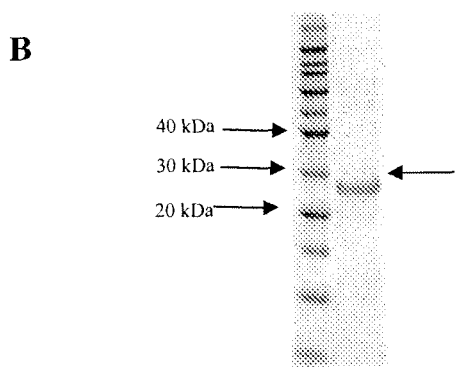
Figure 16:
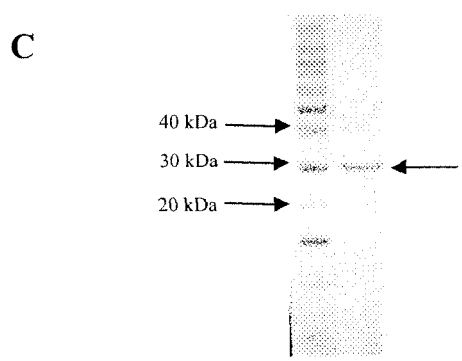

FIGS. 16A-16C show a polyacrylamide gel electrophoresis (PAGE) analysis of A) nmt55 expression Lane 1) Novex Sharp molecular weight marker, Lane 2) $T_o$ sample showing baseline level of protein expression, Lane 3) $T_{FINAL}$ showing level of nmt55 expression post heat induction; B) nmt55 following Profina™ purification Lane 1) Novex Sharp molecular weight marker, Lane 2) Purified and concentrated nmt55 from periplasmic expression; and C) a western blot of nmt55 following Profina™ purification Lane 1) Novex Sharp molecular weight marker, Lane 2) Purified and concentrated nmt55 detected using LM-1opt scFv.

DETAILED DESCRIPTION

The invention is based, at least in part, on antibodies that bind to various neoplastic, cancer, tumor and metastatic cells. A non-limiting exemplary antibody is designated LM-1 antibody, as represented by antibody produced by a cell line DSMZ Deposit No. DSM ACC 2623, deposited on Nov. 6, 2003 at the German Collection of Microorganisms and Cell Cultures ("DSMZ"—Deutsche Sammlung von Mikroorganismen and Zellkulturen GmbH, Mascheroder Weg lb, 38124 Braunschweig, Germany) under the terms of the Budapest Treaty, or represented by heavy and light chain sequences set forth as SEQ ID NOs:1, 3, 5, 7 or 9, and 11 or 13. LM-1 antibody, represented by antibody produced by a cell line DSMZ Deposit No. DSM ACC 2623, or represented by heavy and light chain sequences set forth as SEQ ID NOs:1, 3, 5, 7 or 9, and 11 or 13 is a human IgM antibody that specifically binds to various neoplastic, cancer, tumor and metastatic cells. LM-1 therefore binds to an antigen expressed on various neoplastic, cancer, tumor and metastatic cells. LM-1 is able to inhibit or reduce proliferation of various neoplastic, cancer, tumor and metastatic cells. LM-1 is also able to stimulate or induce apoptosis of various neoplastic, cancer, tumor and metastatic cells.

The invention is also based, at least in part, on identification of a target of LM-1, i.e., an antigen that binds to LM-1. As disclosed herein, LM-1 antibody binds to non-pou domain-containing octamer-binding protein (NONO), also known as 54 kDa nuclear RNA- and DNA-binding protein (p54nrb) and 55 kDa nuclear protein (nmt55). NONO/nmt55 can be target for treatment of a neoplasia, cancer, tumor or metastasis. NONO/nmt55 can be a diagnostic indicator of a neoplasia, cancer, tumor or metastasis. For example, detection of NONO/nmt55 on cell surface can indicate the presence of a neoplasia, cancer, tumor or metastasis. NONO/nmt55 can be also be a vaccine. For example, NONO/nmt55 can be adminstered to a subject with a neoplasia, cancer, tumor or metastasis that expresses cell surface NONO/nmt55 in order to elicit an immune response against the a neoplasia, cancer, tumor or metastasis.

Antibodies of the invention include polyclonal and monoclonal antibodies. Antibodies are proteins which include amino acids, or "residues," covalently linked by an amide bond or equivalent. The term "monoclonal," when used in reference to an antibody refers to an antibody that is based upon, obtained from or derived from a single clone, including any eukaryotic, prokaryotic, or phage clone. A "monoclonal" antibody is therefore defined herein structurally, and not the method by which it is produced.

Antibodies of the invention can belong to any antibody class, IgM, IgG, IgE, IgA, IgD, or subclass. Exemplary subclasses for IgG are $IgG_1$, $IgG_2$, $IgG_3$ and $IgG_4$.

Antibodies of the invention can have kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa or two lambda light chains.

The amino acid sequences and nucleic acid sequences of LM-1 antibody, as represented by various heavy and light chain variable region sequences, SEQ ID NOs:1-10, are as follows:

The heavy chain variable region of the human monoclonal antibody LM-1, as represented by amino acid sequences (SEQ ID NOs:1, 3, 5, 7 and 9) and nucleic acid sequences (SEQ ID NOs:2, 4, 6, 8 and 10), respectively, with differences shown in bold, are as follows:

Amino acid sequence of LM-1 heavy chain variable (VH) region sequence, as represented by SEQ ID NO:1:

```
QVQLQESGPGLVKPSPTLSLTCAVSGGSISSGGYYWSWIRQHPGKGLEWI
GYIYYSGSTYYNPSLKSRVTISVDTSKNQFSLKLSSVTAADTAVYYCARV
DARYDYVWGSYRYDAFDIWGQGTMVTVSS
```

Amino acid sequence of LM-1 heavy chain variable (VH) region sequence, as represented by SEQ ID NO:3 (1BTA1.16VH):

```
QVQLQESGPGLVKPSQTLSLTCAVSGGSISSGGYYWSWIRQHPGKGLEWI
GYIYYSGSTYYNPSLKSRVTISVDTSKNQFSLKLSSVTAADTAVYYCARV
DARYDYVWGSYRYDAFDIWGQGTMVTVSS
```

Amino acid sequence of LM-1 heavy chain variable (VH) region sequence, as represented by SEQ ID NO:5 (1BTA1.7 VH):

```
QVQLQESGPGLVKPSPTLSLTCAVSGGSISSGGYYWSWIRQHPGKGLEWI
GYIYYSGSTYYNPSLKSRVTISVDTSKNQFSLKLSSVTAADTAVYYCARV
DARYDYVWGSYRFDAFDIWGQGTMVTVSS
```

Amino acid sequence of LM-1 heavy chain variable (VH) region sequence, as represented by SEQ ID NO:7 (1 BTA2.5 VH):

QLQLQESGPGLVKPSQTLSLTCTVSGGSISSGGYYWSWIRQHPGKGLEWI
GYIYYSGSTYYNPSLKSRVTISVDTSKNQFSLKLSSVTAADTAVYYCARV
DARYDYVWGSYRYDAFDIWGQGTMVTVSS

Amino acid sequence of LM-1 heavy chain variable (VH) region sequence, as represented by SEQ ID NO:9 (VHL1opt):

EVQLVESGGGLVQPGGSLRLSCAVSGGSISSGGYYWSWIRQAPGKGLEW
VIGYIYYSGSTYYADSVKGRFTISRDNSKNTLYLQMNSLRAEDTAVYYC
ARVDARYDYVWGSYRYDAFDIWGQGTLVTVSS

Nucleotide sequence of LM-1 heavy chain variable (VH) region sequence, as represented by SEQ ID NO:2:

```
CCGACCCTGT CCCTCACCTG CGCTGTCTCT GGTGGCTCCA TCAGCAGTGG TGGTTACTAC      60
TGGAGCTGGA TCCGCCAGCA CCCAGGGAAG GGCCTGGAGT GGATTGGGTA CATCTATTAC     120
AGTGGGAGCA CCTACTACAA CCCGTCCCTC AAGAGTCGAG TTACCATATC AGTAGACACG     180
TCTAAGAACC AGTTCTCCCT GAAGCTGAGC TCTGTGACTG CCGCGGACAC GGCCGTGTAT     240
TACTGTGCGA GAGTTGATGC GCGATATGAT TACGTTTGGG GGAGTTATCG TTATGATGCT     300
TTTGATATCT GGGGCCAAGG AACCCTGGTC ACCGTCTCTT CA                        333
```

Nucleotide sequence of LM-1 heavy chain variable (VH) region sequence, as represented by SEQ ID NO:4 (1BTA1.16VH):

CAGGTGCAGCTGCAGGAGTCGGGCCCAGGACTGGTGAAGCCTTCACA
GACCCTGTCCCTCACCTGCGCTGTCTCTGGTGGCTCCATCAGCAGTGGT
GGTTACTACTGGAGCTGGATCCGCCAGCACCCAGGGAAGGGCCTGGA
GTGGATTGGGTACATCTATTACAGTGGGAGCACCTACTACAACCCGTC
CCTCAAGAGTCGAGYTACCATATCAGTAGACACGTCTAAGAACCAGTI
CTCCCTGAAGCTGAGCTCTGTGACTGCCGCGGACACGGCCGTGTATTA
CTGTGCGAGAGTTGATGCGCGATATGATTACGTTTGGGGGAGTTATCG
TTATGATGCTTTTGATATCTGGGGCCAAGGGACAATGGTCACCGTCTC
TTCA

Nucleotide sequence of LM-1 heavy chain variable (VH) region sequence, as represented by SEQ ID NO:6 (1BTA1.7 VH):

CAGGTGCAGCTGCAGGAGTCGGGCCCAGGACTGGTGAAGCCTTCACC
GACCCTGTCCCTCACCTGCGCTGTCTCTGGTGGCTCCATCAGCAGTGGT
GGTTACTACTGGAGCTGGATCCGCCAGCACCCAGGGAAGGGCCTGGA
GTGGATIGGGTACATCTATTACAGTGGGAGCACCTACTACAACCCGTC
CCTCAAGAGTCGAGTTACCATATCAGTAGACACGTCTAAGAACCAGTT
CTCCCTGAAGCTGAGCTCTGTGACTGCCGCGGACACGGCCGTGTATTA
CTGTGCGAGAGTTGATGCGCGATATGATTACGTTTGGGGGAGTTATCG
TTTTGATGCTTTTGATATCTGGGGCCAAGGGACAATGGTCACCGTCTCT
TCA

Nucleotide sequence of LM-1 heavy chain variable (VH) region sequence, as represented by SEQ ID NO:8 (1BTA2.5 VH):

CAGCTGCAGCTGCAGGAGTCGGGCCCAGGACTGGTGAAGCCTTCACA
GACCCTGTCCCTCACCTGCACTGTCTCTGGTGGCTCCATCAGCAGTGG
TGGTTACTACTGGAGCTGGATCCGCCAGCACCCAGGGAAGGGCCTGG
AGTGGATTGGGTACATCTATTACAGTGGGAGCACCTACTACAACCCGT
CCCTCAAGAGTCGAGTTACCATATCAGTAGACACGTCTAAGAACCAGT
TCTCCCTGAAGCTGAGCTCTGTGACTGCCGCGGACACGGCCGTGTATT
ACTGTGCGAGAGTTGATGCGCGATATGATTACGTTTGGGGGAGTTATC
GTTATGATGCTTTTGATATCTGGGGCCAAGGGACAATGGTCACCGTCT
CTTCA

Nucleotide sequence of LM-1 heavy chain variable (VH) region sequence, as represented by SEQ ID NO:10 (VHL1opt):

GAGGTGCAGCTGGTCGAGAGCGGGGGAGGCCTGGTGCAGC
CAGGGGGATCTCTGAGACTGAGCTGCGCCGTGAGCGGCGGATCTATTT
CCAGCGGGGATATTATTGGTCTTGGATCAGACAGGCTCCCGGAAAGG
GGCTGGAATGGGTCATCGGCTACATCTACTACAGCGGCAGCACCTACT
ACGCCGACAGCGTGAAGGGCCGGTTCACCATCAGCCGGGACAACAGC
AAGAACACCCTGTACCTGCAGATGAACAGCCTGCGGGCCGAGGACAC
CGCGGTGTACTACTGCGCCAGAGTGGACGCCAGATACGACTACGTGTG
GGGCAGCTACAGATACGACGCCTTCGACATCTGGGGCCAGGGCACCC
TGGTGACCGTGTCTTCT

The light chain variable regions of the human monoclonal antibody LM-1, as represented by amino acid sequences (SEQ ID NO:11 and 13) and nucleic acid sequences (SEQ ID NO:12 and 14), respectively, are as follows:

Amino acid sequence of LM-1 light chain variable (VL) region sequence, as represented by SEQ ID NO:11:

```
QSVLTQPPSVSAAPGQKVTISCSGSSSNIGNNYVSWYQQLPGTAPKLLIY

DNNKRPSGIPDRFSGSKSGTSATLGITGLQTGDEADYYCGTWDSSLSAGW

VFGGGTKLTVLGQ
```

Amino acid sequence of LM-1 light chain variable (VL) region sequence, as represented by SEQ ID NO:13 (VKL1opt):

```
DIQMTQSPSSLSASVGDRVTITCRSGSSSNIGNNYVSWYQQKPGKAPKLL

IYDNNKEPSGVPSRFSGSGSGTDFTLTISSLQPEDFATYYCQGTWDSSLS

AGWVFGQGTKVEIKR
```

Amino acid sequence of LM-1 light chain (L) sequence, as represented by SEQ ID NO:15:

```
MACPGFLWALVISTCLEFSMASWAQSVLTQPPSVSAAPGQKVTISCSGSS

SNIGNNYVSWYQQLPGTAPKLLIYDNNKRPSGIPDRFSGSKSGTSATLGI

TGLQTGDEADYYCGTWDSSLSAGWVFGGGTKLTVLGQPKAAPSVTLFPPS

SEELQANKATLVCLISDFYPGAVTVAWKADSSPVKAGVETTTPSKQSNN

KYAASSYLSLTPEQWKSHKSYSCQVTHEGSTVEKTVAPTECS
```

Nucleotide sequence of LM-1 light chain variable (VL) region sequence, as represented by SEQ ID NO:12 (1BTA1.16 VL):

```
CAGTCTGTGTTGACGCAGCCGCCCTCAGTGTCTGCGGCCCCAGGACAG

AAGGTCACCATCTCCTGCTCTGGAAGCAGCTCCAACATTGGGAATAAT

TATGTATCCTGGTACCAGCAGCTCCCAGGAACAGCCCCCAAACTCCTC

ATTTATGACAATAATAAGCGACCCTCAGGGATTCCTGACCGATTCTCT

GGCTCCAAGTCTGGCACGTCAGCCACCCTGGGCATCACCGGACTCCAG

ACTGGGGACGAGGCCGATTATTACTGCGGAACATGGGATAGCAGCCT

GAGTGCTGGTTGGGTGTTCGGCGGAGGGACCAAGCTGACCGTCCTAGG

TCAG
```

Nucleotide sequence of LM-1 light chain variable (VL) region sequence, as represented by SEQ ID NO:14 (VKL1opt):

```
GACATCCAGATGACCCAGAGCCCCAGCAGCCTGAGCGCCAGCGTGGG

CGACAGAGTGACCATCACCTGCAGAAGCGGCAGCAGCAGCAACATCG

GCAACAATTATGTCTCTTGGTATCAGCAGAAACCTGGCAAGGCCCCCA

AGCTGCTGATCTACGACAACAACAAAGAACCCAGCGGCGTGCCCAGC

CGGTTTAGCGGCAGCGGCTCCGGCACCGACTTCACCCTGACCATCAGC

AGCCTGCAGCCCGAGGATTTCGCCACCTACTACTGTCAGGGGACATGG

GATAGCAGCCTGTCCGCCGGCTGGGTGTTCGGCCAGGGAACAAAG

GTGGAGATCAAGAGA
```

Predicted CDRs, of which there are three in each of heavy and light chain, are conveniently denoted herein as HC-CDR1, HC-CDR2 and HC-CDR3; and LC-CDR1, LC-CDR2 and LC-CDR3. CDR positions were based upon definitions of Kabat (e.g., *Sequences of Proteins of Immunological Interest*, 4th Ed. US Department of Health and Human Services. Public Health Service (1987), and Kabat et al., *Sequences of Proteins of Immunological Interest*, 5th Ed. US Department of Health and Human Services, Public Health Service (1991)), except numbering of CDRs is based upon amino acid residue number of the sequences set forth herein beginning from the amino-terminus and does not follow the Kabat numbering system. Heavy chain variable region CDR placement was modeled after herceptin antibody variable region (PDB file 1N8Z) due to 95% sequence identity with the framework residues, and light chain variable region CDR placement was modeled after PDB file 2RHEa due to 82% sequence identity with the framework residues.

Predicted CDR sequences of exemplary heavy variable region chain are CDR1; VSGGSISSGGYY (SEQ ID NO: 25), CDR2; YIYYSGSTYYNPSLKS (SEQ ID NO: 26), and CDR3; VDARYDYVWGSYRYDAFDI (SEQ ID NO: 27). CDR 1 of heavy chain spans nucleotides 72-105 which encode amino acids 24-35, CDR2 spans nucleotides 156-201 which encode amino acids 52-67, and CDR3 spans nucleotides 300-354 which encode amino acids 100-118.

Predicted CDR sequences of exemplary light variable region chain are 90-101, CDR1; SGSSSNIGNNYVS (SEQ ID NO: 28), CDR2; DNNKRPSG (SEQ ID NO: 29), and CDR3; GTWDSSLSAGWV (SEQ ID NO: 30). CDR1 of lambda light chain spans nucleotides 69-105 which encode amino acids located at positions 23-35. CDR2 spans nucleotides 153-174 which encode amino acids 51-58 and CDR3 spans nucleotides 270-303 and encode amino acids 90-101.

In accordance with the invention, there are provided isolated and purified antibodies and functional (e.g., cell or antigen binding) fragments structurally and/or functionally related to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, respectively. In various embodiments, antibodies and functional fragments compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or antigen (e.g., NONO/nmt55). In additional embodiments, antibodies and functional fragments compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55), or an adenocarcinoma cell or a squamous cell carcinoma.

In accordance with the invention, there are also provided isolated and purified antibodies and functional (e.g., cell or antigen binding) fragments that bind to NONO/nmt55 protein. In various embodiments, antibodies and functional fragments bind to an N-terminal NONO-nmt55 amino acid sequence region (e.g., amino acids 1-300 of NONO-nmt55). In one aspect, NONO-nmt55 includes a sequence set forth as:

```
                                                      (SEQ ID NO: 16)
  1 MQSNKTFNLE KQNHTPRKHH QHHHQQQHHQ QQQQQPPPPP IPANGQQASS

51 QNEGLTIDLK NFRKPGEKTF TQRSRLFVGN LPPDITEEEM RKLFEKYGKA

101 GEVFIHKDKG FGFIRLETRT LAEIAKVELD NMPLRGKQLR VRFACHSASL

151 TVRNLPQYVS NELLEEAFSV FGQVERAVVI VDDRGRPSGK GIVEFSGKPA

201 ARKALDRCSE GSFLLTTFPR PVTVEPMDQL DDEEGLPEKL VIKNQQFHKE

251 REQPPRFAQP GSFEYEYAMR WKALIEMEKQ QQDQVDRNIK EAREKLEMEM

301 EAARHEHQVM LMRQDLMRRQ EELRRMEELH NQEVQKRKQL ELRQEEERRR

351 REEEMRRQQE EMMRRQQEGF KGTFPDAREQ EIRMGQMAMG GAMGINNRGA

401 MPPAPVPAGT PAPPGPATMM PDGTLGLTPP TTERFGQAAT MEGIGAIGGT

451 PPAFNRAAPG AEFAPNKRRR Y
```

In another aspect, NONO-nmt55 includes a sequence set forth as:

```
                                     (residues 1-300 of SEQ ID NO: 16)
  1 MQSNKTFNLE KQNHTPRKHH QHHHQQQHHQ QQQQQPPPPP IPANGQQASS

51 QNEGLTIDLK NFRKPGEKTF TQRSRLFVGN LPPDITEEEM RKLFEKYGKA

101 GEVFIHKDKG FGFIRLETRT LAEIAKVELD NMPLRGKQLR VRFACHSASL

151 TVRNLPQYVS NELLEEAFSV FGQVERAVVI VDDRGRPSGK GIVEFSGKPA

201 ARKALDRCSE GSFLLTTFPR PVTVEPMDQL DDEEGLPEKL VIKNQQFHKE

251 REQPPRFAQP GSFEYEYAMR WKALIEMEKQ QQDQVDRNIK EAREKLEMEM
```

In further embodiments, antibodies and functional fragments compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding of to one or more of a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, and leukemia. In yet additional embodiments, antibodies and functional fragments compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55), or to one or more of a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, and leukemia. In still further embodiments, antibodies and functional fragments compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells. In particular aspects, antibodies and functional fragments competitively inhibit binding of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to a cell or an antigen (e.g., NONO/nmt55) by at least 30%, 40%, 50%, 60%, 70%, 80%, 90% or more.

In accordance with the invention, there are also provided antibodies and functional fragments that bind to a cell or an antigen (e.g., NONO/nmt55) that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In one embodiment, an isolated or purified antibody or functional fragment thereof binds to a cell or an antigen (e.g., NONO/nmt55) that LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In particular aspects, the antibody or functional fragment thereof binds to a cell or an antigen (e.g., NONO/nmt55) present on an adenocarcinoma cell or a squamous cell carcinoma to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In additional particular aspects, the antibody or functional fragment thereof binds to one or more of a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, and leukemia, to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In further particular aspects, the antibody or functional fragment thereof binds to a cell or an antigen (e.g., NONO/nmt55) present on a lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cell, to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds.

The term "bind," or "binding," when used in reference to an antibody or functional fragment, means that the antibody or functional fragment interacts at the molecular level with a corresponding epitope (antigenic determinant) present on a cell or an antigen (e.g., NONO/nmt55). Epitopes of antigens that comprise amino acids typically include relatively short sequences, e.g. about five to 15 amino acids in length. Epitopes can be contiguous or non-contiguous. A non-contiguous amino acid sequence epitope forms due to protein folding. Techniques for identifying epitopes are known to the skilled artisan and include screening overlapping oligopeptides for binding to antibody (for example, U.S. Pat. No. 4,708,871), phage display peptide library kits, which are commercially available for epitope mapping (New England BioLabs). Epitopes may also be identified by inference when epitope length peptide sequences are used to immunize animals from which antibodies that bind to the peptide sequence are obtained and can be predicted using computer programs, such as BEPITOPE (Odorico et al., *J. Mol. Recognit.* 16:20 (2003)).

The invention further provides antibodies and functional fragments that inhibit, decrease or reduce cell growth or proliferation, or stimulate or induce cell death, lysis or apoptosis. In particular embodiments, binding of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to a neoplastic, tumor or cancer, or metastasis cell inhibits, decreases or reduces cell growth or proliferation, or stimulates or induces cell death, lysis or apoptosis. In another embodiment, binding of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, or leukemia inhibits, decreases or reduces cell growth or proliferation, or stimulates or induces cell death, lysis or apoptosis. In a further embodiment, binding of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

The invention moreover provides of antibodies and functional fragments that are structurally and/or functionally related to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 which includes a heavy or light chain variable region sequence that exhibits a degree of identity to SEQ ID NOs:1, 3, 5, 7 or 9, and 11 or 13 or that exhibits a degree of identity to a sequence within SEQ ID NOs:1, 3, 5, 7 or 9, and 11 or 13 (e.g., one or more CDRs, such as amino acids 24-35, 52-67, or 100-118 of SEQ ID NO:1, 3, 5 or 7, or amino acids 23-35, 51-58 or 90-101 of SEQ ID NO:11). In particular embodiments, antibodies and functional fragments include a heavy or a light chain variable region sequence with about 60% or more identity to a heavy or light chain sequence variable region of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a sequence within LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., one or more CDRs, such as amino acids 24-35, 52-67 or 100-118 of SEQ ID NO:1, 3, 5, or 7, or amino acids 23-35, 51-58 or 90-101 of SEQ ID NO:11). In other particular embodiments, antibodies or functional fragments include a heavy or a light chain with at least 65%, 70%, 75%, 80%, 85%, 90%, 95%, or more identity to a heavy chain variable region sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a sequence within LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., one or more CDRs, such as amino acids 24-35, 52-67, or 100-118 of SEQ ID NO:1, 3, 5 or 7, or amino acids 23-35, 51-58 or 90-101 of SEQ ID NO:11). In additional particular embodiments, antibodies or functional fragments include a heavy or a light chain variable region sequence with at least 80-85%, 85-90%, 90-95%, 95-100% identity to one or more CDRs in LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67, or 100-118 of SEQ ID NO:1, 3, 5 or 7, or amino acids 23-35, 51-58 or 90-101 of SEQ ID NO:11). In a particular aspect, an antibody or a functional fragment thereof includes a heavy or a light chain variable region sequence with 95-100% identity to one, two or three CDRs in each heavy or light chain variable region sequences in LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67, or 100-118 of SEQ ID NO:1, 3, 5 or 7, or amino acids 23-35, 51-58 or 90-101 of SEQ ID NO:11).

Antibodies and functional fragments of the invention therefore include those with at least partial sequence identity to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. The percent identity of such antibodies and functional fragments can be as little as 60%, or can be more (e.g., 65%, 70%, 75%, 80%, 85%, 90%, 95%, etc.).

The percent identity can extend over the entire sequence length of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a contiguous region or area within LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In particular aspects, the length of the sequence sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, etc. contiguous amino acids. In additional particular aspects, the length of the sequence sharing the percent identity is 25 or more contiguous amino acids, e.g., 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet additional particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids. In yet further particular aspects, the length of the sequence sharing the percent identity is equal to the length of any CDR of a variable region sequence (e.g., amino acids 24-35, 52-67, or 100-118 of SEQ ID NO: 1, 3, 5, 7 or 9, or amino acids 23-35, 51-58 or 90-101 of SEQ ID NO:11), or a region outside the CDRs but within the variable region of a heavy or light chain sequence, such as LM-1 antibody, as represented by antibody produced by a cell line DSMZ Deposit No. DSM ACC 2623, or represented by heavy and light chain sequences set forth as SEQ ID NOs:1, 3, 5 or 7, and 9.

The term "identity" and grammatical variations thereof, mean that two or more referenced entities are the same. Thus, where two antibody sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. An "area of identity" refers to a portion of two or more referenced entities that are the same. Thus, where two protein or nucleic acid sequences are identical over one or more sequence regions they share identity within that region. Exemplary identity are antibodies and functional fragments with an amino acid sequence with 50%, 60%, 70%, 75%, 80%, 85%, 90%, 95%, 96%, 97%, 98%, or more sequence identity to a reference antibody or functional fragment, for example, LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a subsequence thereof.

The terms "homologous" or "homology" mean that two or more referenced entities share at least partial identity over a given region or portion. "Areas, regions or domains" of homology or identity mean that a portion of two or more referenced entities share homology or are the same. Thus, where two antibody sequences are identical over one or more sequence regions they share identity in these regions. "Substantial homology" means that a molecule is structurally or functionally conserved such that it has or is predicted to have at least partial structure or function of one or more of the structures or functions (e.g., a biological function) of the reference molecule, or relevant/corresponding region or portion of the reference molecule to which it shares homology. An antibody or functional fragment with substantial homology has or is predicted to have at least partial activity or function as the reference antibody. For example, in a particular embodiment, a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 with one or more modifications (e.g., substitutions, deletions or additions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13) retain the ability to at least partially compete for binding of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to a cell or an antigen (e.g., NONO/nmt55), or at least retains partial binding to a cell or antigen to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds is considered to have substantial homology to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

The extent of identity (homology) between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci.* USA 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Antibodies and functional fragments of the invention include those that retain at least one or more partial activities or functions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. As disclosed herein, the antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds is expressed on malignant and non-malignant, neoplastic, tumor and cancer cells. Non-limiting examples of cells that bind to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 and therefore express a target antigen of LM-1 include one or more of a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal and lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, and leukemia, or lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells. Thus, in various embodiments, an antibody or functional fragment binds to an antigen (e.g., NONO/nmt55), or one or more cells, such as a stomach adenocarcinoma (e.g., diffuse or intestinal), colorectal cancer such as adenocarcinoma, ovarian carcinoma, lung cancer, such as a lung adenocarcinoma, squamous cell lung carcinoma or small cell lung carcinoma, melanoma, lobular or ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma or adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, or leukemia, or lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

Antibodies and functional fragments that bind to a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds can have greater or less relative binding affinity for a cell or an antigen (e.g., NONO/nmt55) than LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. Additional antibodies and functional fragments of the invention therefore include those that have greater than, about the same or less than the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or an antigen (e.g., NONO/nmt55). For example, an antibody or functional fragment of the invention may have an affinity greater or less than 2-5, 5-10, 10-100, 100-1000 or 1000-10,000-fold affinity, or any numerical value or range within or encompassing such values, than LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In one embodiment, an antibody or a functional thereof has a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55), or to a neoplastic, cancer, tumor or metastatic cell. In another embodiment, an antibody or a functional thereof has a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to an antigen (e.g., NONO/nmt55), or to a stomach adenocarcinoma (e.g., diffuse or intestinal), colorectal cancer such as adenocarcinoma, ovarian carcinoma, lung cancer, such as a lung adenocarcinoma, squamous cell lung carcinoma or small cell lung carcinoma, melanoma, lobular or ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma or adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, or leukemia. In a further embodiment, an antibody or a functional thereof has a binding affinity within about 1-5000 fold of the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells. In the foregoing embodiments binding affinity can be 1-5000 fold greater or less than the binding affinity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

Binding affinity can be determined by association ($K_a$) and dissociation ($K_d$) rate. Equilibrium affinity constant, K, is the ratio of $K_a/K_d$. Association ($K_a$) and dissociation ($K_d$) rates can be measured using surface plasmon resonance (SPR) (Rich and Myszka, *Curr. Opin. Biotechnol.* 11:54 (2000); Englebienne, *Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)).

Additional specific non-limiting antibodies and functional fragments have binding affinity for a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 within about $K_d$ $10^{-2}$ M to about $K_d$ $10^{-15}$ M, or within about $K_d$ $10^{-6}$ M to about $K_d$ $10^{-12}$ M. In particular embodiments, binding affinity for is less than $5 \times 10^{-2}$ M, $10^{0.2}$ M, $5 \times 10^{-3}$ M, $10^{-3}$ M $5 \times 10^{-4}$ M, $10^{-4}$ M $5 \times 10^{-5}$ M, $10^{-5}$ M $5 \times 10^{-6}$ M, $10^{-6}$ M $5 \times 10^{-7}$ M, $10^{-7}$ M $5 \times 10^{-8}$ M, $10^{-8}$ M $5 \times 10^{-9}$ M, $10^{-9}$ M $5 \times 10^{-10}$ M, $10^{-10}$ M $5 \times 10^{-11}$ M, $5 \times 10^{-12}$ M, $10^{-12}$ M $5 \times 10^{-13}$ M, $10^{-13}$ M $5 \times 10^{-14}$ M, $10^{14}$ M $5 \times 10^{-15}$ M, and $10^{15}$ M. In particular embodiments, an antibody or functional fragment has a binding affinity within about $K_d$ $10^{-5}$ M to about $K_d$ $10^{-13}$ M for binding to an antigen (e.g., NONO/nmt55), or to a neoplastic, cancer, tumor or metastatic cell. In additional particular embodiments, an antibody or functional fragment has a binding affinity within about $K_d$ $10^{-5}$ M to about $K_d$ $10^{-13}$ M for binding to a stomach adenocarcinoma (e.g., diffuse or intestinal), colorectal cancer such as adenocarcinoma, ovarian carcinoma, lung cancer, such as a lung adenocarcinoma, squamous cell lung carcinoma or small cell lung carcinoma, melanoma, lobular or ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma or adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell or adenocarcinoma, uterine cancer such as adenocarcinoma, Hodgkin's disease, lymphoma, or leukemia. In further particular embodiments, an antibody or functional fragment has a binding affinity within about $K_d$ $10^{-5}$ M to about $K_d$ $10^{-13}$ M for binding to lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

Antibodies and functional fragments that bind to a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, or that compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or to an antigen (e.g., NONO/nmt55), can have greater or less relative cell proliferation inhibiting or reducing activity, or greater or less relative cell apoptosis inducing or stimulating activity than LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. Antibodies and functional fragments of the invention therefore include those that bind to a cell or an antigen (e.g., NONO/nmt55) to which LM-1 antibody, or compete with LM-1 antibody for binding to a cell or an antigen (e.g., NONO/nmt55), and have greater or less relative cell proliferation inhibiting or reducing activity, or greater or less relative cell apoptosis inducing or stimulating activity than LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

Invention antibodies therefore include those that have a sequence distinct from LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 but that retain one or more activities or functions, at least in part, of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. Exemplary activities and functions include, for example, binding to a cell to which LM-1 antibody binds; binding to an antigen (e.g., NONO/nmt55) to which LM-1 antibody binds; competing with LM-1 antibody for binding to a cell or to an antigen (e.g., NONO/nmt55); inhibiting or reducing cell growth or proliferation, or stimulating or inducing cell death, lysis or apoptosis (e.g., a neoplastic, tumor or cancer, or metastasis cell); binding to one or more of a stomach adenocarcinoma (e.g., diffuse or intestinal), colorectal cancer such as adenocarcinoma, ovarian carcinoma, lung cancer, such as a lung adenocarcinoma, squamous cell lung carcinoma and small cell lung carcinoma, melanoma, lobular and ductal mammary carcinoma, breast cancer such as invasive ductal or lobular cancer, gastric cancer, pancreatic cancer such as pancreatic adenocarcinoma (e.g., ductal), sarcoma, gastrointestinal cancer such as a stomach cancer, nervous tissue or brain tumor such as a glioma, esophageal cancer such as esophagial squamous cell carcinoma and adenocarcinoma, osteosarcoma, fibrosarcoma, urinary bladder cancer, prostate cancer such as prostate adenocarcinoma, kidney cancer such as renal carcinoma, ovarian cancer such as adenocarcinoma, testicular cancer, endometrial cancer, cervical cancer such as squamous cell and adenocarcinoma, uterine cancer such as adenocarcinoma, Hodgkin's disease, lymphoma, and leukemia; inhibiting lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cell growth or proliferation, or stimulating or inducing lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cell death, lysis or apoptosis, etc.

Thus, in accordance with the invention there are also provided modified antibodies and functional fragments provided that the modified form retains, at least a part of an activity or function of unmodified or reference antibody, or functional fragment. In one embodiment, an antibody or a functional fragment thereof includes a heavy or a light chain variable region sequence with one or more amino acid additions, deletions or substitutions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 provided said antibody or functional fragment retains at least partial activity or function of intact full length LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In one aspect, an antibody or a functional fragment with one or more amino acid additions, deletions or substitutions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 competes for binding to a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In another aspect, an antibody or a functional fragment with one or more amino acid deletions, substitutions or additions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds to a cell or an antigen (e.g., NONO/nmt55) to which LM-1 antibody binds. In an additional aspect, an antibody or a functional fragment with one or more amino acid deletions, substitutions or additions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 inhibits or reduces proliferation of a cell in which LM-1 antibody inhibits or reduces proliferation. In a further aspect, an antibody or a functional fragment with one or more amino acid deletions, substitutions or additions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 stimulates or induces death, lysis or apoptosis of a cell in which LM-1 antibody stimulates or induces death, lysis or apoptosis. In still further particular aspects, cell growth or proliferation is inhibited, decreased or reduced at least 20%, 30%, 40%, 50%, 60%, 75%, or more relative to a control (untreated) cell, or any numerical value or range within or encompassing such percent values. In yet further particular aspects, cell death, lysis or apoptosis is at least 20%, 30%, 40%, 50%, 60%, 75%, or more relative to a control (untreated) cell, or any numerical value or range within or encompassing such percent values.

As used herein, the term "modify" and grammatical variations thereof, means that the composition deviates from a reference composition. Such modified proteins, nucleic acids and other compositions may have greater or less activity than or a distinct function from a reference unmodified protein, nucleic acid, or composition.

Modifications, which include substitutions, additions and deletions, can also be referred to as "variants." Specific non-limiting examples of amino acid variants include LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 fragments and subsequences. Exemplary LM-1 antibody subsequences and fragments include a portion of the LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 that at least partially competes with LM-1 antibody for binding to a cell or an antigen (e.g., NONO/nmt55), or that retains at least partial binding activity to a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, or that retains an ability to inhibit or reduce proliferation of a cell in which LM-1 antibody inhibits or reduces proliferation, or that retains an ability to stimulate or induce death, lysis or apoptosis of a cell in which LM-1 antibody stimulates or induces death, lysis or apoptosis.

As used herein, the term "fragment" or "subsequence" means a portion of the full length molecule. Thus, a fragment or subsequence of an antibody has one or more less amino acids than a full length intact reference antibody (e.g. one or more internal or terminal amino acid deletions from either amino or carboxy-termini of heavy or light chain variable or constant regions). A nucleic acid fragment has at least one less nucleotide than a full length comparison nucleic acid sequence. Fragments therefore can be any length up to the full length native molecule.

The terms "functional fragment" and "functional subsequence" when referring to an antibody refers to a portion of an antibody with a function or activity. For example, a functional fragment can retain one or more partial functions or activities as an intact reference antibody, e.g., a function or activity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. For example, a LM-1 antibody subsequence that competes for binding of full length intact LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 to a cell or to an antigen (e.g., NONO/nmt55), or that binds to a cell or an antigen (e.g., NONO/nmt55) to which full length intact LM-1 antibody binds is considered a functional subsequence.

Antibody fragments, including single-chain antibodies, can include all or a portion of heavy or light chain variable region(s) (e.g., one or more CDRs, such as CDR1, CDR2 or CDR3, respectively amino acids 24-35, 52-67, or 100-118 of SEQ ID NO: 1, 3, 5, 7 or 9, and amino acids 23-35, 51-58 or 90-101 of SEQ ID NO:11) alone or in combination with all or a portion of one or more of the following: hinge region, CH1, CH2, and CH3 domains. Also included are antigen-binding subsequences of any combination of heavy or light chain variable region(s) (e.g., one or more CDRs, such as CDR1, CDR2 or CDR3, respectively amino acids 24-35, 52-67, or 100-118 of SEQ ID NO: 1, 3, 5, 7 or 9, and amino acids 23-35, 51-58 or 90-101 of SEQ ID NO:11) with a hinge region, CH1, CH2, and CH3 domains.

Exemplary antibody subsequences and fragments of the invention include Fab, Fab', F(ab')$_2$, Fv, Fd, single-chain Fv (scFv), disulfide-linked Fvs (sdFv), $V_L$, $V_H$, trispecific (Fab$_3$), bispecific (Fab$_2$), diabody (($V_L$-$V_H$)$_2$ or ($V_H$-$V_L$)$_2$), triabody (trivalent), tetrabody (tetravalent), minibody ((scF$_V$-C$_H$3)$_2$), bispecific single-chain Fv (Bis-scFv), IgGdeltaCH2, scFv-Fc and (scFv)$_2$-Fc. Such subsequences and fragments can have binding affinity as the full length antibody, the binding specificity as the full length antibody, or one or more activities or functions of as a full length antibody, e.g., a function or activity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

Antibody subsequences and fragments can be combined. For example, a $V_L$ or $V_H$ subsequences can be joined by a linker sequence thereby forming a $V_L$-$V_H$ chimera. In particular, a heavy chain variable sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, can be combined with a light chain variable sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. The invention therefore provides: 1) heavy chain variable sequence of LM-1 antibody, as represented by antibody produced by a cell line DSMZ Deposit No. DSM ACC 2623, or represented by heavy chain variable sequence set forth as SEQ ID NO: 1, 3, 5, 7 or 9) light chain variable sequence of LM-1 antibody, as represented by antibody produced by a cell line DSMZ Deposit No. DSM ACC 2623, or represented by light chain variable sequence set forth as SEQ ID NO:9 alone and in combination with each other. A combination of single-chain Fvs (scFv) subsequences can be joined by a linker sequence thereby forming a scFv-scFv chimera. Antibody subsequences and fragments include single-chain antibodies or variable region(s) alone or in combination with all or a portion of other subsequences.

Modified proteins further include amino acid substitutions. Substitutions can be conservative or non-conservative and may be in a constant or variable (e.g., hypervariable, such as CDR or FR) region of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In particular embodiments, a modified LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 has one or a few conservative or non-conservative amino acid substitutions.

Antibody structural determinants that contribute to antigen binding, such as complementarity determining regions (CDR, of which there are three in each heavy and light chain sequence, conveniently denoted as HC-CDR1, HC-CDR2 and HC-CDR3; and LC-CDR1, LC-CDR2 and LC-CDR3; respectively amino acids 24-35, 52-67 or 100-118 of SEQ ID NO:1, 3, 5, 7 or 9, and amino acids 23-35, 51-58 or 90-101 of SEQ ID NO:11) within hypervariable regions are known to the skilled artisan. The location of additional regions, such as D- and J-regions are also known to the skilled artisan. Antibodies and subsequences thereof in which one or more CDR sequences have sufficient sequence identity to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 so as to retain at least partial function or activity of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 e.g., cell or antigen (e.g., NONO/nmt55) binding, binding affinity (e.g., $K_d$), cell proliferation inhibition, or stimulating or inducing cell apoptosis, etc.

Accordingly, amino acid substitutions in constant or variable regions of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 are likely to be tolerated. One, a few or several substitutions in a variable region outside of a CDR of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 is also likely to be tolerated at least to the extent that at least partial cell or antigen binding activity is retained, or partial cell proliferation inhibiting or apoptosis stimulating or inducing activity is retained. One or a few conservative substitutions in a CDR of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67 or 100-118 of SEQ ID NO: 1, 3, 5, 7 or 9, and amino acids 23-35, 51-58 or 90-101 of SEQ ID NO:11), is also likely to be tolerated at least to the extent that at least partial cell or antigen (e.g., NONO/nmt55) binding activity is retained (i.e., cell or antigen binding is not destroyed), or partial cell proliferation inhibiting or apoptosis stimulating or inducing activity is retained. Non-conservative substitution of many amino acids in hypervariable regions (e.g., CDRs) of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 is likely to affect one or more of cell or antigen (e.g., NONO/nmt55) binding activity, binding affinity (e.g., $K_d$), or antibody function or activity, such as cell proliferation inhibition, stimulating or inducing cell apoptosis, etc.

A "conservative substitution" is the replacement of one amino acid by a biologically, chemically or structurally similar residue. Biologically similar means that the substitution does not destroy a biological activity, e.g., cell binding or cell proliferation inhibiting or apoptosis inducing or stimulating activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

In particular embodiments, a heavy or light chain hypervariable region sequence or a region therein, such as a CDR (CDR1, CDR2 or CDR3; amino acids 24-35, 52-67 or 100-118 of SEQ ID NO: 1, 3, 5, 7 or 9, or amino acids 23-35, 51-58 or 90-101 of SEQ ID NO:11) or FR will have 1-10, 1-5, 1-3 or fewer (e.g., 1 or 2) amino acid substitutions. In an additional embodiment, an amino acid substitution within a heavy or light chain hypervariable region sequence is not within more than one CDR. In an additional embodiment, a substitution within a heavy or light chain hypervariable region sequence is not within a CDR. In another embodiment, a substitution within a hypervariable region sequence is not within an FR.

The effect of a given modification can be readily assayed in order to identify antibodies and functional fragments retaining at least a part of the cell or antigen (e.g., NONO/nmt55) binding activity, affinity or antibody function or activity of unmodified antibody, e.g., LM-1 antibody, produced by a cell line DSMZ Deposit No. DSM ACC 2623, or represented by heavy and light chain sequences set forth as SEQ ID NOs:1, 3, 5, 7 or 9, and 11 or 13. For example, an amino acid substitution in a variable region (e.g., within or outside of CDR1, CDR2 or CDR3) of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 can be assayed for cell or antigen (e.g., NONO/nmt55) binding, cell proliferation inhibiting or reducing activity, inducing or stimulating cell death, lysis or apoptosis, etc.

Regional mutability analysis can be used to predict the effect of particular substitutions in complementarity determining regions (CDR) and framework regions (FR) (Shapiro et al., *J Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon OSAR can in turn be used to predict the effect of substitutions (mutations). For example, the effect of mutations on the association and dissociation rate of an antibody interacting with its antigen has been used to construct quantitative predictive models for both kinetic ($K_a$ and $K_d$) constants, which in turn is used to predict the effect of other mutations on the antibody (De Genst et al., *J Biol Chem.* 277:29897 (2002)). The skilled artisan can therefore use such analysis to identify amino acid substitutions of antibodies and functional fragments that are likely to result in an antibody or functional fragment that retains at least partial activity or function of non-substituted antibody or functional fragment.

Another method for identifying residues or regions for mutagenesis is called "alanine scanning mutagenesis" which is described, for example, by Cunningham and Wells (*Science* 244:1081 (1989)). A residue or group of target residues are identified (e.g., charged residues such as arg, asp, his, lys, and glu) and replaced by a neutral or negatively charged amino acid (most desirably alanine or polyalanine) to affect the interaction of the amino acids with the surrounding aqueous environment in or outside the cell. The domains demonstrating functional sensitivity to the substitutions then are refined by introducing further or other variants at or for the sites of substitution. Thus, while the site for introducing an amino acid sequence variation is predetermined, the mutation need not be predetermined. For instance, to optimize the performance of a mutation at a given site, alanine scanning or random mutagenesis may be conducted at the target codon or region and the expressed variants are screened for antigen or cell binding, or the ability to induce apoptosis or inhibit proliferation of a neoplastic, tumor, cancer or metastatic cell.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications also include structural and functional analogues, for example, peptidomimetics having synthetic or non-natural amino acids or amino acid analogues and derivatized forms.

Modified forms further include derivatized sequences, for example, amino acids in which free amino groups form amine hydrochlorides, p-toluene sulfonyl groups, carbobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using methods known in the art (e.g., PCR based site-directed, deletion and insertion mutagenesis, chemical modification and mutagenesis, cross-linking, etc.).

Modified forms include additions and insertions. For example, an addition can be the covalent or non-covalent attachment of any type of molecule to a protein (e.g., antibody), nucleic acid or other composition. Typically additions and insertions confer a distinct function or activity.

Additions and insertions include fusion (chimeric) polypeptide or nucleic acid sequences, which is a sequence having one or more molecules not normally present in a reference native (wild type) sequence covalently attached to the sequence. A particular example is an amino acid sequence of another protein (e.g., antibody) to produce a multifunctional protein (e.g., multispecific antibody).

In accordance with the invention, there are provided antibodies, nucleic acids, and other compositions that include a heterologous domain. Thus, a heterologous domain can consist of any of a variety of different types of small or large functional moieties. Such moieties include nucleic acid, peptide, carbohydrate, lipid or small organic compounds, such as a drug (e.g., a cell anti-proliferative agent), metals (gold, silver), etc. A heterologous domain can be an amino acid addition or insertion.

Particular non-limiting examples of heterologous domains include, for example, tags, detectable labels and cytotoxic agents. Specific examples of tags and detectable labels include enzymes (horseradish peroxidase, urease, catalase, alkaline phosphatase, beta-galactosidase, chloramphenicol transferase); enzyme substrates; ligands (e.g., biotin); receptors (avidin); radionuclides (e.g., $C^{14}$, $S^{35}$, $P^{32}$, $P^{33}$, $H^3$, $I^{125}$, $I^{131}$, gallium-67 and 68, scantium-47, indium-111, radium-223); T7-, His-, myc-, HA- and FLAG-tags; electron-dense reagents; energy transfer molecules; paramagnetic labels; fluorophores (fluorescein, fluorscamine, rhodamine, phycoerthrin, phycocyanin, allophycocyanin); chromophores; chemi-luminescent (imidazole, luciferase, acridinium, oxalate); and bio-luminescent agents. Specific examples of cytotoxic agents (cytotoxins) include diptheria, toxin, cholera toxin and ricin.

Additional examples of heterologous domains include, for example, anti-cell proliferative agents (e.g., anti-neoplastic, anti-tumor or anti-cancer, or anti-metastasis agents). Specific non-limiting examples of anti-cell proliferative agents (e.g., anti-neoplastic, anti-tumor or anti-cancer, or anti-metastasis agents, cytotoxins, etc.) are disclosed herein and known in the art.

Linker sequences may be inserted between the protein (e.g., antibody), nucleic acid, or other composition and the addition or insertion (e.g., heterologous domain) so that the two entities maintain, at least in part, a distinct function or activity. Linker sequences may have one or more properties that include a flexible structure, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary (see, e.g., U.S. Pat. No. 6,087,329). Linkers further include chemical cross-linking and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Further examples of additions include glycosylation, fatty acids, lipids, acetylation, phosphorylation, amidation, formylation, ubiquitinatation, and derivatization by protecting/blocking groups and any of numerous chemical modifications. Other permutations and possibilities will be readily apparent to those of ordinary skill in the art, and are considered to be within the scope of the invention.

The term "isolated" used as a modifier of a composition means that the composition is made by the hand of man or is separated from one or more other components in their naturally occurring in vivo environment. Generally, compositions so separated are substantially free of one or more materials with which they normally associate with in nature, for example, one or more protein, nucleic acid, lipid, carbohydrate, cell membrane. Thus, an isolated composition is substantially separated from other biological components in the cell of the organism in which the composition naturally occurs, or from the artificial medium in which it is produced (e.g., synthetically or through cell culture). For example, an isolated polypeptide is substantially separated from other polypeptides and nucleic acid and does not include a library of polypeptides or polynucleotides present among millions of polypeptide or nucleic acid sequences, such as a polypeptide, genomic or cDNA library, for example. An isolated nucleic acid is substantially separated from other polypeptides and nucleic acid and does not include a library of polypeptides or polynucleotides present among millions of polypeptide or nucleic acid sequences, such as a polypeptide, genomic or cDNA library, for example. The term "isolated" does not exclude alternative physical forms of the composition, for example, an isolated protein could include protein multimers, post-translational modifications (e.g., glycosylation, phosphorylation) or derivatized forms.

The term "purified" used as a modifier of a composition refers to a composition free of most or all of the materials with which it typically associates with in nature. Thus, a protein separated from cells is considered to be substantially purified when separated from cellular components by standard methods while a chemically synthesized nucleic acid sequence is considered to be substantially purified when separated from its chemical precursors. Purified therefore does not require absolute purity. Furthermore, a "purified" composition can be combined with one or more other molecules. Thus, the term "purified" does not exclude combinations of compositions.

"Purified" proteins and nucleic acid include proteins and nucleic acids produced by standard purification methods. The term also includes proteins and nucleic acids produced by recombinant expression in a host cell as well as chemical synthesis. "Purified" can also refer to a composition in which the level of contaminants is below a level that is acceptable to a regulatory agency for administration to a human or non-human animal, for example, the Food and Drug administration (FDA).

Substantial purity can be at least about 60% or more of the molecule by mass. Purity can also be about 70% or 80% or more, and can be greater, for example, 90% or more. Purity can be less, for example, in a pharmaceutical carrier the amount of a molecule by weight % can be less than 60% but the relative proportion of the molecule compared to other components with which it is normally associated with will be greater. Purity can be determined by any appropriate method, including, for example, UV spectroscopy, chromatography (e.g., HPLC, gas phase), gel electrophoresis (e.g., silver or coomassie staining) and sequence analysis (peptide and nucleic acid).

Methods of producing polyclonal and monoclonal antibodies are known in the art. For example, LM-1 antigen (e.g., NONO/nmt55) or an immunogenic fragment thereof, optionally conjugated to a carrier such as keyhole limpet hemocyanin (KLH) or ovalbumin (e.g., BSA), or mixed with an adjuvant such as Freund's complete or incomplete adjuvant, and used to immunize an animal. Using conventional hybridoma technology, splenocytes from immunized animals that respond to LM-1 antigen (e.g., NONO/nmt55) can be isolated and fused with myeloma cells. Monoclonal antibodies produced by the hybridomas can be screened for reactivity with LM-1 antigen (e.g., NONO/nmt55), for example, via ELISA. Additional non-limiting particular methods of antibody and functional fragment screening and selection include phage display, protein-mRNA link via ribosome and mRNA display, display on yeast, bacteria, mammalian cells or retroviruses, microbead via in vitro compartmentalization, protein-DNA display, growth selection via yeast 2-hybrid, protein fragment complementation (Hoogenboom, R., *Nature Biotechnol.* 23:1105 (2005)).

Antibodies that compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or antigen (e.g., NONO/nmt55) can be screened and identified using a conventional competition binding assays. Screened antibodies are selected based upon an ability to compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding to a cell or an antigen (e.g., NONO/nmt55). The ability of an antibody to compete with LM-1 antibody for binding to a cell or an antigen (e.g., NONO/nmt55), or to inhibit, prevent or block binding of LM-1 antibody to a cell or an antigen (e.g., NONO/nmt55), can be determined by various assays know in the art, including enzyme linked immunosorbent assay (ELISA).

Proteins and antibodies, subsequences and fragments thereof, as well as other modified sequences can be produced by genetic methodology. Such techniques include expression of all or a part of the gene encoding the protein or antibody into a host cell such as Cos cells or *E. coli*. Such host cells can express full length or a fragment, for example, an scFv (see, e.g., Whitlow et al., In: *Methods: A Companion to Methods in Enzymology* 2:97 (1991), Bird et al., *Science* 242:423 (1988); and U.S. Pat. No. 4,946,778). Antibodies and functional fragments, and nucleic acid sequences can also be produced by chemical synthesis using methods known to the skilled artisan, for example, an automated peptide synthesis apparatus (see, e.g., Applied Biosystems, Foster City, Calif.).

Cells or antigen (e.g., NONO/nmt55) suitable for generating antibodies can be produced by any of a variety of standard protein purification or recombinant expression techniques known in the art. For example, LM-1 antigen (e.g., NONO/nmt55) can be transfected into cells, including bacteria or eukaryotic cells (e.g., yeast). Lm-1 is also present on cells, such as Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells. Accordingly, recombinant LM-1 antigen (e.g., NONO/nmt55), whole cells, or cell preparations, cell extracts or fractions of such cells can be used to immunize animals in order to produce antibodies that compete with LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 for binding of to a cell or antigen (e.g., NONO/nmt55), or that bind to a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, for example.

Animals that may be immunized include mice, rats, rabbits, goats, sheep, cows or steer, guinea pigs or primates. Initial and any optional subsequent immunization may be through intravenous, intraperitoneal, intramuscular, or subcutaneous routes. Subsequent immunizations may be at the same or at different concentrations of LM-1 antigen (e.g., NONO/nmt55) preparation, and may be at regular or irregular intervals.

Animals include those genetically modified to include human IgG gene loci, which can therefore be used to produce human antibodies. Transgenic animals with one or more human immunoglobulin genes that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13:65 (1995)).

Antibodies can also be generated using other techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988).

Antibody subsequences and fragments can be prepared by proteolytic hydrolysis of the antibody, for example, by pepsin or papain digestion of whole antibodies. Antibody subsequences and fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enzymol.* 1:422 (1967)). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988). Other methods of cleaving antibodies, such as separation of heavy chains to form monovalent light-heavy chain fragments, further cleavage of fragments, or other enzymatic or chemical may also be used.

Modified antibodies and functional fragments having altered characteristics, such as increased binding affinity, can be produced using methods known to the skilled artisan art. For example, affinity maturation techniques can be used to improve antibody binding affinity (US 2004/0162413 A1; U.S. Pat. Nos. 6,656,467, 6,531,580, 6,590,079 and 5,955,358; Fiedler et al., *Protein Eng.* 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to produce humanized antibodies (Carter et al., *Proc. Natl. Acad. Sci. USA* 89:4285 (1992); and Presta et al., *J. Immunol.* 151:2600 (1993)).

Methods for producing chimeric antibodies are known in the art (e.g., Morrison, *Science* 229:1202 (1985); Oi et al., *BioTechniques* 4:214 (1986); Gillies et al., *J. Immunol.*

Methods 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Suitable techniques that additionally may be employed in antibody methods include affinity purification, non-denaturing gel purification, HPLC or RP-HPLC, size exclusion, purification on protein A column, or any combination of these techniques. The antibody isotype can be determined using an ELISA assay, for example, a human Ig can be identified using mouse Ig-absorbed anti-human Ig.

In accordance with the invention, further provided are methods of producing antibodies and functional fragments. In one embodiment, a method includes administering a LM-1 antigen (e.g., NONO/nmt55), or cell expressing a LM-1 antigen (e.g., NONO/nmt55), to an animal, screening the animal for expression of an antibody that binds to the LM-1 antigen (e.g., NONO/nmt55) or cell expressing a LM-1 antigen (e.g., NONO/nmt55), selecting an animal that produces an antibody that binds to LM-1 antigen (e.g., NONO/nmt55) or cell expressing a LM-1 antigen (e.g., NONO/nmt55), and isolating the antibody from the selected animal. In another embodiment, a method includes administering LM-1 antigen (e.g., NONO/nmt55) or cell expressing a LM-1 antigen (e.g., NONO/nmt55) to an animal capable of expressing a human immunoglobulin; isolating spleen cells from an animal that produces antibody that binds to the LM-1 antigen (e.g., NONO/nmt55) or cell expressing a LM-1 antigen (e.g., NONO/nmt55), fusing the spleen cells with a myeloma cell to produce a hybridoma, and screening the hybridoma for expression of an antibody that binds to LM-1 antigen (e.g., NONO/nmt55) or cell expressing an LM-1 antigen (e.g., NONO/nmt55).

In accordance with the invention, there are provided host cells that express antibodies and functional fragments of the antibodies as set forth herein. In particular embodiments, host cells are purified or isolated, and optionally have not been transformed with a nucleic acid that encodes the expressed antibody or functional fragment. In additional embodiments, a host cell expresses an antibody or functional fragment that includes a heavy or light chain sequence with 50%, 60%, 70%, 75%, 80%, 85%, 90%, 95%, 96%, 97%, 98%, or more sequence identity to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In further embodiments, a host cell expresses a heavy or light chain sequence with at least 80-85%, 85-90%, 90-95%, 95-100% identity to one or more CDRs in heavy chain variable region sequence or light chain variable region sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 (e.g., amino acids 24-35, 52-67 or 100-118 of SEQ ID NO: 1, 3, 5, 7 or 9, and amino acids 23-35, 51-58 or 90-101 of SEQ ID NO:11).

In accordance with the invention, there are provided isolated and purified nucleic acids. Nucleic acids of the invention include, among other things, nucleic acid sequences 1) encoding antibodies and functional fragments that are structurally or functionally related to LM-1 antibody, produced by a cell line DSMZ Deposit No. DSM ACC as represented by antibody, or represented by heavy and light chain sequences set forth as SEQ ID NOs: 1, 3, 5, 7 or 9, and 11 or 13; 2) encode LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or antibodies and functional fragments that include all or a portion of a sequence of SEQ ID NOs:1, 3, 5, 7 or 9, and 11 or 13 (e.g., one or more CDRs, amino acids 24-35, 52-67 or 100-118 of SEQ ID NO: 1, 3, 5, 7 or 9, or amino acids 23-35, 51-58 or 90-101 of SEQ ID NO:11) that exhibit a degree of complementarity or identity with nucleic acid sequences encoding antibodies and functional fragments with sequence identity to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13; and 4) that hybridize to sequences encoding antibodies and functional fragments that have sequence identity to LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

In particular embodiments, a nucleic acid sequence encodes a heavy or light chain sequence of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or a functional fragment thereof. In another embodiment, a nucleic acid sequence is 75-100% complementary or identical to a nucleic acid sequence that encodes SEQ ID NO:1, 3, 5, 7 or 9, and 11 or 13. In a further embodiment, a nucleic acid sequence is 75-100% complementary or identical to a nucleic acid sequence that encodes SEQ ID NO:9.

Proteins, such as antibodies that include amino acid substitutions, additions or deletions can be encoded by a nucleic acid. Consequently, nucleic acid sequences encoding proteins that include amino acid substitutions, additions or deletions are also provided.

The terms "nucleic acid" and "polynucleotide" and the like refer to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. Exemplary nucleic acids include but are not limited to: RNA, DNA, cDNA, genomic nucleic acid, naturally occurring and non naturally occurring nucleic acid, e.g., synthetic nucleic acid.

Nucleic acids can be of various lengths. Nucleic acid lengths typically range from about 20 nucleotides to 20 Kb, or any numerical value or range within or encompassing such lengths, 10 nucleotides to 10 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length, or any numerical value or range or value within or encompassing such lengths. In particular embodiments, a nucleic acid sequence has a length from about 10-20, 20-30, 30-50, 50-100, 100-150, 150-200, 200-250, 250-300, 300-400, 400-500, 500-1000, 1000-2000, nucleotides, or any numerical value or range within or encompassing such lengths. In additional embodiments, nucleic acid sequences range in length to encode any of SEQ ID NOs:1, 3, 5, 7 or 9, and 11 or 13, or a subsequence thereof, such as nucleotides 72-105, 153-201 or 300-354 of SEQ ID NO:2 and nucleotides 69-105, 153-174, or 270-303 of SEQ ID NO:12. Shorter polynucleotides are commonly referred to as "oligonucleotides" or "probes" of single- or double-stranded DNA. However, there is no upper limit to the length of such oligonucleotides.

Polynucleotides include L- or D-forms and mixtures thereof, which additionally may be modified to be resistant to degradation when administered to a subject. Particular examples include 5' and 3' linkages resistant to endonucleases and exonucleases present in various tissues or fluids of a subject.

In accordance with the invention there are provided nucleic acid sequences that hybridize to a nucleic acid that encodes all or a fragment of a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13. In one embodiment, a nucleic acid sequence specifically hybridizes to a nucleic acid encoding SEQ ID NO: 1, 3, 5, 7 or 9, or a portion thereof (e.g., nucleotides 72-105, 153-201, or 300-354 of SEQ ID NO:2). In another embodiment, a nucleic acid sequence specifically hybridizes to a nucleic acid encoding SEQ ID NO:11 or 13 or a portion thereof (e.g., nucleotide positions corresponding to the light chain variable region CDRs, 69-105, 153-174, or 270-303 of SEQ ID NO:12). In a further embodiment, a nucleic acid sequence is at least 75-100% complementary or homologous to a nucleic acid sequence that encodes all or a subsequence or fragment of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13.

The term "hybridize" and grammatical variations thereof refer to the binding between nucleic acid sequences. Hybridizing sequences will generally have more than about 50% homology (e.g., 50%, 60%, 70%, 80%, 90%, or more identity) to a reference nucleic acid or a sequence complementary to a reference sequence. Hybridizing sequences that are 100% or fully complementary to a reference sequence, for example, to a nucleic acid that encodes an amino acid sequence of a reference sequence, exhibit 100% base pairing with no mismatches. The hybridization region between hybridizing sequences typically is at least about 12-15 nucleotides, 15-20 nucleotides, 20-30 nucleotides, 30-50 nucleotides, 50-100 nucleotides, 100 to 200 nucleotides or more, or any numerical value or range within or encompassing such lengths.

In accordance with the invention, there are further provided antisense polynucleotides, small interfering RNA, and ribozyme nucleic acid. In one embodiment, an antisense polynucleotide, small interfering RNA, or ribozyme nucleic acid specifically hybridizes to a nucleic acid sequence encoding LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 or SEQ ID NO:1, 3, 5, 7 or 9, and 11 or 13 or a portion thereof, and optionally reduces expression of LM-1 antibody, as represented by antibody produced by a cell line DSMZ Deposit No. DSM ACC 2623, or represented by heavy and light chain sequences set forth as SEQ ID NOs: 1, 3, 5, 7, 9, 11 or 13. In another embodiment, an antisense polynucleotide, small interfering RNA, or ribozyme nucleic acid is at least 60% or more (e.g., 65%, 70%, 75%, 80%, 85%, 90%, 95%, etc.) complementary or homologous to a nucleic acid sequence that encodes LM-1 antibody, as represented by antibody produced by a cell line DSMZ Deposit No. DSM ACC 2623, or represented by heavy and light chain sequences set forth as SEQ ID NOs:1, 3, 5, 7, 9, 11 or 13 or a subsequence thereof (e.g., nucleotides 72-105, 153-201 and 300-354 of SEQ ID NO:2, or nucleotides 69-105, 153-174, or 270-303 of SEQ ID NO:12). Antisense polynucleotides can have a length from about 10-20, 20-30, 30-50, 50-100, 100-150, 150-200, 200-250, 250-300, 300-400, 400-500, 500-1000, 1000-2000 nucleotides, or any numerical value or range within or encompassing such lengths.

As used herein, the term "antisense" refers to a polynucleotide or peptide nucleic acid capable of binding to a specific DNA or RNA sequence. Antisense includes single, double, triple or greater stranded RNA and DNA polynucleotides and peptide nucleic acids (PNAs) that bind RNA transcript or DNA. Particular examples include RNA and DNA antisense that binds to sense RNA. For example, a single stranded nucleic acid can target a protein transcript that participates in metabolism, catabolism, removal or degradation of glycogen from a cell (e.g., mRNA). Antisense molecules are typically 95-100% complementary to the sense strand but can be "partially" complementary, in which only some of the nucleotides bind to the sense molecule (less than 100% complementary, e.g., 95%, 90%, 80%, 70% and sometimes less), or any numerical value or range within or encompassing such percent values.

Triplex forming antisense can bind to double strand DNA thereby inhibiting transcription of the gene. Oligonucleotides derived from the transcription initiation site of the gene, e.g., between positions −10 and +10 from the start site, are one particular example.

Short interfering RNA (referred to as siRNA or RNAi) for inhibiting gene expression is known in the art (see, e.g., Kennerdell et al., Cell 95:1017 (1998); Fire et al., Nature, 391:806 (1998); WO 02/44321; WO 01/68836; WO 00/44895, WO 99/32619, WO 01/75164, WO 01/92513, WO 01/29058, WO 01/89304, WO 02/16620; and WO 02/29858). RNAi silencing can be induced by a nucleic acid encoding an RNA that forms a "hairpin" structure or by expressing RNA from each end of an encoding nucleic acid, making two RNA molecules that hybridize.

Ribozymes, which are enzymatic RNA molecules that catalyze the specific cleavage of RNA can be used to inhibit expression of the encoded protein. Ribozymes form sequence-specific hybrids with complementary target RNA, which is then cleaved. Specific examples include engineered hammerhead motif ribozyme molecules that can specifically and efficiently catalyze endonucleolytic cleavage of sequences encoding a protein that participates in metabolism, catabolism, removal or degradation of glycogen, for example.

Antisense, ribozymes, RNAi and triplex forming nucleic acid are referred to collectively herein as "inhibitory nucleic acid" or "inhibitory polynucleotides." Such inhibitory nucleic acid or polynucleotides can inhibit or reduce expression of the sequence to which it binds or targets, and consequently, encoded protein as appropriate.

Inhibitory polynucleotides do not require expression control elements in order to function in vivo. Inhibitory polynucleotides can be absorbed by the cell or enter the cell via passive diffusion. Inhibitory polynucleotides can optionally be introduced into a cell using a vector. Inhibitory polynucleotides may be encoded by a nucleic acid so that it is transcribed. Furthermore, a nucleic acid encoding an inhibitory polynucleotide may be operatively linked to an expression control element for sustained or increased expression of the encoded antisense in cells or in vivo. Inhibitory nucleic acid can be designed based upon protein and nucleic acid sequences disclosed herein or available in the database.

Nucleic acid sequences further include nucleotide and nucleoside substitutions, additions and deletions, as well as derivatized forms and fusion/chimeric sequences (e.g., encoding recombinant polypeptide). For example, due to the degeneracy of the genetic code, nucleic acids include sequences and subsequences degenerate with respect to nucleic acids that encode, modified forms and variants thereof. Other examples are nucleic acids complementary to a sequence that encodes Nucleic acid deletions (subsequences and fragments) can have from about 10 to 25, 25 to 50 or 50 to 100 nucleotides. Such nucleic acids are useful for expressing polypeptide subsequences, for genetic manipulation (as primers and templates for PCR amplification), and as probes to detect the presence or an amount of a sequence encoding a protein (e.g., via hybridization), in a cell, culture medium, biological sample (e.g., tissue, organ, blood or serum), or in a subject.

Nucleic acids can be produced using various standard cloning and chemical synthesis techniques. Techniques include, but are not limited to nucleic acid amplification, e.g., polymerase chain reaction (PCR), with genomic DNA or cDNA targets using primers (e.g., a degenerate primer mixture) capable of annealing to antibody encoding sequence. Nucleic acids can also be produced by chemical synthesis (e.g., solid phase phosphoramidite synthesis) or transcription from a gene. The sequences produced can then be translated in vitro, or cloned into a plasmid and propagated and then expressed in a cell (e.g., a host cell such as yeast or bacteria, a eukaryote such as an animal or mammalian cell or in a plant).

In accordance with the invention, there are further provided vectors that comprise nucleic acid sequences of the invention. In one embodiment, a vector includes a nucleic acid sequence encoding an antibody or functional fragment as set forth herein. In another embodiment, a vector includes a nucleic acid sequence encoding Vectors include viral, prokaryotic (bacterial) and eukaryotic (plant, fungal, mammalian) vectors. Vectors can be used for expression of nucleic acids in vitro or in vivo. Such vectors, referred to as "expression vectors," are useful for introducing nucleic acids, including nucleic acids that encode LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 subsequences and fragments thereof, nucleic acids that encode modified forms or variants of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 nucleic acids that encode inhibitory nucleic acid, and expressing the encoded protein or inhibitory nucleic acid (e.g., in solution or in solid phase), in cells or in a subject in vivo.

Vectors can also be used for manipulation of nucleic acids. For genetic manipulation "cloning vectors" can be employed, and to transcribe or translate the inserted nucleic acid.

A vector generally contains an origin of replication for propagation in a cell in vitro or in vivo. Control elements, including expression control elements, present within a vector, can be included to facilitate transcription and translation, as appropriate.

Vectors can include a selection marker. A "selection marker" is a gene that allows for the selection of cells containing the gene. "Positive selection" refers to a process in which cells that contain the selection marker survive upon exposure to the positive selection. Drug resistance is one example of a positive selection marker-cells containing the marker will survive in culture medium containing the selection drug, and cells lacking the marker will die. Selection markers include drug resistance genes such as neo, which confers resistance to G418; hygr, which confers resistance to hygromycin; and puro, which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process in which cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

Viral vectors include those based upon retroviral (lentivirus for infecting dividing as well as non-dividing cells), foamy viruses (U.S. Pat. Nos. 5,624,820, 5,693,508, 5,665,577, 6,013,516 and 5,674,703; WO92/05266 and WO92/14829), adenovirus (U.S. Pat. Nos. 5,700,470, 5,731,172 and 5,928,944), adeno-associated virus (AAV) (U.S. Pat. No. 5,604,090), herpes simplex virus vectors (U.S. Pat. No. 5,501,979), cytomegalovirus (CMV) based vectors (U.S. Pat. No. 5,561,063), reovirus, rotavirus genomes, simian virus 40 (SV40) or papilloma virus (Cone et al., Proc. Natl. Acad. Sci. USA 81:6349 (1984); *Eukaryotic Viral Vectors*, Cold Spring Harbor Laboratory, Gluzman ed., 1982; Sarver et al., Mol. Cell. Biol. 1:486 (1981); U.S. Pat. No. 5,719,054). Adenovirus efficiently infects slowly replicating and/or terminally differentiated cells and can be used to target slowly replicating and/or terminally differentiated cells. Additional viral vectors useful for expression include parvovirus, Norwalk virus, coronaviruses, paramyxo- and rhabdoviruses, togavirus (e.g., sindbis virus and semliki forest virus) and vesicular stomatitis virus (VSV).

A nucleic acid can be expressed when the nucleic acid is operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

The term "expression control element" refers to nucleic acid that influences expression of an operably linked nucleic acid. Promoters and enhancers are particular non-limiting examples of expression control elements. A "promoter sequence" is a DNA regulatory region capable of initiating transcription of a downstream (3' direction) sequence. The promoter sequence includes nucleotides that facilitate transcription initiation. Enhancers also regulate gene expression, but can function at a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of interest, and stop codons.

Expression control elements include "constitutive" elements in which transcription of an operably linked nucleic acid occurs without the presence of a signal or stimuli. Expression control elements that confer expression in response to a signal or stimuli, which either increase or decrease expression of operably linked nucleic acid, are "regulatable." A regulatable element that increases expression of operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically more active in specific cell or tissue types because they are recognized by transcriptional activator proteins, or other transcription regulators active in the specific cell or tissue type, as compared to other cell or tissue types.

Tissue-specific expression control elements include promoters and enhancers active in hyperproliferative cells, such as cell proliferative disorders including neoplasias, tumors and cancers, and metastasis. Particular non-limiting examples of such promoters are hexokinase II, COX-2, alpha-fetoprotein, carcinoembryonic antigen, DE3/MUC1, prostate specific antigen, C-erB2/neu, telomerase reverse transcriptase and hypoxia-responsive promoter.

For bacterial expression, constitutive promoters include T7, as well as inducible promoters such as pL of bacteriophage λ, plac, ptrp, ptac (ptrp-lac hybrid promoter). In insect cell systems, constitutive or inducible promoters (e.g., ecdysone) may be used. In yeast, constitutive promoters include, for example, ADH or LEU2 and inducible promoters such as GAL (see, e.g., Ausubel et al., In: *Current Protocols in Molecular Biology*, Vol. 2, Ch. 13, ed., Greene Publish. Assoc. & Wiley Interscience, 1988; Grant et al., In: *Methods in Enzymology*, 153:516-544 (1987), eds. Wu & Grossman, 1987, Acad. Press, N.Y.; Glover, *DNA Cloning*, Vol. II, Ch. 3, IRL Press, Wash., D.C., 1986; Bitter, In: *Methods in Enzymology*, 152:673-684 (1987), eds. Berger & Kimmel, Acad. Press, N.Y.; and, Strathern et al., *The Molecular Biology of the Yeast Saccharomyces* eds. Cold Spring Harbor Press, Vols. I and II (1982)).

For mammalian expression, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; mouse mammary tumor virus LTR) are used.

In accordance with the invention, there are provided host cells transformed or transfected with nucleic acids and vectors of the invention. In one embodiment, a cell is stably or transiently transformed with a nucleic acid that encodes an antibody, a functional fragment, a heavy or light chain sequence, or a portion of a heavy or light chain sequence (e.g., a variable region, or one or more CDRs, amino acids 24-35, 52-67 or 100-118 of SEQ ID NO: 1, 3, 5, 7 or 9, or amino acids 23-35, 51-58 or 90-101 of SEQ ID NO:11). In another embodiment, a host cell is stably or transiently transformed with an antisense or inhibitory nucleic acid.

Host cells include but are not limited to prokaryotic and eukaryotic cells such as bacteria, fungi (yeast), plant, insect, and animal (e.g., mammalian, including primate and human) cells. The cells may be a primary cell isolate, cell culture (e.g., passaged, established or immortalized cell line), or part of a plurality of cells, or a tissue or organ ex vivo or in a subject (in vivo). For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression.

The term "transformed" or "transfected" when use in reference to a cell (e.g., a host cell) or organism, means a genetic change in a cell following incorporation of an exogenous molecule, for example, a protein or nucleic acid (e.g., a transgene) into the cell. Thus, a "transfected" or "transformed" cell is a cell into which, or a progeny thereof in which an exogenous molecule has been introduced by the hand of man, for example, by recombinant DNA techniques.

The nucleic acid can be stably or transiently transfected or transformed (expressed) in the cell and progeny thereof. Host cells therefore include those that stably or transiently express antibody, functional fragment or nucleic acid. The cell(s) can be propagated and the introduced antibody expressed, or nucleic acid transcribed. A progeny of a transfected or transformed cell may not be identical to the parent cell, since there may be mutations that occur during replication.

Typically, cell transfection or transformation employs a "vector," which refers to a plasmid, virus, such as a viral vector, or other vehicle known in the art that can be manipulated by insertion or incorporation of a nucleic acid.

A viral particle or vesicle can be designed to be targeted to particular cell types (e.g., hyperproliferating cells) by inclusion of a protein on the surface that binds to a target cell ligand or receptor. Alternatively, a cell type-specific promoter and/or enhancer can be included in the vector in order to express the nucleic acid in target cells. Thus, the viral particle or vesicle itself, viral vector, or a protein on the viral surface can be made to target cells for transfection or transformation in vitro, ex vivo or in vivo.

Introduction of compositions (e.g., protein and nucleic acid) into target cells (e.g., host cells) can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly (methylmethacrolate) microcapsules, respectively, or in a colloid system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells are known in the art and include, for example, phosphatidylcholine, phosphatidylserine, lipofectin and DOTAP (e.g., U.S. Pat. Nos. 4,844,904, 5,000,959, 4,863,740, and 4,975,282; and GIBCO-BRL, Gaithersburg, Md.). Piperazine based amphilic cationic lipids useful for gene therapy also are known (see, e.g., U.S. Pat. No. 5,861,397). Cationic lipid systems also are known (see, e.g., U.S. Pat. No. 5,459,127). Polymeric substances, microcapsules and colloidal dispersion systems such as liposomes are collectively referred to herein as "vesicles." Accordingly, viral and non-viral vector means of delivery into cells, tissue or organs, in vitro, in vivo and ex vivo are included.

The invention includes in vivo methods. For example, a cell such as an undesirably proliferating cell or cell proliferative disorder to which LM-1 antibody or functional fragment binds can be present in a subject, such as a mammal (e.g., a human subject). A subject having such cells, or cell surface expressed LM-1 antigen (e.g., NONO/nmt55) may therefore be treated by administering, for example, an antibody, or subsequence or fragment thereof, that binds to such cells, or by administering an antigen (e.g., NONO/nmt55).

In accordance with the invention, there are provided methods of treating undesirable cell proliferation or a cell proliferative or cellular hyperproliferative disorder in a subject. Such methods can be practiced with any of the antibodies, functional fragments, modified and variant forms set forth herein. In one embodiment, a method includes administering to a subject an amount of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 effective to treat the undesirable cell proliferation or a cell proliferative or cell hyperproliferative disorder in the subject. In another embodiment, a method includes administering to a subject an amount of an antibody that binds to an LM-1 antigen (e.g., NONO/nmt55) effective to treat the undesirable cell proliferation or a cell proliferative or cell hyperproliferative disorder in the subject.

As used herein, the terms "cell proliferative disorder" and "cellular hyperproliferative disorder" and grammatical variations thereof, when used in reference to a cell, tissue or organ, refers to any undesirable, excessive or abnormal cell, tissue or organ growth, proliferation, differentiation or survival. A hyperproliferative cell denotes a cell whose growth, proliferation, or survival is greater than desired, such as a reference normal cell, e.g., a cell that is of the same tissue or organ but is not a hyperproliferative cell, or a cell that fails to differentiate normally. Undesirable cell proliferation and hyperproliferative disorders include diseases and physiological conditions, both benign hyperplastic conditions characterized by undesirable, excessive or abnormal cell numbers, cell growth, cell proliferation, cell survival or differentiation in a subject. Specific examples of such disorders include metastatic and non-metastatic neoplasia, tumors and cancers (malignancies).

In various embodiments, a method includes administering to a subject a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55), in an amount effective to treat the cell proliferative or cellular hyperproliferative disorder in the subject. In particular aspects, the disorder is a neoplasia, tumor or metastatic or non-metastatic cancer (malignancy). In additional aspects, the disorder affects or is present in part at least in breast, lung, thyroid, head and neck, nasopharynx, nose or sinuses, brain, spine, adrenal gland, thyroid, lymph, gastrointestinal (mouth, esophagus, stomach, duodenum, ileum, jejunum (small intestine), colon, rectum), genito-urinary tract (uterus, ovary, endometrium, cervix, bladder, testicle, penis, prostate), kidney, pancreas, adrenal gland, liver, bone, bone marrow, lymph, blood, muscle, skin, or the hematopoetic system.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumor, cancer or neoplasia to other sites, locations or regions within the subject, in which the sites, locations or regions are distinct from the primary tumor or cancer.

Invention methods can be used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression. Thus, methods of the invention include, among other things, 1) reducing or inhibiting growth, proliferation, mobility or invasiveness of tumor or cancer cells that potentially or do develop metastases (e.g, disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Neoplasias, tumors and cancers include a sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In particular aspects, a neoplasia, tumor or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovarian adenocarcinoma, adenocarcinoma of the adrenal gland, adenocarcinoma of the endometrium or uterine adenocarcinoma.

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

Neoplasias, tumors and cancers can arise from a multitude of primary tumor types, including but not limited to breast, lung, thyroid, head and neck, nasopharynx, nose or sinuses, brain, spine, adrenal gland, thyroid, lymph, gastrointestinal (mouth, esophagus, stomach, duodenum, ileum, jejunum (small intestine), colon, rectum), genito-urinary tract (uterus, ovary, endometrium, cervix, bladder, testicle, penis, prostate), kidney, pancreas, adrenal gland, liver, bone, bone marrow, lymph, blood, muscle, skin, and the hematopoetic system, and may metastasize to secondary sites.

A "solid neoplasia, tumor or cancer" refers to neoplasia, tumor or cancer (e.g., metastasis) that typically aggregates together and forms a mass. Specific examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas refer to malignancies of epithelial or endocrine tissue, and include respiratory system carcinomas (lung, small cell lung), gastrointestinal system carcinomas, genitourinary system carcinomas, testicular carcinomas, breast carcinomas, prostatic carcinomas, endocrine system carcinomas, and melanomas. The term also includes carcinosarcomas, e.g., which include malignant tumors composed of carcinomatous and sarcomatous tissues. Adenocarcinoma includes a carcinoma of a glandular tissue, or in which the tumor forms a gland like structure. Melanoma refers to malignant tumors of melanocytes and other cells derived from pigment cell origin that may arise in the skin, the eye (including retina), or other regions of the body. Additional carcinomas can form from the uterine/cervix, endometrium, lung, head/neck, colon, pancreas, testes, adrenal gland, kidney, esophagus, stomach, liver and ovary.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma Specific non-limiting examples of neoplasias, tumors and cancers amenable to treatment include malignant and non-malignant neoplasias, tumors and cancers, and metastasis. In particular, a neoplasia, tumor, cancer or metastasis of any stage (e.g., stages IA, IB, HA, IIB, IIIA, IIIB or IV) or grade (e.g., grades G1, G2 or G3). Additional non-limiting examples include a stomach adenocarcinoma (e.g., diffuse or intestinal), colorectal adenocarcinoma, squamous cell lung carcinoma, lung adenocarcinoma, squamous cell carcinoma of the esophagus, adenocarcinoma of the pancreas, urothel carcinoma of the urinary bladder, renal carcinoma of the kidney, adenocarcinoma of the prostate, ductal carcinoma of the breast, lobular carcinoma of the breast, adenocarcinoma of the ovary, adenocarcinoma of the adrenal gland, adenocarcinoma of the endometrium or a uterus adenocarcinoma.

A "liquid neoplasia, tumor or cancer" refers to a neoplasia, tumor or cancer of the reticuloendothelial or hematopoetic system, such as a lymphoma, myeloma, or leukemia, or a neoplasia that is diffuse in nature. Particular examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As used herein, the terms "treat," "treating," "treatment" and grammatical variations thereof mean subjecting an individual patient to a protocol, regimen, process or remedy, in which it is desired to obtain a physiologic response or outcome in that patient. Since every treated patient may not respond to a particular treatment protocol, regimen, process or remedy, treating does not require that the desired physiologic response or outcome be achieved in each and every patient or patient population. Accordingly, a given patient or patient population may fail to respond or respond inadequately to treatment.

Methods of the invention may be practiced by any mode of administration or by any route, systemic, regional and local administration. Exemplary administration routes include intravenous, intrarterial, intradermal, intramuscular, subcutaneous, intra-pleural, transdermal (topical), transmucosal, intra-cranial, intra-spinal, intra-ocular, rectal, oral (alimentary) and mucosal.

Methods of the invention include, among other things, methods that provide a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i.e., a therapeutic benefit or a beneficial effect.

A therapeutic benefit or beneficial effect is any objective or subjective, transient, temporary, or long-term improvement in the condition or pathology, or a reduction in onset, severity, duration or frequency of an adverse symptom associated with or caused by cell proliferation or a cellular hyperproliferative disorder such as a neoplasia, tumor or cancer, or metastasis. A satisfactory clinical endpoint of a treatment method in accordance with the invention is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore be a cure, such as destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells, inhibiting or preventing an increase in neoplasia, tumor or cancer volume (e.g., stabilizing), slowing or inhibiting neoplasia, tumor or cancer progression, worsening or metastasis, stimulating, inducing or increasing neoplasia, tumor or cancer cell lysis or apoptosis or inhibiting neoplasia, tumor or cancer proliferation, growth or metastasis. An invention method may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur after cell lysis or apoptosis of the neoplasia, tumor or cancer, or metastasis.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subjects well being, such as increased energy, appetite, psychological well being, are all particular non-limiting examples of therapeutic benefit. A therapeutic benefit or improvement therefore can also include a subjective improvement in the quality of life of a treated subject.

In various embodiments, a method reduces or decreases neoplasia, tumor or cancer, or metastasis size or volume, inhibits or prevents an increase in neoplasia, tumor or cancer, metastasis size or volume, inhibits or delays neoplasia, tumor or cancer progression or worsening, stimulates neoplasia, tumor or cancer, or metastasis cell lysis or apoptosis, or inhibits, reduces, decreases or delays neoplasia, tumor or cancer proliferation or metastasis. In an additional embodiment, a method prolongs or extends lifespan of the subject. In a further embodiment, a method improves the quality of life of the subject.

Examination of a biopsied sample containing a neoplasia, tumor or cancer, or metastasis (e.g., blood or tissue sample), can establish neoplastic, tumor or cancer, or metastasis cell volume or cell numbers, and therefore whether a reduction or stabilization in mass or numbers or volume of neoplastic, tumor or cancer or metastatic cells or inhibition of neoplasia, tumor, cancer or metastatic cell establishment, formation, proliferation, growth or survival (apoptosis) has occurred. For a solid neoplasia, tumor or cancer, invasive and non-invasive imaging methods can ascertain neoplasia, tumor or cancer size or volume. Examination of blood or serum, or bone marrow, for example, for populations, numbers and types of cells (e.g., hematopoetic cellular hyperproliferative disorders, disseminated tumor cells) can establish whether a reduction or stabilization in mass or numbers of neoplastic, tumor, cancer or metastasis cells or inhibition of neoplastic, tumor, cancer or metastasis establishment, formation, proliferation, growth or survival (apoptosis) has occurred.

Invention compositions and methods can be combined with any other treatment or therapy that provides a desired effect. In particular, treatments and therapies that have been characterized as having an anti-cell proliferative activity or function are applicable. Exemplary treatments and therapies include anti-cell proliferative or immune enhancing agents or drugs.

The treatments and therapies can be performed prior to, substantially contemporaneously with any other methods of the invention, for example, an anti-cell proliferative or anti-cellular hyperproliferative disorder (e.g., a neoplasia, tumor or cancer, or metastasis).

The invention therefore provides combination methods in which the methods of the invention, in which any of the antibodies, functional fragments, and modified and variant forms, are used in a combination with any therapeutic regimen, treatment protocol or composition, such as an anti-cell proliferative rotocol, agent or drug set forth herein or known in the art. In one embodiment, a method includes administering LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 and an anti-cell proliferative or immune enhancing treatment, agent or drug. In another embodiment, a method includes administering an antibody that binds to an LM-1 antigen (e.g., NONO/nmt55), and an anti-cell proliferative or immune enhancing treatment, agent or drug. The anti-cell proliferative or immune enhancing treatment, agent or drug can be administered prior to, substantially contemporaneously with or following administration of LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or antibody that binds to an LM-1 antigen (e.g., NONO/nmt55).

As used herein, an "anti-cell proliferative," "anti-neoplastic," "anti-tumor," or "anti-cancer" treatment, therapy, activity or effect means any therapy, treatment regimen, agent, drug, protocol or process that is useful in treating pathologies, adverse symptoms or complications associated with or caused by abnormal or undesirable cell proliferation (cell hyperproliferation), a cellular hyperproliferative disorder, neoplasia, tumor or cancer, or metastasis. Particular therapies, treatment regimens, agents, drugs, protocol or processes can inhibit, decrease, slow, reduce, delay, or prevent cell proliferation, cell growth, cellular hyperproliferation, neoplastic, tumor, or cancer (malignant) growth, proliferation, survival or metastasis. Such treatments, therapies, regimens, protocols, agents and drugs, can operate by disrupting, reducing, inhibiting or delaying cell cycle progression or cell proliferation or growth; increasing, stimulating or enhancing cell apoptosis, lysis or death; inhibiting nucleic acid or protein synthesis or metabolism; reducing, decreasing, inhibiting or delaying cell division; or decreasing, reducing or inhibiting cell survival, or production or utilization of a cell survival factor, growth factor or signaling pathway (extracellular or intracellular).

Examples of anti-cell proliferative treatments and therapies include chemotherapy, immunotherapy, radiotherapy (ionizing or chemical), local or regional thermal (hyperthermia) therapy and surgical resection.

Specific non-limiting classes of anti-cell proliferative agents and drugs include alkylating agents, anti-metabolites, plant extracts, plant alkaloids, nitrosoureas, hormones (steroids), nucleoside and nucleotide analogues. Specific non-limiting examples of microbial toxins include bacterial cholera toxin, pertussis toxin, anthrax toxin, diphtheria toxin, and plant toxin ricin. Specific examples of drugs include cyclophosphamide, azathioprine, cyclosporin A, melphalan, chlorambucil, mechlorethamine, busulphan, methotrexate, 6-mercaptopurine, thioguanine, 5-fluorouracil, 5-fluorouridine, cytosine arabinoside, 6-thioguanine, 6-mercatopurine, AZT, 5-azacytidine (5-AZC) and 5-azacytidine related compounds, pentostatine, gemcitabine, cytarabine, bleomycin, actinomycin D, dactinomycin, mithramycin, mitomycin C, carmustine, calicheamicin, lomustine, semustine, streptozotocin, teniposide, etoposide, hydroxyurea, nitrosourea, cisplatin, carboplatin, levamisole, ifosfamide, mitotane, mitoxantrone, procarbazine, dacarbazine, taxol, vinblastine, vincristine, vindesine, doxorubicin, daunorubicin, epirubicin, idarubicin, daunomycin and dibromomannitol. Specific non-limiting examples of hormones include prednisone, prednisolone, diethylstilbesterol, fluoxymesterone, flutamide, leuprolide, toremifene, triamcinolone, zoladex, and gonatrophin releasing hormone antagonists.

Radiotherapy includes internal or external delivery to a subject. For example, alpha, beta, gamma and X-rays can administered to the subject externally without the subject internalizing or otherwise physically contacting the radioisotope. Specific examples of X-ray dosages range from daily doses of 50 to 200 roentgens for prolonged periods of time (3 to 5/week), to single doses of 2000 to 6000 roentgens. Dosages vary widely, and depend on duration of exposure, the half-life of the isotope, the type of radiation emitted, the cell type and location treated and the progressive stage of the disease. Specific non-limiting examples of radionuclides include, for example, $^{47}$Sc $^{67}$Cu, $^{72}$Se, $^{88}$Y, $^{90}$Sr, $^{90}$Y, $^{97}$Ru, $^{99}$Tc, $^{105}$Rh, $^{111}$In, $^{125}$I, $^{131}$I, $^{149}$Tb, $^{153}$Sm, $^{186}$Re, $^{188}$Re, $^{194}$Os, $^{203}$Pb, $^{211}$At, $^{212}$Bi, $^{213}$Bi, $^{212}$Pb, $^{223}$Ra, $^{225}$Ac, $^{227}$Ac, and $^{228}$Th.

Antibodies that bind to tumor cells are a particular example of an anti-cell proliferative treatment or therapy. Anti-tumor antibodies include, for example, M195 antibody which binds to leukemia cell CD33 antigen (U.S. Pat. No. 6,599,505); monoclonal antibody DS6 which binds to ovarian carcinoma CA6 tumor-associated antigen (U.S. Pat. No. 6,596,503); human IBD12 monoclonal antibody which binds to epithelial cell surface H antigen (U.S. Pat. No. 4,814,275); and BR96 antibody which binds to Le$^x$ carbohydrate epitope expressed by colon, breast, ovary, and lung carcinomas. Additional anti-tumor antibodies that can be employed include, for example, Herceptin (anti-Her-2 neu antibody), Rituxan®, Zevalin, Bevacizumab (Avastin), Bexxar, Campath®, Oncolym, 17-1A (Edrecolomab), 3F8 (anti-neuroblastoma antibody), MDX-CTLA4, IMC-C225 (Cetuximab) and Mylotarg.

As used here, the term "immune enhancing," when used in reference to a treatment, therapy, agent or drug means that the treatment, therapy, agent or drug provides an increase, stimulation, induction or promotion of an immune response, humoral or cell-mediated. Such therapies can enhance immune response generally, or enhance immune response to a specific target, e.g., a cell proliferative or cellular hyperproliferative disorder such as a neoplasia, tumor or cancer, or metastasis.

Specific non-limiting examples of immune enhancing agents include antibody, cell growth factors, cell survival factors, cell differentiative factors, cytokines, interferons and chemokines. Additional examples of immune enhancing agents and treatments include immune cells such as lymphocytes, plasma cells, macrophages, dendritic cells, NK cells and B-cells that either express antibody against the cell proliferative disorder or otherwise are likely to mount an immune response against the cell proliferative disorder. Cytokines that enhance or stimulate immunogenicity include IL-2, IL-1α, IL-1β, IL-3, IL-6, IL-7, granulocyte-macrophage-colony stimulating factor (GMCSF), IFN-γ, IL-12, TNF-α, and TNFβ, which are also non-limiting examples of immune enhancing agents. Chemokines including MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, PARC, TARC, LARC/MIP-3α, CKβ, CKβ6, CKβ7, CKβ8, CKβ9, CKβ11, CKβ12, C10, IL-8, ENA-78, GROα, GROβ, GCP-2, PBP/CTAPIIIβ-TG/NAP-2, Mig, PBSF/SDF-1, and lymphotactin are further non-limiting examples of immune enhancing agents.

Methods of the invention also include, among other things, methods that result in a reduced need or use of another treatment protocol or therapeutic regimen, process or remedy. For example, for a neoplasia, tumor or cancer, or metastasis, a method of the invention has a therapeutic benefit if in a given subject it results in a less frequent or reduced dose or elimination of an anti-cell proliferative (e.g., anti-neoplastic, anti-tumor, anti-cancer or anti-metastatic) or immune enhancing treatment or therapy, such as a chemotherapeutic drug, radiotherapy, immunotherapy, or surgery for neoplasia, tumor or cancer, or metastasis treatment or therapy.

In accordance with the invention, methods of reducing need or use of an anti-cell proliferative (e.g., anti-neoplastic, anti-tumor, anti-cancer or anti-metastasis) treatment or therapy are provided. In one embodiment, a method includes administering to a subject LM-1 antibody, as represented by antibody produced by a cell line DSMZ Deposit No. DSM ACC 2623, or represented by heavy and light chain sequences set forth as SEQ ID NOs:1, 3, 5 or 7, and 9 in an amount effective to treat a cellular hyperproliferative disorder (e.g., a neoplasia, tumor or cancer, or metastasis), and to reduce or eliminate need for an anti-cell proliferative (anti-neoplasia, anti-tumor or anti-cancer, or anti-metastasis) or immune-enhancing therapy. In another embodiment, a method includes administering to a subject an antibody that binds to an LM-1 antigen (e.g., NONO/nmt55) in an amount effective to treat a cellular hyperproliferative disorder (e.g., a neoplasia, tumor or cancer, or metastasis), and to reduce or eliminate need for an anti-cell proliferative (anti-neoplasia, anti-tumor or anti-cancer, or anti-metastasis) or immune-enhancing therapy. The methods can be performed prior to, substantially contemporaneously with or following administration of an anti-neoplastic, -tumor, -cancer or -metastasis, or immune-enhancing therapy.

The doses or "amount effective" or "amount sufficient" in a method of treatment or therapy in which it is desired to achieve a therapeutic benefit or improvement includes, for example, any objective or subjective alleviation or amelioration of one, several or all pathologies, adverse symptoms or complications associated with or caused by the target (e.g., cellular hyperproliferative disorder), to a measurable or detectable extent, although preventing, inhibiting or delaying a progression or worsening of the target (e.g., cellular hyperproliferative disorder) pathology, adverse symptom or complication, is a satisfactory outcome. Thus, in the case of a cellular hyperproliferative disorder, the amount will be sufficient to provide a therapeutic benefit to a given subject or to alleviate or ameliorate a pathology, adverse symptom or complication of the disorder in a given subject. Single or multiple doses may be administered or the dose may be proportionally increased or reduced as indicated by the status of treatment or therapeutic target (e.g., cellular hyperproliferative disorder) or any side effect(s) of the treatment or therapy.

Exemplary non-limiting amounts (doses) are in a range of about 0.1 mg/kg to about 100 mg/kg, and any numerical value or range or value within such ranges. Greater or lesser amounts (or doses) can be administered, for example, 0.01-500 mg/kg, and any numerical value or range or value within such ranges. Additional exemplary non-limiting amounts (or doses) range from about 0.1-50 mg/kg, 0.5-50 mg/kg, 1.0-25 mg/kg, 1.0-10 mg/kg, and any numerical value or range or value within such ranges.

Methods of the invention may be practiced one or more times (e.g., 1-10, 1-5 or 1-3 times) per day, week, month, or year. The skilled artisan will know when it is appropriate to delay or discontinue administration. An exemplary non-limiting dosage schedule is 1-7 times per week, for 1, 2, 3, 4, 5, 6, 7, 8, 9, 10, 15, 20 or more weeks, and any numerical value or range or value within such ranges.

Of course, as is typical for any treatment or therapy, different subjects will exhibit different responses to treatment and some may not respond or respond inadequately to a particular treatment protocol, regimen or process. Amounts effective or sufficient will therefore depend at least in part upon the disorder treated (e.g., cell proliferation, benign hyperplasia or a neoplasia, tumor or cancer and the type or stage, e.g., the tumor or cancer grade and if it is advanced, late or early stage), the therapeutic effect desired, as well as the individual subject (e.g., the bioavailability within the subject, gender, age, etc.) and the subject's response to the treatment based upon genetic and epigenetic variability (e.g., pharmacogenomics).

Cell toxicity and viability (cell apoptosis, lysis, growth proliferation, etc.) can be measured in a variety of ways on the basis of colorimetric, luminescent, radiometric, or fluorometric assays known in the art. Colorimetric techniques for determining cell viability include, for example, Trypan Blue exclusion. In brief, cells are stained with Trypan Blue and counted using a hemocytometer. Viable cells exclude the dye whereas dead and dying cells take up the blue dye and are easily distinguished under a light microscope. Neutral Red is adsorbed by viable cells and concentrates in cell lysosomes; viable cells can be determined with a light microscope by quantitating numbers of Neutral Red stained cells.

Fluorometric techniques for determining cell viability include, for example, propidium iodide, a fluorescent DNA intercalating agent. Propidium iodide is excluded from viable cells but stains the nucleus of dead cells. Flow cytometry of propidium iodide labeled cells can then be used to quantitate viable and dead cells. Release of lactate dehydrogenase (LDH) indicates structural damage and death of cells, and can be measured by a spectrophotometric enzyme assay. Bromodeoxyuridine (BrdU) is incorporated into newly synthesized DNA and can be detected with a fluorochrome-labeled antibody. The fluorescent dye Hoechst 33258 labels DNA and can be used to quantitate proliferation of cells (e.g., flow cytometry). Quantitative incorporation of the fluorescent dye carboxyfluorescein diacetate succinimidyl ester (CFSE or CFDA-SE) can provide cell division analysis (e.g., flow cytometry). This technique can be used either in vitro or in vivo. 7-aminoactinomycin D (7-AAD) is a fluorescent intercalator that undergoes a spectral shift upon association with DNA, and can provide cell division analysis (e.g., flow cytometry).

Radiometric techniques for determining cell proliferation include, for example, [$^3$H]-Thymidine, which is incorporated into newly synthesized DNA of living cells and frequently used to determine proliferation of cells. Chromium ($^{51}$Cr)-release from dead cells can be quantitated by scintillation counting in order to quantitate cell viability.

Luminescent techniques for determining cell viability include, for example, the CellTiter-Glo luminescent cell viability assay (Promega Madison Wis.). This technique quantifies the amount of ATP present to determine the number of viable cells.

Commercially available kits for determining cell viability and cell proliferation include, for example, Cell Proliferation Biotrak ELISA (Amersham Biosciences Piscataway, N.J.); the Guava ViaCount™ Assay, which provides rapid cell counts and viability determination based on differential uptake of fluorescent reagents (Guava Technologies, Hayward, Calif.); the CyQUANT® Cell Proliferation Assay Kit (Molecular Probes, Inc., Eugene, Oreg.); and the CytoLux Assay Kit (PerkinElmer Life Sciences Inc., Boston, Mass.). The DELFIA® Assay Kits (PerkinElmer Life Sciences Inc., Boston, Mass.) can determine cell proliferation and viability using a time-resolved fluorometric method. The Quantos™ Cell Proliferation Assay is a fluorescence-based assay that measures the fluorescence of a DNA-dye complex from lysed cells (Stratagene, La Jolla, Calif.). The CellTiter-Glo cell viability assay is a luminescent assay for measuring cell viability (Promega, Madison Wis.).

The terms "subject" and "patient" are used interchangeably herein and refer to animals, typically mammals, such as humans, non-human primates (gorilla, chimpanzee, orangutan, macaque, gibbon), domestic animals (dog and cat), farm and ranch animals (horse, cow, goat, sheep, pig), laboratory and experimental animals (mouse, rat, rabbit, guinea pig). Subjects include disease model animals (e.g., such as mice, rats and non-human primates) for studying in vivo efficacy (e.g., a neoplasia, tumor or cancer, or metastasis animal model). Human subjects include children, for example, newborns, infants, toddlers and teens, between the ages of 1 and 5, 5 and 10 and 10 and 18 years, adults between the ages of 18 and 60 years, and the elderly, for example, between the ages of 60 and 65, 65 and 70 and 70 and 100 years.

Subjects include mammals (e.g., humans) in need of treatment, that is, they have undesirable or aberrant cell proliferation (cell hyperproliferation) or a cellular hyperproliferative disorder. Subjects also include those at risk of having a undesirable cell proliferation or a cellular hyperproliferative disorder. Subjects further include a subject in need of an anti-cell proliferative or immune enhancing treatment or therapy due to a lab or clinical diagnosis warranting such treatment, subjects undergoing an anti-cell proliferative or immune enhancing therapy, and subjects having undergone an anti-cell proliferative or immune enhancing therapy and are at risk of relapse or recurrence.

At risk subjects include those with a family history, genetic predisposition, or who have suffered a previous affliction with a cell proliferative or cellular hyperproliferative disorder (e.g., a benign hyperplasia, neoplasia, tumor or cancer, or metastasis), and are at risk of relapse or recurrence. At risk subjects further include environmental exposure to carcinogens or mutagens, such as smokers, or those in an occupational (industrial, chemical, agricultural) setting. Such subjects at risk for developing a cell proliferative or cellular hyperproliferative disorder such as neoplasia, tumor or cancer can be identified with genetic screens for tumor associated genes, gene deletions or gene mutations. Subjects that lack Brca1 are at risk for developing breast cancer, for example. Subjects at risk for developing colon cancer have deleted or mutated tumor suppressor genes, such as adenomatous polyposis coli (APC), for example. At risk subjects having particular genetic predisposition towards cell proliferative disorders are known (see, e.g., *The Genetic Basis of Human Cancer* $2^{nd}$ ed. by Bert Vogelstein (Editor), Kenneth W. Kinzler (Editor) (2002) McGraw-Hill Professional; *The Molecular Basis of Human Cancer*. Edited by W B Coleman and G J Tsongalis (2001) Humana Press; and *The Molecular Basis of Cancer*. Mendelsohn et al., WB Saunders (1995)).

At risk subjects can therefore be treated in order to inhibit or reduce the likelihood of developing a cell proliferative or cellular hyperproliferative disorder, or after having been cured of a cell proliferative disorder, suffering a relapse or recurrence of the same or a different cell proliferative or cellular hyperproliferative disorder. The result of such treatment can be to reduce the risk of developing a cell proliferative or cellular hyperproliferative disorder, or to prevent a cell proliferative or cellular hyperproliferative disorder, or a pathology, adverse symptom or complication thereof in the treated at risk subject.

The invention further provides kits, including antibodies, functional fragments, modified and variants forms, nucleic acids, agents, drugs and pharmaceutical formulations, packaged into suitable packaging material, optionally in combination with instructions for using the kit components, e.g., instructions for performing a method of the invention. In one embodiment, a kit includes an LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55). In one aspect, the instructions are for treating undesirable cell proliferation or hyperproliferation, or a cellular hyperproliferative disorder. In another aspect, the instructions are for treating a neoplasia, tumor or cancer, or metastasis. In a further embodiment, a kit includes an LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55), and instructions for treating undesirable cell proliferation or hyperproliferation, or a cellular hyperproliferative disorder, and an anti-cell proliferative or immune enhancing treatment, agent or drug. In various aspects, a kit includes an anti-neoplastic, anti-cancer or anti-tumor agent. In still a further aspects, a kit includes an article of manufacture, for example, an article of manufacture for delivering the antibody or nucleic acid, anti-cell proliferative or immune enhancing treatment, agent or drug into a subject locally, regionally or systemically.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., treating a cell proliferative or cellular hyperproliferative disorder, an assay for screening for, detecting or identifying a LM-1 antigen (e.g., NONO/nmt55), or a cell to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds, etc. Thus, in additional embodiments, a kit includes a label or packaging insert including instructions for practicing a method of the invention in solution, in vitro, in vivo, or ex vivo.

Instructions can therefore include instructions for practicing any of the methods of the invention described herein. For example, invention pharmaceutical compositions can be included in a container, pack, or dispenser together with instructions for administration to a subject to treat a cell proliferative or cellular hyperproliferative disorder, such as a neoplasia, tumor or cancer, or metastasis. Instructions may additionally include indications of a satisfactory clinical endpoint or any adverse symptoms or complications that may occur, storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages.

Antibodies (e.g., LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or antibody that binds to an LM-1 antigen (e.g., NONO/nmt55)), nucleic acids, and other compositions (e.g., LM-1 antigen (e.g., NONO/nmt55)) and methods of the invention can be included in or employ pharmaceutical formulations. Such pharmaceutical formulations are useful for treatment of, or administration or delivery to, a subject in vivo or ex vivo.

Pharmaceutical formulations include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the formulations.

Pharmaceutical formulations can be made to be compatible with a particular local, regional or systemic administration or delivery route. Thus, pharmaceutical formulations include carriers, diluents, or excipients suitable for administration by particular routes. Specific non-limiting examples of routes of administration for compositions of the invention are parenteral, e.g., intravenous, intrarterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

Solutions or suspensions used for parenteral application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, sodium chloride can be included in the composition. Including an agent which delays absorption, for example, aluminum monostearate or gelatin can prolong absorption of injectable compositions.

Sterile injectable formulations can be prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

The pharmaceutical formulations can be prepared with carriers that protect against rapid elimination from the body, such as a controlled release formulation or a time delay material such as glyceryl monostearate or glyceryl stearate. The formulations can also be delivered using articles of manufacture such as implants and microencapsulated delivery systems to achieve local, regional or systemic delivery or controlled or sustained release.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation (Palo Alto, Calif.). Liposomal suspensions (including liposomes targeted to cells or tissues using antibodies or viral coat proteins) can also be used as pharmaceutically acceptable carriers. These can be prepared according to known methods, for example, as described in U.S. Pat. No. 4,522,811.

Additional pharmaceutical formulations appropriate for administration are known in the art (see, e.g., Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins Publishers (1999); Kibbe (ed.), *Handbook of Pharmaceutical Excipients American Pharmaceutical Association*, 3$^{rd}$ ed. (2000); and *Remington's Pharmaceutical Principles of Solid Dosage Forms*, Technonic Publishing Co., Inc., Lancaster, Pa., (1993)).

The compositions used in accordance with the invention, including proteins (antibodies), nucleic acid (inhibitory), treatments, therapies, agents, drugs and pharmaceutical formulations can be packaged in dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms will depend on a variety of factors including, but not necessarily limited to, the particular composition employed, the effect to be achieved, and the pharmacodynamics and pharmacogenomics of the subject to be treated.

The invention provides cell-free (e.g., in solution, in solid phase) and cell-based (e.g., in vitro or in vivo) methods of screening, detecting and identifying a cell or antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. The methods can be performed in solution, in vitro using a biological material or sample, and in vivo, for example, using neoplastic, tumor or cancer, or metastasis cells, tissue or organ (e.g., a biopsy) from an animal.

In accordance with the invention, there are provided methods of identifying, detecting or screening for a cell or an antigen (e.g., NONO/nmt55) to which LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13 binds. In one embodiment, a method includes contacting a biological material or sample with a LM-1 antibody, as represented by antibody produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55) under conditions allowing binding of the antibody to a cell or antigen; and assaying for binding of the antibody to the cell or antigen. The binding of the antibody to a cell or antigen detects their presence. In one aspect, the biological material or sample is obtained from a mammalian subject. In a further aspect, the antibody that binds to the cell or antigen (e.g., NONO/nmt55) is distinct from LM-1 antibody, produced by a cell line DSMZ Deposit No. DSM ACC 2623, or represented by heavy and light chain sequences set forth as SEQ ID NOs:1, 3, 5, 7 or 9, and 11 or 13 binds.

The invention also provides cell-free (e.g., in solution, in solid phase) and cell-based (e.g., in vitro or in vivo) methods of diagnosing and monitoring progression of a subject having or at increased risk of having undesirable or aberrant cell proliferation or a cellular hyperproliferative disorder (e.g., neoplasia, tumor or cancer, or metastasis), the presence or extent of undesirable or aberrant cell proliferation or a cellular hyperproliferative disorder (e.g., neoplasia, tumor or cancer, or metastasis), as well as identifying a subject appropriated for treatment with an LM-1 antibody, or an antibody that binds to an LM-1 antigen (e.g., NONO/nmt55), due to increased probability of responding to treatment. The methods can be performed in solution, in vitro using a biological material or sample, for example, a biopsy of suspicious cells that may comprise or be indicative of neoplastic, tumor or cancer, or metastasis cells, tissue or organ. The methods can also be performed in vivo, for example, in an animal.

In accordance with the invention, there are provided methods of diagnosing and monitoring progression of a subject having or at increased risk of having undesirable or aberrant cell proliferation or a cellular hyperproliferative disorder (e.g., neoplasia, tumor or cancer, or metastasis), methods of determining the presence or extent of undesirable or aberrant cell proliferation or a cellular hyperproliferative disorder (e.g., neoplasia, tumor or cancer, or metastasis), and methods of identifying a subject appropriate for treatment with an LM-1 antibody, or an antibody that binds to an LM-1 antigen (e.g., NONO/nmt55). In one embodiment, a method includes contacting a biological material or sample (e.g., from a subject) with an LM-1 antibody, produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55), under conditions allowing binding of the antibody to a cell or antigen; and assaying for binding of the antibody to the cell or antigen. The binding of the antibody to the cell or antigen can be used to ascertain the presence or amount of cell or antigen, which can be correlated with increased risk of having undesirable or aberrant cell proliferation or a cellular hyperproliferative disorder (e.g., neoplasia, tumor or cancer, or metastasis), or the presence or extent of undesirable or aberrant cell proliferation or a cellular hyperproliferative disorder (e.g., neoplasia, tumor or cancer, or metastasis), thereby diagnosing the subject. The presence or amount of cell or antigen (e.g., NONO/nmt55) can also identify a subject appropriate for treatment, as such subjects will have a greater probability of favorably responding to treatment of a hyperproliferative disorder (e.g., neoplasia, tumor or cancer, or metastasis), for example, treatment with an with an LM-1 antibody, produced by a cell line DSMZ Deposit No. DSM ACC 2623, or represented by heavy and light chain sequences set forth as SEQ ID NOs:1, 3, 5, 7 or 9, and 11 or 13, or an antibody that binds to an LM-1 antigen (e.g., NONO/nmt55). In one aspect, a biological material or sample is obtained from a human. In another aspect, a biological material or sample comprises a biopsy (e.g., a biopsy of lung, pancreas, stomach, breast, esophagus, ovary or uterus). Methods of monitoring progression of undesirable or aberrant cell proliferation or a cellular hyperproliferative disorder (e.g., neoplasia, tumor or cancer, or metastasis) can be performed at a regular or irregular intervals, for example, daily, bi-weekly, weekly, bi-monthly, monthly, quaterly, semi- or bi-annually, annually, etc., as appropriate.

Identifying, detecting, screening and diagnostic assays of the invention can be practiced by analysis of potential or suspect hyperproliferating cells, for example, a cell of a cellular hyperproliferative disorder or an appropriate sample. Cells include hyperproliferating, immortalized, neoplastic, tumor and cancer cell lines and primary isolates derived from breast, lung, thyroid, head and neck, nasopharynx, nose or sinuses, brain, spine, adrenal gland, thyroid, lymph, gastrointestinal (mouth, esophagus, stomach, duodenum, ileum, jejunum (small intestine), colon, rectum), genito-urinary tract (uterus, ovary, endometrium, cervix, bladder, testicle, penis, prostate), kidney, pancreas, adrenal gland, liver, bone, bone marrow, lymph, blood, muscle, skin, and the hematopoetic system, and metastasis or secondary sites.

The term "contacting," when used in reference to a composition such as a protein (e.g., antibody), material, sample, or treatment, means a direct or indirect interaction between the composition (e.g., protein such as an antibody) and the other referenced entity. A particular example of direct interaction is binding. A particular example of an indirect interaction is where the composition acts upon an intermediary molecule, which in turn acts upon the referenced entity. Thus, for example, contacting a cell (e.g., that comprises a cellular hyperproliferative disorder) with an antibody includes allowing the antibody to bind to the cell, or allowing the antibody to act upon an intermediary (e.g., antigen) that in turn acts upon the cell.

The terms "assaying" and "measuring" and grammatical variations thereof are used interchangeably herein and refer to either qualitative or quantitative determinations, or both qualitative and quantitative determinations. When the terms are used in reference to binding, any means of assessing the relative amount, affinity or specificity of binding is contemplated, including the various methods set forth herein and known in the art. For example, antibody binding can be assayed or measured by an ELISA assay, Western blot or immunoprecipitation assay.

The term "correlating" and grammatical variations thereof refers to a relationship or link between two or more entities. For example, LM-1 antigen (e.g., NONO/nmt55), or cells that express LM-1 antigen (e.g., on the cell surface) are associated with various tumors, neoplasias, cancers and metastasis. Thus, because of this relationship between cell surface expressed LM-1 antigen (e.g., NONO/nmt55) and cancer, they correlate with each other. Thus, correlating the quantity of LM-1 antigen (e.g., NONO/nmt55) or cells expressing LM-1 antigen (e.g., on the cell surface) can indicate the presence and/or extent of a tumor, neoplasia, cancer or metastasis in a subject.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, Genbank accession numbers and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to an "antibody" includes a plurality of antibodies and reference to "a treatment or therapy" can include multiple simultaneous, consecutive or sequential doses, treatments or therapies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes any numerical value or range within or encompassing such values, such as 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and any numerical range within such a range, such as 90-92%, 90-95%, 95-98%, 96-98%, 99-100%, etc. In an additional example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a range, such as 1-2, 5-10, 10-50, 50-100, 100-500, 100-1000, 500-1000, 1000-2000, 1000-5000, etc. In a further example, reference to a range of KD $10^{-5}$ M to about KD $10^{-13}$ M includes any numerical value or range within or encompassing such values.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described.

Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of materials and methods.

Cell Culture: Human lung squamous cell carcinoma cell line LOU-NH91 was cultured in RPMI-1640 media (PAA, Vienna, Austria) supplemented with 20% fetal calf serum (FCS), 2 mM glutamine and penicillin/streptomycin (both 1%) and incubated in a humidified, 5% $CO_2$ atmosphere at 37° C. For the assays described, cells were grown to sub-confluency, detached with trypsin/EDTA and washed twice with phosphate buffered saline (PBS) before use.

Producing Hybridomas: We immortalized lymphocytes by fusing them to the HAB-1 heteromyeloma. In brief, the HAB-1 heteromyeloma cells were washed twice with RPMI 1640 (PAA, Vienna, Austria) without additives and centrifuged the cells for 5 minutes at 1500 rpm. We then thawed frozen lymphocytes obtained from either the spleen or the lymph nodes and we washed these cells twice with RPMI 1640 without additives and centrifuged these cells at 1500 rpm for 5 minutes. Both the HAB-1 and the lymphocyte cell pellets were resuspended in 10 ml RPMI 1640 without additives and were counted in a Neubauer cell counting chamber. We washed the cells again, added the HAB-1 cells and the lymphocytes together in a ratio of 1:2 to 1:3, mixed them, and centrifuged the mixture for 8 minutes at 1500 rpm. We pre-warmed Polyethylene Glycol 1500 (PEG) to 37° C. and carefully let the PEG run drop-wise onto the pellet while slightly rotating the 50 ml tube. Next, we gently resuspended the pellet and rotated the tube for exactly 90 seconds in a 37° C. water bath. We washed the cells twice with a full 10 ml pipette of RPMI without additives and centrifuged the cells for 5 minutes at 1500 rpm. We added 1 ml of RPMI 1640 with HAT supplement (PAA, Vienna, Austria) and 10% FCS, 1% glutamine, and 1% penicillin/streptomycin ("RPMI 1640 HAT") into each well of a 24-well plate. The cell pellet was dissolved in RPMI 1640 HAT and 0.5 ml of the cells was added to each well of the 24-well plate. We then placed the 24-well plates into a 37° C. incubator and changed the RPMI 1640 HAT medium weekly. After four to six weeks, the cell culture supernatants were screened for antibody production in an enzyme-linked immunosorbent assay (ELISA).

Using this protocol, approximately 80% to 90% of the triomas generated are viable and approximately 50% secrete immunoglobulins. Positive clones were tested immunohistochemically on autologous tumor tissue sections and clones that showed a positive reaction were subsequently re-cloned.

cDNA Synthesis and RT-PCR: To obtain the sequence of the antibody, we isolated whole RNA from the trioma using the RNASE Kit from Qiagen. Total RNA may also be prepared using methods standard in the art, e.g., those described in Krenn et al. (Clip. Exp. Immunol. 115:168-175, 1999). cDNA synthesis from total RNA obtained from hybridoma cell line LM-1 (DSMZ Accession No. DSM ACC2623) was performed with 5 µg total RNA using Gibco BRL (Eggenstein, Germany) M-MLV Reverse Transcriptase according to the manufacturer's instructions. The amplification of $V_H$ and $V_L$ genes was carried out in a 25 µl volume with 1.75 mM $MgCl_2$, 0.4 pM primer, 200 µM of each dNTP, and IU Taq polymerase (MBI Fermentas, St. Leon-Rot, Germany). The PCR-products were amplified using the following cycle profiles: 95° C. for 2 min, followed by 35 cycles of 94° C. for 30 sec; 65° C. for 30 sec (for VH3 and VH4 primers), 60° C. for VH1, VH2, VH5, VH6 and 52° C. for VL primers respectively; a final extension at 72° C. for 4 min.

Sequencing the Antibody: The PCR products were purified using gel electrophoresis through 2% agarose (Roth, Karlsruhe, Germany) followed by gel extraction of the PCR product using a Jetsorb gel extraction kit (Genomed, Bad Oeynhausen, Germany). The PCR products were then cloned using the pCR-Script Amp SK$^+$ cloning kit (Stratagene, Heidelberg, Germany). Ten positive clones were sequenced using the DyeDeoxy termination cycle sequencing kit (Applied Bio-Systems Inc., Weiterstadt, Germany) and analysed with an ABIPrism373 automated DNA sequencer (both strands were sequenced using T3 and T7 primers). The sequences were analysed using the DNASIS for Windows sequence comparison software and the GenBank and IMGT/V-QUEST databases. The International Immunogenetics ("IMGT") database is coordinated by Marie-Paule Lefranc at the Université Montpellier, Montpellier, France.

Immunohistochemical Staining of Paraffin Sections: Paraffin-embedded human tissues were sectioned (2 µm). Paraffin was removed by two xylene washes for 5 minutes each, two 100% ethanol washes for 5 minutes each, one methanol (70 ml) and $H_2O_2$ (500 µl) wash for 5 minutes, two 90% ethanol washes for 3 minutes each, two 80% ethanol washes for 3 minutes each, two 70% ethanol washes for 3 minutes each, and washing in Tris/NaCl (3 grams Tris, 40.5 grams NaCl in 5 litres of distilled $H_2O$ and pH adjusted to 7.4 with HCl).

Slides containing the tissue sections were incubated in 300 ml distilled $H_2O$ and citric acid (pH 5.5) in a pressure cooker at 100° C. for 5 minutes. The slides were blocked for 15 minutes with 150 µl of 0.5% Bovine Serum Albumin Fraction V ("BSA;" Roth, Karlsruhe, Germany) in phosphate buffered saline ("PBS") per slide, and washed once with Tris/NaCl.

The sections were incubated with the primary antibody (e.g., LM-1, unrelated, human monoclonal IgM antibodies (ChromPure IgM, Dianova, Hamburg, Germany, 10 µg/ml), CK8 antibody, or mouse CAM 5.2 antibody) diluted 1:50

(CAM 5.2 diluted 1:10) with BSA/PBS (Dako, Hamburg, Germany) for 2.5 hours in a humidified incubator at 37° C. The sections were then washed three times with Tris/NaCl (3 grams Tris, 40.5 grams NaCl in 5 litres of distilled $H_2O$ and pH adjusted to 7.4 with HCl), followed by incubation with the secondary antibody (e.g., peroxidase-labeled rabbit anti-human or rabbit anti-mouse conjugate (Dako)) diluted 1:50 in PBS containing 30% rabbit serum at room temperature ("RT") for 1 hour. After washing three times with Tris/NaCl the tissue sections were incubated in PBS for 10 minutes before staining with 150 µl diaminobenzidine (0.05%)-hydrogen peroxide (0.02%) for 10 minutes at RT. The reaction was stopped using running tap water (10-15 minutes) and the sections counterstained with hematoxylin. After mounting with glycerol-gelatin, the sections were analyzed using light microscopy.

Immunohistochemical Staining of Cryo-Sections from Autologous Tumors: Frozen human tissues were sectioned (4 µm) air-dried for two hours, fixed in acetone, air-dried for 30 minutes, and washed with Tris/NaCl (3 grams Tris, 40.5 grams NaCl in 5 litres of distilled $H_2O$ and pH adjusted to 7.4 with HCl). The cryosections were then blocked with PBS containing 3% milk powder for 15-30 minutes at RT. After washing three times with Tris/NaCl the sections were incubated with LM-1 human IgM antibodies, unrelated human monoclonal IgM (Chrompure IgM, Dianova, 10 µg/ml), CK8 (diluted 1:50 with BSA/PBS; Dako) or mouse CAM 5.2 antibody (diluted 1:10 with BSA/PBS) for 30 minutes at RT. The sections were washed three times with Tris/NaCl, followed by incubation with secondary antibodies (peroxidase-labeled rabbit anti-human or rabbit anti-mouse conjugate 1:50 in 70% PBS and 30% human serum) for 30 minutes at RT. After washing three times with Tris/NaCl and incubation in PBS for 10 minutes, the sections were stained with diaminobenzidine (0.05%)-hydrogen peroxide (0.02%) for 10 minutes at RT. The reaction was stopped under running tap water and the sections counterstained with hematoxylin. After mounting with glycerol-gelatin, the sections were analyzed using light microscopy.

Preparation of Tumor Cell Membrane Extracts: Isolation of membrane proteins from tumor cells was performed as described using standard methods in the art, as described, for example, in Hensel et al. (Int. 7. Cancer 81:229-235, 1999). In particular, confluent tumor cells (e.g., LOU-NH91 cells) were washed twice with PBS, harvested with a cell scraper, centrifuged, and resuspended in hypotonic buffer (20 mM HEPES, 3 mM KCl, 3 mM $MgCl_2$) and incubated for 15 minutes on ice. The cells were then sonicated for 5 minutes and the nuclei were pelleted by centrifugation at 10,000×g for 10 min. The supernatant was centrifuged for 40 minutes at 100,000×g in a swing-out rotor to pellet the membranes. After washing the pellet with hypotonic buffer, the pellet was resuspended in membrane lysis buffer (50 mM HEPES pH 7.4, 0.1 mM EDTA, 10% glycerol, and 1% Triton X-100). Complete protease inhibitor (Boehringer, Mannheim, Germany) also was added to all solutions.

Western Blotting: Western blots were performed using standard techniques as described, for example, in Hensel et al. (Int. 7. Cancer 81:229-235, 1999). In short, blotted nitrocellulose membranes were blocked with PBS containing 3% low fat milk powder, followed by incubation for 1 hour with 20-40 µg of LM-1 human IgM antibodies or unrelated human control IgM (ChromPure IgM, Dianova). The secondary antibody (peroxidase-coupled rabbit anti-human IgM antibody 1:1,000, Dianova) was detected with the SUPERSIGNAL chemiluminescence kit from Pierce (KMF, St. Augustin, Germany).

Cytospin Preparation: The adherent growing cells were detached by adding Trypsin/EDTA (PAA, Vienna, Austria) followed by a 5 minute incubation in an humidified incubator (37° C., 5% $CO_2$) and centrifugation for 5 minutes at 1,500 rpm. The cells then were washed twice with 10 ml of RPMI-1640 cell culture medium (PAA, Vienna, Austria). The cell number was adjusted to a density of $1 \times 10^5$ cells/ml. From this solution, 100 µl were centrifuged onto microscope slides with a cytospin centrifuge (CYTOSPIN 2, Shandon, UK) for 2 minutes at 50 rpm. The resultant cytospins were dried for at least 2 hours and stained as specified below.

Immunoperoxidase Staining of Cytospins and Cryosections: Cytospins were dried for at least two hours at room temperature or cryosections were dried for at least two hours after they were cut. The sections or cytospins were then fixed for 10 minutes in acetone. The fixed cryosections/cytospins were dried for 30 minutes at room temperature, washed three times with Tris-NaCl (3 grams Tris, 40.5 grams NaCl in 5 litres of distilled $H_2O$ and pH adjusted to 7.4 with HCl), and placed into Tris/NaCl for 5 minutes. The cryosections/cytospins were blocked for 15-30 minutes with 3% milk powder in PBS (100 µl per cryosection/cytospin) and washed three times with Tris-NaCl. The cryosections/cytospins were incubated in 100 µl of primary antibody per cryosection/cytospin (e.g., at 20 µg/ml in 0.5% BSA/PBS; CK 8 at 1:50 in BSA/PBS; CAM 5.2 at 1:10 in BSA/PBS; or RPMI 1640 media (PAA, Vienna, Austria) as a negative control) for 30 minutes in a humidified chamber at room temperature. Following the incubation, the cryosections/cytospins were washed three times with Tris-NaCl.

The cryosections/cytospins were then incubated in 100 µl of a solution containing the secondary antibody (70% PBS+ 30% rabbit or human serum+e.g., 1:50 rabbit anti-mouse antibody, peroxidase coupled or 1:50 rabbit anti-human IgM antibody, peroxidase coupled; Dako, Hamburg, Germany) per cryosection/cytospin for 30 minutes in a humidified chamber at room temperature and washed three times with Tris-NaCl and placed into PBS for 10 minutes. The cryosections/cytospins where then incubated for 10 minutes in 100 µl of a solution containing 0.05% diaminobenzidine and 0.02% hydrogen peroxide (Sigma, Taufkirchen (München), Germany). Following the incubation, the cryosections/cytospins were washed with distilled $H_2O$ and placed into a hematoxylin staining solution (Roth, Karlsruhe, Germany) for 5 minutes. The cryosections/cytospins were then rinsed for 15 minutes under running tap water, washed with distilled $H_2O$ cover with prewarmed glycerol-gelatin.

Glycosidase Assay: Membrane extracts of BXPC-3 cells, prepared by differential centrifugation, were used for glycosylation studies. To cleave all types of N- and O-linked carbohydrate chains, the membrane extract was denaturated in buffer containing 1% sodiumdodecylsulfate and 1% β-mercaptoethanol for 3 min at 95° C. The denaturated extract was diluted with reaction buffer (PBS pH 7.4, 1% nonidet NP-40, 1% β-mercaptoethanol) to the final protein concentration of 0.5 mg/ml. For deglycosylation of O- and N-linked carbohydrates, aliquots of 100 µl were incubated either with 10U N-glycosidase F (Roche Applied Science, Mannheim, Germany) or 5 mU O-glycosidase (Roche Applied Science, Mannheim, Germany) at 37° C. over night. Untreated extract in reaction buffer served as control. The extent of deglycosylation was analyzed by SDS-Page and Western Blotting procedure.

Example 2

This example includes a description of materials and methods used in the studies described in Examples 15 and 16.

Materials: RPMI 1640 and FCS (PAA), silent Fect (Bio-RAD), Cell dissociation solution (Sigma C5789), Si GENOME siRNA (Dharmacon), µMACS, pEolumns, and Protein G Micro Beads and anti human IgM Micro Beads (Miltenyi Biotec).

PBS: 8 g NaCl, 0.2 g KCl, 1.44 g Na2HPO4, and 0.24 g KH2PO4 in 800 ml of distilled H$_2$O.

PBS-Tween: 8 g NaCl, 0.2 g KCl, 1.44 g Na2HPO4, 0.24 g KH2PO4 in 800 ml of distilled H2O, add 400 µl Tween 20.

Lysis buffer 1: 1% Triton, 150 mM NaCl, 50 mM Tris, pH 8.

Hypoton Buffer: 20 mM HEPES pH 7.4, 3 mM KCl, 3 mM MgCl$_2$.

Running buffer: 25 mM Tris, 250 mM Glycin, 0.1% SDS

Transfer buffer: 48 mM Tris, 39 mM Glycine, 20% MeOH pH 9.2, add one mini tablet protease inhibitor per 10 ml (Roche).

Loading dye: 250 mM Tris, 10% SDS, 0.5% Bromophenolblue, 50% Glycerol, 210 mM DTT.

Lysis Buffer for membrane Preparation (2): 150 mM NaCl, 50 mM Tris, 1.5% Triton, 0.5% Na-DOC, 10% Glycerin, 1 mM EDTA, pH 8.0, add one mini tablet protease inhibitor per 10 ml (Roche).

Transfection: BxPc-3 cells were plated in 6-well plates at $2 \times 10^5$ cells/well the day before. At day of transfection two solutions were prepared (per well): 125 µl of serum free medium (SFM) with 5 µl silent Fect, and 125 µl of SFM and 22.5 µl of a 5 µM RNA solution (50 nM final concentration). Both solutions are mixed and incubated for 30 min at RT, and the mix was added dropwise to the cells. Medium was changed after 5-6 hrs. After 48 hrs, cells were once washed with 1×PBS. Cells were harvested in 200 µl lysis buffer 1.

Preparation of whole cell lysate: $9 \times 10^6$ cells (MKN, BxPC, A549) were washed three times with pre-cooled PBS. Cell pellet was resuspended in 1 mL lysis buffer (150 mM NaCl, 1% Triton X-100, 50 mM Tris HCl, pH 8.0). After 30 minutes incubation on ice with occasional mixing cells were centrifuged at 10,000×g at 4° C. to sediment the cell debris. The supernatant was transferred to a fresh 1.5 mL tube.

Preparation of Cell Membrane Extracts: After medium was removed from culture dish, cells were washed three times with pre-cooled PBS. 5 mL pre-cooled PBS was added to a 15 cm culture dish and cells were scraped using a cell scraper. Cell suspension was transferred to a 50 mL tube and centrifuged at 1,300 rpm for 5 minutes. Cell pellets from different culture dishes were collected and again washed with PBS. After centrifugation with 1,300 rpm for 5 minutes cells were resuspended in hypoton buffer (10 mL/1 g cell pellet). The cell suspension was incubated for 30 minutes on ice with vortexing every 5 minutes and then freezed and thawed on liquid nitrogen 5 times. To sediment the cell debris the suspension was centrifuged for 10 minutes at 13,000 rpm at 4° C. The resulting supernatant was then centrifuged in an ultracentrifuge for 45 minutes at 125,000×g at 4° C. The resulting pellet of 4 g of suspension was resuspended in 1 mL lysis buffer and solved with a short pulse (2 sec) sonification. The suspension was centrifuged for 10 minutes at 13,000 rpm at 4° C. and the supernatant containing the membrane fraction transferred to a fresh 1.5 mL tube.

Immunoprecipitation: Immunopurification was performed with µ Columns and µMACS Separator (Miltenyi Biotec). To 150-300 µL membrane preparation or 300-400 µL full lysate, 1.5 µL of monoclonal mouse antibody (anti-nmt55) and 50 µL of Protein G Micro Beads (magnetic labeled) were added and was filled with lysis buffer to a total volume of 800 µL.

The suspension was incubated for 30 minutes rotating with 16 rpm at 4° C. Miltenyi µColumns were placed in the magnetic field of the µMACS Separator. Columns were prepared by rinsing with 200 µL of lysis buffer. Cell lysate was applied onto the column. After the lysate ran through the columns were washed with 5×200 µL lysis buffer. For elution 20 µL of pre-heated (95° C.) 1×SDS gel loading buffer (50 mM Tris HCl, pH 6.8; 50 mM DTT; 1% SDS; 0.005% bromphenol blue; 10% glycerol) was applied onto the column and incubated for 5 minutes at room temperature. A fresh collection tube was placed under the column and the column was eluted with another 50 µL of pre-heated (95° C.) 1×SDS gel loading buffer.

SDS-PAGE: Samples were applied to a 10% SDS-PAGE after addition of 15 µl Loading buffer to 35 µl of lysed cells. 14 µl were loaded per lane, gel ran for 45 min at 40 mA.

Western Blot: The gel was blotted in a wet blotting chamber (BioRad) on a PVDF-membrane (Millipore) for 1 hour at 350 mA. Blots were blocked in 5% dry milk in PBS-Tween for one hour. First antibodies anti-grp78 (1:2000), anti-nmt55 (1:2500) and anti-vimentin (1:1250) were applied for 1 hour in 5% dry milk in PBS-Tween. LM1 C7 (40 µg/ml) was applied for 2 hours. Blots were washed with PBS-Tween three times for 5 minutes and Peroxidase-coupled secondary antibody was applied for one hour. Blots were washed 3 times for 15 minutes and were developed with Pierce ECL Super Signal West Pico solutions.

FACS: Cells were always kept on ice, and ice cold and sterile filtered PBS were used. Cells from transfection are dissolved with cell dissociation solution for 10 minutes, then resuspended in complete growth medium, centrifuged down at 800 g for 5 minutes, cells resuspended in fresh complete medium and counted, cells adjusted to $2 \times 10^5$/ml in complete medium and incubated on ice for 30 min. Dispense 1 ml cells per Eppendorf-tube, wash with PBS, centrifuge down at 800 g at 4° C., resuspend in 500 µl PBS, spin down and then add the first antibody: LM1 at 25 resp. 100 µg/ml, or anti-nmt55 at 1:50 resp 1:25-1:100. Negative controls were isotype control antibody and, without the $1^{st}$ antibody. After antibody incubation, cells were washed once with PBS and secondary antibody (anti-human IgM-FITC (DAKO, F0317) or anti-mouse IgG FITC (dianova, 115-095-008))-Diluted 1:50 in 200 µl, added, and incubated for 30 min (in the dark). Afterwards, cells were washed 2 times with PBS, transferred to a FACS tube in 250 µl PBS. FACS was performed with a FACS Scan (Beckmann-Coulter), and data analysed with the free software WinMDI 2.8.

Cell culture: A549 (carcinomic human alveolar basal epithelial cells) and HEK293 (human embryonal kidney cells) were obtained from ECACC (European collection of cell culture). The growth medium for A549 and HEK293 cells was RPMI 1640 without glutamine (PAA) supplemented with 10% fetal bovine serum, 1% 1-glutamine and antibitotics. Cells were cultured at 37° C., 95% air and 5% CO2, and passaged every 2 to 3 days.

Generation of Nono-sense and -antisense construct: The human Nono cDNA was amplified by polymerase chain reaction (PCR) using the human pancreatic cancer cell line BxPC. cDNA as a template using the following primer set: 5'primer-ATG CAG AGT AAT AAA ACT TTT AAC-3' (SEQ ID NO: 23), and 3'-primer, 5'-GTA TCG GCG ACG TTT GTT TGG GGC-3' (SEQ ID NO: 24). This fragment was ligated by TA cloning into pcDNA3.1-V5-His TOPO TA vector (Invitrogen) yielded into a 50:50 ratio of Nono-sense and -antisense plasmids. Several Nono-sense and -antisense constructs were identified by polymerase chain reaction (PCR) called "pcDNA3.1-V5-His-Nono-6×His-Anti" and "pcDNA3.1-V5-His-Nono-6×His". The sequence direction of PCR product into expression construct was confirmed by DNA sequencing (Qiagen).

Construction of stable cell line: To generate a stable cell line, 5 μg of pcDNA3.1-V5-His-Nono-6×His-Anti or pcDNA3.1-V5-His-Nono-6×His plasmid was transfected, which confers neomycin resistance, into A549 cells using TransPass Transfection reagent (BioLabs) according to the manufacture's instruction. Two days after transfection, cells were selected in 1 mg/ml G418 (PAA) for 2 weeks. Next, G418-resistant clones were selected and analysed of reduced or increased Nono protein expression by western blot using mnt 55-antibody (Dianova) or penta-His antibody (Qiagen). Several positive clones were identified and expanded.

Protein production in bacteria (*E. Coli*): BL21 Star™ (DE2) *E. Coli* were transformed with a plasmid encoding full length transcript of the human Nono gene called "pEXP5-CT-Nono-6×His." Transformants were selected on LB plates containing ampicillin and colonies were then grown overnight at 37° C. in LB medium supplemented with 100 mg/ml amipicillin with shaking at 250 rpm. The overnight culture was diluted 25-fold with fresh LB medium complemented with ampicillin and cultured at 37° C. until an $OD^{600}$ of 0.9 was reached. Protein expression was then induced by addition of 1 mM IPTG (isopropyl-1-thio-β-D-galacto-pyranoside, Invitrogen) and incubation at 37° C. for 3 h. Bacteria were collected by centrifugation and lysed by sonification in a buffer containing 20 mM NaCl, 0.1 M Tris-HCl pH7.8, 10 mM MgCl2, 1/1000 NP-40, 0.5 mM EDTA, 1/10 gycerol, 50 μM PMSF and 0.2 mg/ml lysozyme and antiprotease agents (Complete, Roche). After removal of cell debris by centrifugation (10 min 5000 g), the protein was checked by western blot analysis.

Example 3

This example includes a description of the generation of a cell line expressing LM-1 monoclonal antibody. The following studies were carried out using the materials and methods in Example 1. A description of LM-1 monoclonal antibody heavy and light chain variable region sequences is also included.

As described above, the LM-1 monoclonal antibody expressing hybridoma was obtained by fusing lymphocytes The hybridoma supernatants were screened for antibody production using an ELISA assay. Following ELISA, antibodies were primarily tested immunohistochemically against their autologous tumor for tumor specific reactivity. The LM-1 antibody was generated from the lymphocytes of a patient with lung adenocarcinoma.

Predicted CDRs, of which there are three in each of heavy and light chain, are conveniently denoted herein as LC-CDR1, LC-CDR2 and LC-CDR3; and HC-CDR1, HC-CDR2 and HC-CDR3.

Predicted CDR sequences of LM-1 heavy variable region chain are CDR1, VSGGSISSGGYY (SEQ ID NO: 25), CDR2, YIYYSGSTYYNPSLKS (SEQ ID NO: 26), and CDR3, VDARYDYVWGSYRYDAFDI (SEQ ID NO: 27). CDR1 of the LM-1 heavy chain spans nucleotides 72-105 which encode amino acids 24-35, CDR2 spans nucleotides 153-201 which encode amino acids 52-67, and CDR3 spans nucleotides 300-354 which encode amino acids 100-118.

Predicted CDR sequences of light variable region chain are CDR1; SGSSSNIGNNYVS (SEQ ID NO: 28), CDR2; DNNKRPSG (SEQ ID NO: 29), and CDR3; GTWDSSLSAGWV (SEQ ID NO: 30). CDR1 of lambda light chain spans nucleotides 69-105 which encode amino acids located at positions 23-35. CDR2 spans nucleotides 153-174 which encode amino 5 acids 51-58 and CDR3 spans nucleotides 270-303 and encode amino acids 90-101.

Example 4

This example includes a description of immunohistochemical characterization of an LM-1 antibody. The following studies were carried out using the materials and methods in Example 1.

To characterize the monoclonal antibody secreted by a hybridoma, we tested the antibody against a panel of normal and tumor tissues using an immunoperoxidase assay as described in the materials and methods. This assay provided us with an overview of which tissues were stained by the antibody and of the distribution of the antigen.

Antibodies that are specific for tumor cells and not for normal tissue were further characterized. First, we tested these antibodies against the same types of tumors from different patients. We then tested these antibodies against tumors of other organs and, finally, against normal tissues. Using these assays, we identified the human LM-1 monoclonal antibody. This tumor reactive antibody is of the IgM/λ, isotype (Table 1).

TABLE 1

Origin of the LM-1 Monoclonal IgM Antibody and Clinical Data of Cancer Patients

| Antibody | Organ | Tumour type | Tumour stage | Tumour grade | Age | Sex | Source of Lymphocytes | Ig Class |
|---|---|---|---|---|---|---|---|---|
| LM-1 | Lung | Adenocarcinoma | T2N1 | G3 | 45 | M | Lymph Node | IgM/λ | obtained from the lymph nodes of a cancer patient with the heteromyeloma cell line HAB-1 (Taller, et al., Br. J. Cancer 62:595-598, 1990). The lymphoid sources were not preselected in terms of the age or sex of the patient. The resultant cell is a type of hybridoma known as a trioma, as it is the fusion of three cells. Like normal B-lymphocytes, this trioma has the ability to produce antibodies. The specificity of the antibody is determined by the specificity of the original lymphocyte from the patient that was used to generate the trioma.

To investigate the genetic origin of this human monoclonal IgM antibodies the $V_H$ gene was amplified, cloned and sequenced. The sequence was compared with germline sequences in the IMGT/V-QUEST database to identify the most homologous germ-line genes and to detect somatic mutations. The results are represented in Table 2. The degree of identity of the nucleotide sequences of the $V_H$ segment to those of the closest reported germ-line $V_H$ genes was approximately 99.6% as summarized in Table 2.

TABLE 2

Characterization of Variable Heavy Region of Monoclonal IgM Antibody LM-1 Heavy chain

| Antibody | Germ-line gene | Homology (%) | R/S Frame | R/S CDR |
|---|---|---|---|---|
| LM-1 | IGHV 4-30.01/4-31 *01 | 99.6 | 1/0 | 0/0 |

Genes of the VH4 gene family expressed the LM-1 antibody. The high homology of the VH regions to the germ-line genes and the low RIS ratio, which is an indicator for affinity maturation of antibodies, indicates that none of the antibodies underwent affinity maturation by somatic mutation due to antigen contact. The data indicate that the LM-1 antibody belongs to the family of naturally occurring, non-affinity matured antibodies.

After initial testing on autologous tumors, the reaction patterns of the antibodies were investigated in greater detail using immunohistochemical staining on a variety of paraffin- and cryo-embedded carcinomas and normal tissues. LM-1 antibody exhibited no detectable binding activity with normal tissues (Table 3).

TABLE 3

Reaction Pattern of the Monoclonal IgM Antibody LM-1 on Normal Tissues

| Tissue | LM-1 | CAM 5.2 | M6 (IgM-Control) |
|---|---|---|---|
| Stomach | − | + | − |
| Colon | − | + | − |
| Lung | − | − | − |
| Esophagus | − | − | − |
| Urinary bladder | − | − | − |
| Prostate | − | − | − |
| Breast | − | − | − |
| Pancreas | − | − | − |
| Small Intestine | − | + | − |

In contrast, LM-1 antibody stains a variety of different tumor tissues (Table 4).

TABLE 4

Reaction Pattern of the Monoclonal IgM Antibody LM-1 on Tumor Tissues

| Tissue | Carcinoma type | LM-1 +/− | CAM 5.2 | M6 (IgM-Control) |
|---|---|---|---|---|
| Stomach | Adeno/diffuse | 5/0 | + | − |
|  | Adeno/intestinal | 2/1 | + | − |
| Colon | Adeno | 3/0 | + | − |
| Lung | Adeno | 5/1 | + | − |
|  | Squamos cell | 6/0 | +(CK5/6) | − |
| Esophagus | Squamos cell | 3/0 | +(CK5/6) | − |
|  | Adeno (Barrett) | 4/0 | + | − |
| Pancreas | Adeno | 6/0 | + | − |
| Urinary bladder | Urothel | 1/0 | + | − |
| Kidney | Renal cell | 1/0 | − | − |
| Prostate | Adeno | 7/0 | + | − |
| Breast | Invasive (ductal) | 4/0 | + | − |
|  | Invasive (lobular) | 4/0 | + | − |
| Ovary | Adeno | 3/0 | + |  |
| Uterus | Adeno | 3/0 | + |  |

LM-1 antibody gave a broad staining pattern on a variety of tumor tissues that were tested. The positive control antibodies used in these studies were a mouse monoclonal antibody against human cytokeratin 5/6 ("CK 5/6;" Dako A/S, Denmark) for squamous cell carcinoma of the lung and esophagous and a mouse monoclonal antibody against human cytokeratin ("CAM 5.2;" Becton Dickinson, N.J.). Additional positive control anti-bodies (AE1/AE3 for adenocarcinoma of the colon and antibody CK8 for invasive ductal carcinoma of the breast) were used in the studies.

To examine the antigen recognized by the LM-1 antibody, Western blots were performed with membrane extracts of established lung carcinoma cell line LOU-NH91. Antibody LM-1 reacted with an antigen with an approximate molecular weight of 70 kDa. To rule out non-specific binding of IgM antibodies to membrane extracts, unrelated human control IgM was used as control.

Moreover, the LM-1 monoclonal antibody also specifically stains a number of carcinoma cell lines. In particular, the LM-1 antibody specifically binds lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and lung squamous cell carcinoma cell line LOU-NH91 (DSMZ accession number ACC 393). Slides of these cells were stained according to the cytospin protocol described in the materials and methods section.

Example 5

This example includes a description of cell proliferation inhibition studies of an LM-1 antibody. The following studies were carried out using the materials and methods in Example 1.

Cell proliferation may be assayed by a number of methods that are standard in the art, for example, by the reduction of tetrazolium salts. The yellow tetrazolium salt 3-(4,5-dimethylthiazol-2-yl)-2,5-diphenyltertrazolium bromide ("MTT") (Sigma, St. Louis, Mo.), is reduced by metabolically active cells, in part by the action of mitochondrial dehydogenase enzymes to generate reducing equivalents such as NADH and NADPH. The resulting intracellular purple formazan can be solubilized and quantified by spectrophotometric means. The MTT cell proliferation assay measures the rate of cell proliferation and, when metabolic events lead to apoptosis, the reduction in cell viability.

For the MTT assay, we trypsinized cells and resuspended the cells in 10 ml of RPMI-1460 medium containing 10% Fetal Calf Serum ("FCS") (20% FCS for LOU-NH91), 1% glutamine, and 1% penicillin/streptomycin (complete medium). The cells were then counted and diluted to $1 \times 10^6$ cells/ml. 50 µl of this suspension were pipetted into wells of a 96-well plate, resulting in approximately $5 \times 10^4$ cells/well. The first row of wells was left empty. We then added 50 µl of the antibody diluted in complete medium to each well. The 96-well plate was then incubated for 24 or 48 hours in a 37° C. incubator. After the incubation period, 50 µl MTT solution (5 mg/ml in PBS) were added to each well. The 96-well plate was incubated for 30 minutes at 37° C. and centrifuged for 5 minutes at 800×g. The supernatant was aspirated, 150 µl of dimethylsulphoxide (DMSO) were added to each well, and the cell pellet was resuspended. Absorption was determined at a wavelength of 540 nm and at a reference wavelength of 690 nm in an ELISA reader.

Figure 1:
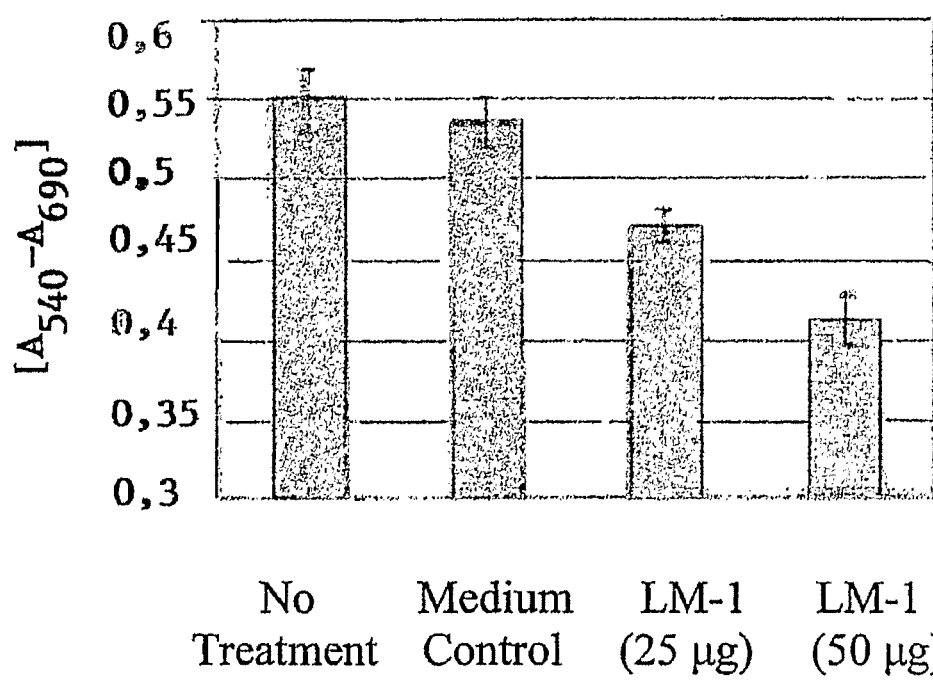
FIG. 1 shows a graph depicting the functional analysis of antibody LM-1 in vitro. The consequences of antibody treatment on the proliferation of different carcinoma cell lines were measured using a 3-(4,5-dimethylthiazol-2-yl)-2,5-diphenyltetrazolium bromide ("MTT") proliferation assay, which shows a concentration dependent inhibition of cell proliferation of LM-1 on lung pancreas carcinoma cell line LOU-NH91. The control for these studies was depleted cell culture supernatant with an unrelated IgM antibodies added at similar concentrations.

As shown in FIG. 1, after 24 hours, monoclonal antibody LM-1 inhibited cell proliferation of lung carcinoma cell line LOU-NH91. In these studies, LOU-NH91 cells were incubated with the LM-1 monoclonal antibody, with depleted supernatant, or without an antibody for 24 hours. The y-axis shows the difference in absorbance at 540 nm and 690 µm ($A_{540}$-$A_{690}$). As is evident from these graphs, incubation with LM-1 monoclonal antibody resulted in a decrease in cell proliferation and cell viability after both a 24 hour and a 48 hour incubation period.

Figure 2:
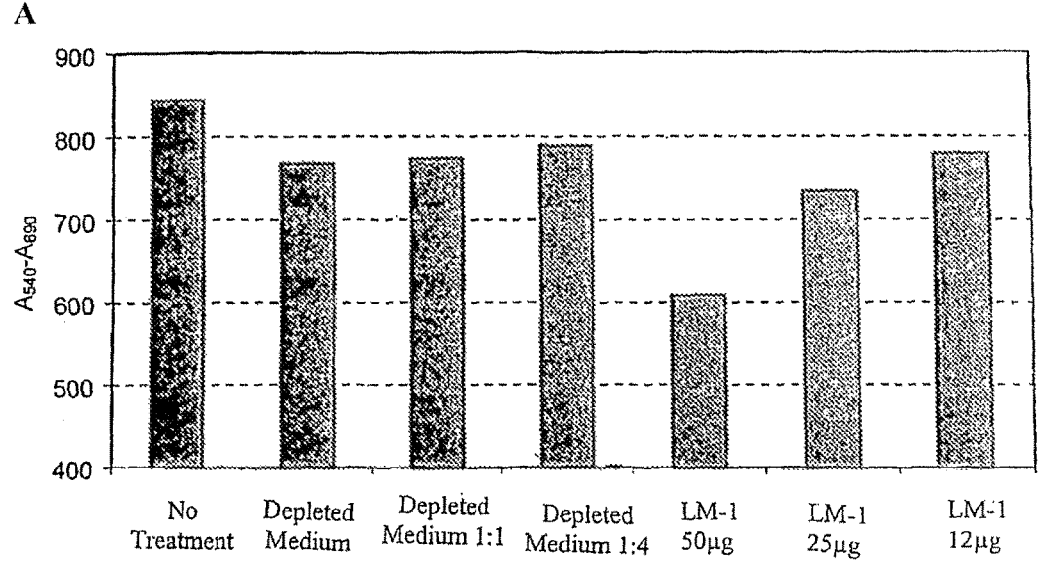
FIGS. 2A and 2B show a series of graphs of the results of MTT reduction assays for mitochondrial dehydrogenase activity showing that the LM-1 monoclonal antibody inhibits cell proliferation and decreases survival, or induces apoptosis of EPLC-272H epidermoid cell carcinoma of the lung cells after A) 24 hours of incubation; and B) 48 hours of incubation.
Figure 2:
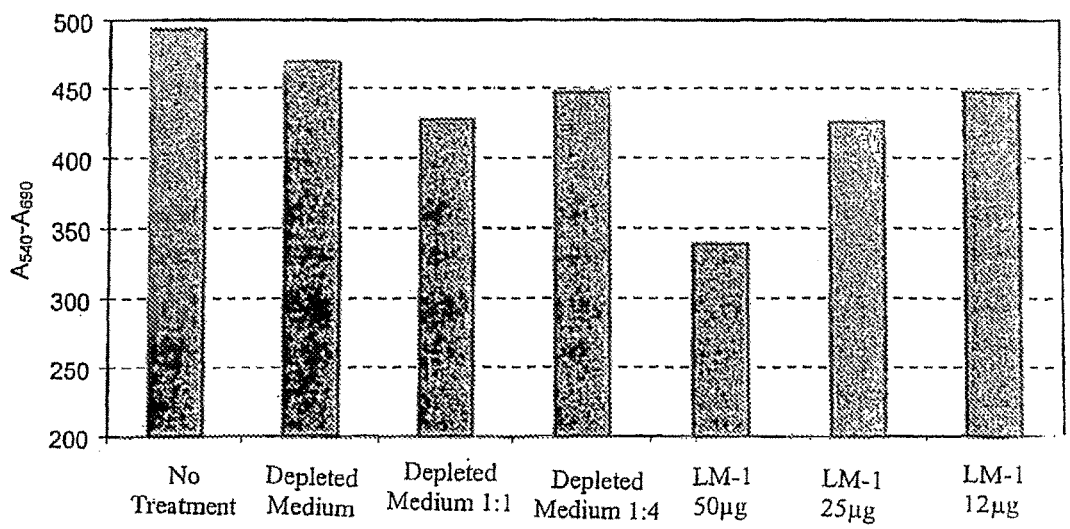

Further exemplary results of such studies are depicted in FIGS. 2A and 2B. After 24 or 48 hours, monoclonal antibody LM-1 inhibited cell proliferation of human epidermoid cell carcinoma cell line EPLC-272H in a concentration-dependent manner, while the controls with depleted cell culture supernatant remained unchanged (FIGS. 2A and 2B).

Example 6

This example includes a description of cell apoptosis studies of an LM-1 antibody. The following studies were carried out using the materials and methods in Example 1.

A number of assays standard in the art maybe used to determine if an antibody induces apoptosis of a cell. For example, we used the CELL DEATH DETECTION ELISA $^{PLUS}$ (Roche, Mannheim, Germany) to analyze the extent to which the LM-1 antibody induce apoptosis. The cell death detection ELISA is based on a quantitative sandwich-enzyme-immunoassay principle using mouse monoclonal antibodies directed against DNA and histones, respectively. This assay allows the specific determination of mono- and oligonucleosomes which are released into the cytoplasm of cells which die from apoptosis.

In particular, 1×10$^4$ tumor cells (LOU-NH91) were plated on 96-well plates and incubated in presence of different concentrations of the human IgM-antibody LM-1 for 24 hours at 37° C. and 7% $CO_2$ in an $CO_2$ incubator. Depleted cell culture supernatant with unrelated IgM antibodies served as negative control.

After the incubation period, the cells were centrifuged for 10 minutes at 200×g and the supernatants were removed. The resulting cell pellets were then incubated with 200 µl lysis-buffer for 30 minutes at room temperature. After centrifugation, 20 µl the supernatants were transferred into a streptavidin-coated microliter plate (MTP) and 80 µl immunoreagent (a mixture of 10% Anti-Histone-Biotin, 10% Anti-DNA-peroxidase (Anti-DNA POD) and 80% incubation buffer) added before incubation for 2 hours at room temperature on a MTP shaker at 250 rpm. Following the incubation period, unbound components were removed by a washing step with incubation buffer. POD was determined photometrically with ABTS™ as a substrate (1 ABTS™ (2,2'-Azino-di[3-ethyl¬ benz-thiazolin-sufonate]) tablet in 5 ml substrate buffer). Antibody-induced apoptosis was measured by determining the color intensity of the green precipitate that it formed as a result of this reaction using an ELISA reader at a wavelength of 415 nm in comparison to ABTS™ solution as a blank (reference wavelength of approximately 490 µl). Based on this color intensity, we calculated the level of the antibody-induced apoptosis.

Figure 3:
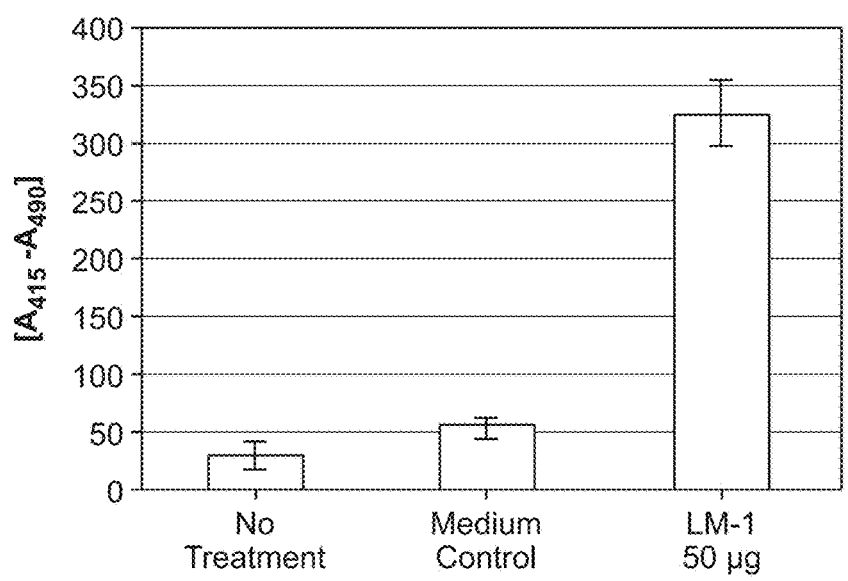
FIG. 3 shows a graph showing that the LM-1 antibody induces apoptosis. In these studies, apoptosis of lung carcinoma cell line LOU-NH91 was detected using the Cell Death Detection ELISA.sup.PLUS apoptosis assay. The control in these studies was depleted cell culture supernatant at a similar concentration.
Figure 4:
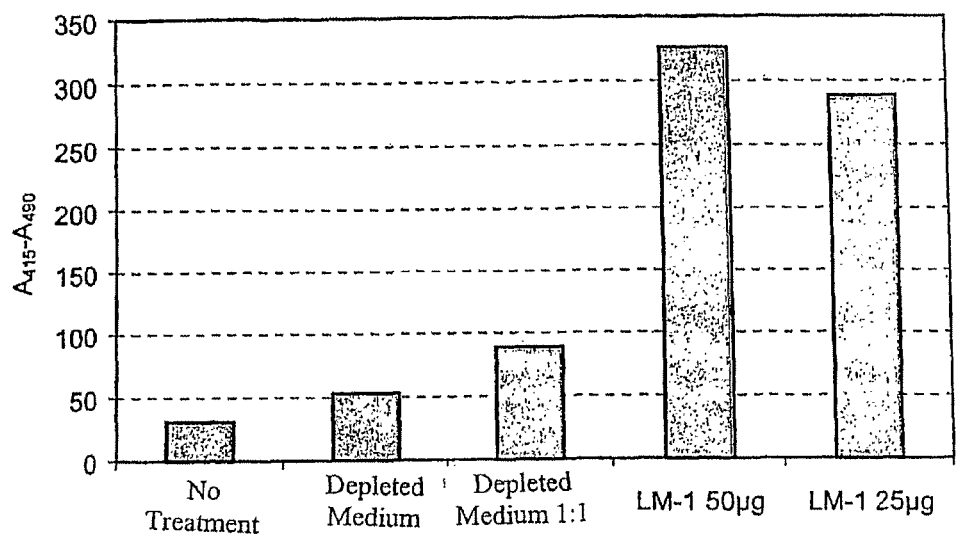
FIGS. 4A and 4B show a series of graphs of the results of a cell death ELISA showing that the LM-1 monoclonal antibody induces apoptosis of LOU-NH91 cells after A) 24 hours of incubation; and B) 48 hours of incubation.
Figure 4:
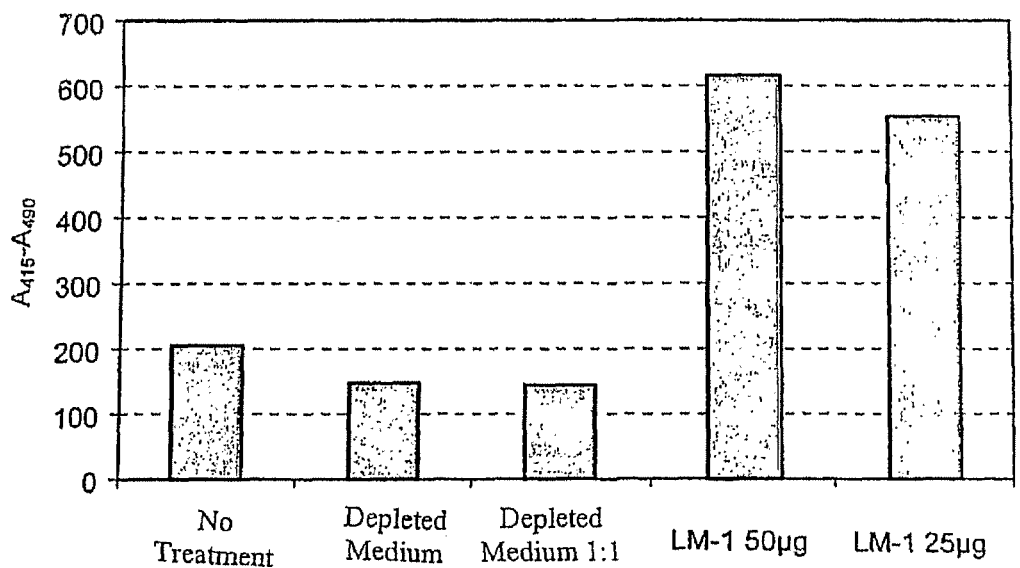

These studies clearly showed that antibody LM-1 induces apoptosis in LOU-NH91 carcinoma cells after 24 hours of incubation (FIGS. 3 and 4A) and after 48 hours of incubation (FIG. 4B). The Y-axis in these figures is the difference between the absorbance at 415 nm and at the 490 nm reference wavelength ($A_{415}$-$A_{490}$) and the medium control is RPMI 1460 medium. The concentration of the LM-1 antibody was either 25 µg or 50 µg/ml in supernatant.

Example 7

This example includes a description of in vivo neoplasm imaging by using an LM-1 antibody.

A patient suspected of having a neoplasm, such as a lung carcinoma, may be given a dose of radioiodinated LM-1 antibody, or another tumor-specific polypeptide, and radiolabeled unspecific antibody using the methods described herein. Localization of the tumor for imaging may be effected according to the procedure of Goldenberg et al. (N. Engl. 7. Med., 298:1384, 1978). By I.V. an infusion of equal volumes of solutions of $^{131}$I-LM-1 antibody and Tc-99m-labeled unspecific antibody may be administered to a patient. Prior to administration of the reagents I.V., the patient is typically pre-tested for hypersensitivity to the antibody preparation (unlabeled) or to antibody of the same species as the antibody preparation. To block thyroid uptake of $^{131}$I, Lugol's solution is administered orally, beginning one or more days before injection of the radioiodinated antibody, at a dose of 5 drops twice or three-times daily. Images of various body regions and views may be taken at 4, 8, and 24 hours after injection of the labeled preparations. If present, the neoplasm, e.g., a colorectal carcinoma, is detected by gamma camera imaging with subtraction of the Tc-99m counts from those of $^{131}$I, as described for $^{131}$I-labeled anti-CEA antibody and Tc-99m-labeled human serum albumin by DeLand et al. (Cancer Res. 40:3046, 1980). At 8 hours after injection, imaging is usually clear and improves with time up to the 24 hour scans.

Example 8

This example includes a description of neoplasm treatment by using an LM-1 antibody, such as labeled antibody mixtures.

A patient diagnosed with a neoplasm, for example, a lung carcinoma, may be treated with the polypeptides of the invention as follows. Lugol's solution may be administered, e.g., 7 drops 3 times daily, to the patient. Subsequently, a therapeutic dose of $^{131}$I-LM-1 antibody may be administered to the patient. For example, a $^{131}$I dose of 50 mCi may be given weekly for 3 weeks, and then repeated at intervals adjusted on an individual basis, e.g., every three months, until hematological toxicity interrupts the therapy. The exact treatment regimen is generally determined by the attending physician or person supervising the treatment. The radioiodinated antibodies may be administered as slow I.V. infusions in 50 ml of sterile physiological saline. After the third injection dose, a reduction in the size of the primary tumor and metastases may be noted, particularly after the second therapy cycle, or 10 weeks after onset of therapy.

Example 9

This example includes a description of neoplasm treatment by using conjugated antibodies.

A patient diagnosed with a neoplasm, for example, a patient with a lung carcinoma that has metastasized to the chest, may be treated with solutions of $^{131}$I-LM-1, $^{10}$B-LM-1, and a Tc-99m labeled unspecific antibody. An amount of $^{131}$I-labeled LM-1 antibody (in 50 ml of sterile physiological saline) sufficient to provide 100 MCi of $^{131}$I activity based on a 70 kg patient weight may be administered to the patient. This dosage is equal to 3.3 mg of an antibody having 40-80 Boron atoms and 8-16 Boron-10 atoms per antibody molecule. The neoplasm is first precisely localized using the procedure of Example 6. In addition, Lugol's solution should be continuously administered to the patient, as in the previous example. A well-collimated beam of thermal neutrons may then be focused on the defined tumor locations. Irradiation with an external neutron beam dose of 400-800 rads, delivered in a period of from 8-20 min, is effected for each tumor locus, and is optionally repeated with administration of the tumor-locating antibody, with or without the radiolabel, at intervals adjusted on an individual basis, but usually not exceeding a total dose of 3200 rads unless simultaneous external irradiation therapy is indicated. If desired, in addition to this therapy, an anti-tumor agent, such as a chemotherapeutic agent, may also be administered to the patient.

Example 10

This example includes a description of additional immunohistochemical characterization of LM-1 antibody.

Immunohistochemistry analysis revealed that LM-1 antibody binds to various forms of cancer. For example, LM-1 binds to all grades and stages of lung adenocarcinoma tested, and no differences between males or females were detected. In particular, LM-1 antibody binds to lung adenocarcinoma at UICC stages of IA, IB, IIB, IIIA and IIIB (e.g., pT1pNoG1, pT1G2, pT1pNxG2, pT1pNoG2, pT1pNoG3, pT2pNo, pT2pNoG1, pT2G2, pT2pNoG2, pT2pN1G2, pT2pNoG3, pT2pN1G1, pT2pN1G3, pT3pNxG3, pT3pN1G3, pT1pN2G2, pT2pN2G2, pT2pN2G3, pT1pN3G1 and pT4pNoG2) with a high percentage of cells of each stage staining positive for LM-1 (greater than 40%, 50% or 60%, typically 90% or greater).

LM-1 also binds to all grades and stages of lung squamous cell carcinoma tested, and no differences between males or females were detected. In particular, LM-1 antibody binds to lung squamous cell carcinoma at UICC stages of IA, IIA, IB, IIB, IIIA, IIIB and IV (e.g., pT1G2, pT1pNoG1, pT1pNoG2, pT1pNoMoG3, pT1pNoG3, pT1pN1G3, pT1pN2G3, pT2pNoG2, pT2pNxG2, pT2pN1G2, pT2G3, pT2pNoG3, pT2pN1G3, pT2pN2G2, pT2pN2G3, pT3pNoG2, pT3pN1G2, pT3pN2G3, pT4pN1G3, pT2pN0pM1G2 and pT3pN0pM1G2) with a high percentage of cells of each stage staining positive for LM-1 (greater than 30%, typically 90% or greater).

LM-1 further binds to all grades and stages of colon adenocarcinoma tested, and no differences between males or females were detected. In particular, LM-1 antibody binds to colon adenocarcinoma at UICC stages of I, IIA, IIB, IIIA, IIIB and IIIC (e.g., pT1pNoG1, pT1pNoG2, pT2pNo, pT2pNoG2, pT2pNoG3, pT3pNoG2, pT3pNoG3, pT4pNoG3, pT2pN1G2, pT4pN1G2, pT3pN1G2, pT3pN2G2, pT3pN1G3, pT3pN1G2, pT2pN2G2 and pT3pN2G2) with a high percentage of cells of each stage staining positive for LM-1 (greater than 30%, typically 90% or greater).

LM-1 additionally binds to all grades and stages of pancreas adenocarcinoma tested, and no differences between males or females were detected. In particular, LM-1 antibody binds to pancreas adenocarcinoma at UICC stages of I, II, III, IVA and IVB (e.g., pT1pNo, pT3pNoG2, pT3pNoG3, pT2pN1G3, pT3pN1G2, pT3pN1G3, pT3pN1aG2, pT3pN1aG2-3, pT3pN1bG1, pT3pN1bG2, pT3pN1bG2-3, pT3pN1bG3, pT4pN1b, pT3pNopM1G2, pT4pN1bpM1G2 and pT4pN1bpM1G3), and on endocrine tumors, with a high percentage of cells of each stage staining positive for LM-1 (greater than 30%, typically 90% or greater).

Thus, LM-1 antigen is therefore ubiquitously expressed on all grades and stages of lung adenocarcinoma, lung squamous cell carcinoma, colon adenocarcinoma and pancreas adenocarcinoma of both males and females. LM-1 antigen is therefore a target and LM-1 antibodies and functional fragments thereof a therapy for treating all stages of lung adenocarcinoma, lung squamous cell carcinoma, colon adenocarcinoma and pancreas adenocarcinoma in both males and females.

Immunohistochemistry analysis also revealed that LM-1 antibody binds to various metastatic forms of cancer. In particular, LM-1 binds to lymph node and brain metastasis arising from lung adenocarcinoma and lung squamous cell carcinoma. LM-1 also binds to lymph node metastasis arising from breast invasive ductal and invasive lobular cancer. LM-1 further binds to liver metastasis, lung metastasis and lymph node metastasis arising from colon adenocarcinoma. LM-1 additionally binds to lymph node metastasis arising from stomach adenocarcinoma (intestinal and diffuse), arising from pancreas adenocarcinoma and arising from head and neck squamous cell carcinoma. LM-1 antigen is therefore a target and LM-1 antibodies and functional fragments thereof a therapy for reducing or inhibiting establishment or formation of metastatic tumors, or growth of established metastatic tumors, arising from these and other cancers, and reducing the risk of cancer relapse or progression to metastatic tumor formation or establishment, or growth or proliferation of established or formed metastasis.

Immunohistochemistry analysis also revealed that LM-1 antibody did not detectably bind to various healthy non-cancerous tissues. In particular, LM-1 did not detectably binds to stomach (glandular), colon (epithelial), lung (glandular or alveolar), esophagus (epithelial), pancreas (glandular), liver (glandular), kidney (epithelial), prostate (glandular), testis (germinal), breast (glandular), uterus (epithelial), ovary (glandular), small intestine (epithelial), bladder (epithelial), or adrenal gland (endocrine). LM-1 also did not detectably bind to cerebellum, cerebral cortex, endothelium, retina, fallopian tube, heart, kidney, lymph node, pancreas, thyroid, parathyroid, pituitary, placenta, skin, spleen, muscle or thymus.

Example 11

This example includes a description of studies profiling carbohydrate (N-glycan) present on LM-1 antibody, as represented by an antibody produced by a hybridoma depsoied as DSMZ Depsoit No. DSM ACC2623, deposited on Nov. 6, 2003, or as represented by an antibody having heavy and light chain variable region sequences set forth as SEQ ID NOs:1, 3, 5 or 7, and 11.

In brief, LM-1 obtained from human/mouse hybridomas was evaluated for presence of typical non-human glycan structures. Human and non-human mammalian glycan structures can be distinguished based upon sialylated glycans: Sialylated glycans of human origin contain only Neu5Ac as sialic acid, while rodents and most other mammals also integrate Neu5Gc into sialylated structures.

MALDI-TOF MS analysis of liberated permethylated N-glycans was used to determine the structures that are present on the antibodies. Replacement of one Neu5Ac residue by Neu5Gc in a permethylated glycan introduces a mass shift of 30 Da. For MALDI-TOF analysis of permethylated glycans, 1.4 mg of LM-1 was digested with PNGase F and liberated glycans purified. After permethylation, glycans were analysed by MALDI-TOF MS.

Figure 5:
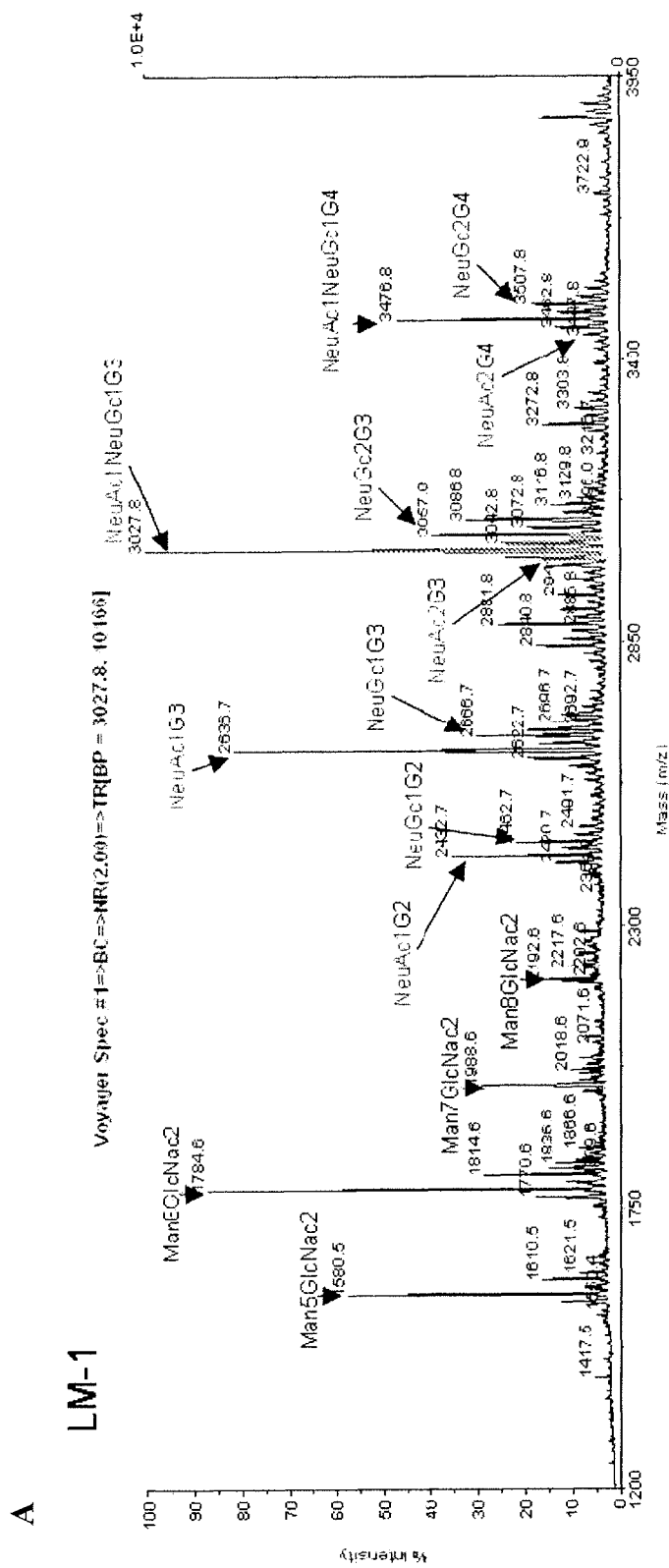
FIGS. 5A-5F show A) MALDI-TOF spectra for LM-1; and the results of screening for antibody LM-1 binding to B) mono-saccharides, C) di-saccharides, D) tri-saccharides, E) tetra-saccharides and F) oligosaccharides.

The MALDI-TOF spectra for LM-1 is shown in FIG. 5A. Man5GlcNAc2 to Man8GlcNAc2 represent high mannose type glycans. The other structures correspond to:
NeuAc1G1: NeuAc1Gal1GlcNAc1Man5GlcNAc2
NeuGc1G1: NeuGc1Gal1GlcNAc1Man5GlcNAc2
NeuAc1G2: NeuAc1Gal2GlcNAc2Man3GlcNAc2
NeuGc1G2: NeuGc1Gal2GlcNAc2Man3GlcNAc2
NeuAc1G3: NeuAc1Gal3GlcNAc2Man3GlcNAc2
NeuGc1G3: NeuGc1Gal3GlcNAc2Man3GlcNAc2
NeuAc2G3: NeuAc2Gal3GlcNAc2Man3GlcNAc2
NeuAc1NeuGc1G3:
   NeuAc1NeuGc1Gal3GlcNAc2Man3GlcNAc2
NeuGc2G3: NeuGc2Gal3GlcNAc2Man3GlcNAc2
NeuAe2G4: NeuAe2Gal4GlcNAc3Man3GlcNAc2
NeuAc1NeuGc1G4:
   NeuAe1NeuGc1Gal4GlcNAc3Man3GlcNAc2
NeuGc2G4: NeuGc2Gal4GlcNAc3Man3GlcNAc2

Only the most dominant glycan structures are indicated in FIG. 5A. All identified glycan structures are listed in TABLE 5:

| Glycan structure Arnold et al. | m/z | LM-1 |
|---|---|---|
| Man5GlcNAc2 5.6% | 1580.5 | +++ |
| Man6GlcNAc2 9.5% | 1784.5 | ++++ |
| Man7GlcNAc2 3.2% | 1989.5 | +++ |
| Man8GlcNAc2 4.1% | 2193.5 | +++ |
| Man9GlcNAc2 1% | 396.6 | + |
| GlcNAc1Man3GlcNAc2 0.9% | 1417.5 | + |
| GlcNAc1Man4GlcNAc2 | 1621.5 | + |
| GlcNAc1Man6GlcNAc2 | 2029.5 | + |
| GlcNAc1Man7GlcNAc2 | 2233.5 | + |
| Gal1GlcNAc2Man3GlcNAc2 1.1% | 1621.5 | + |
| Gal1GlcNAc2Man4GlcNAc2 0.7% | 1825.6 | + |
| Gal2GlcNAc2Man3GlcNAc2 | 2070.5 | + |
| Man4GlcNAc2Fuc1 | 1550.4 | + |
| Man6GlcNAc2Fuc1 | 1995.5 | + |
| GlcNAc1Man3GlcNAc2Fuc1 | 1591.5 | + |
| GlcNAc2Man3GlcNAc2Fuc1 (G0F) 0.2% | 1836.6 | + |
| Gal1GlcNAc1Man3GlcNAc2Fuc1 | 1795.5 | + |
| Gal1GlcNAc2Man3GlcNAc2Fuc1 (G1F) 0.4% | 2040.5 | + |
| Gal2GlcNAc2Man3GlcNAc2Fuc1 (G2F) 1.1% | 2245.6 | + |
| Gal3GlcNAc3Man3GlcNAc2Fuc1 | 2695.6 | + |
| Gal4GlcNAc3Man3GlcNAc2Fuc2 | 3072.6 | + |
| NeuAc1Gal2GlcNAc1Man3GlcNAc2 1.9% | 2186.5 | ++ |
| NeuGc1Gal2GlcNAc2Man3GlcNAc2 | 2217.5 | ++ |
| NeuAc1Gal1GlcNAc1Man5GlcNAc2 | 2391.6 | ++ |
| NeuGc1Gal1GlcNAc1Man5GlcNAc2 | 2421.6 | ++ |
| NeuAc1Gal2GlcNAc2Man3GlcNAc2 1.7% | 2432.7 | +++ |
| NeuGc1Gal2GlcNAc2Man3GlcNAc2 | 2462.7 | ++ |
| NeuAc1Gal3GlcNAc2Man3GlcNAc2 | 2636.6 | ++++ |
| NeuGc1Gal3GlcNAc2Man3GlcNAc2 | 2696.6 | +++ |
| NeuAc1Gal4GlcNAc2Man3GlcNAc2 | 2840.6 | ++ |
| NeuGc1Gal4GlcNAc2Man3GlcNAc2 | 2870.6 | ++ |
| NeuAc2Gal3GlcNAc2Man3GlcNAc2 | 2997.6 | +++ |
| NeuAc1NeuGc1Gal3GlcNAc2Man3GlcNAc2 | 3027.6 | ++++ |
| NeuGc2Gal3GlcNAc2Man3GlcNAc2 | 3057.6 | +++ |
| NeuAc2Gal4GlcNAc3Man3GlcNAc2 | 3243.7 | ++ |
| NeuAc1NeuGc1Gal4GlcNAc3Man3GlcNAc2 | 3273.7 | +++ |
| NeuGc2Gal4GlcNAc3Man3GlcNAc2 | 3303.7 | ++ |
| NeuAc2Gal4GlcNAc3Man3GlcNAc2 | 3447.7 | + + |
| NeuAc1NeuGc1Gal4GlcNAc3Man3GlcNAc2 | 3477.7 | ++ |
| NeuGc2Gal4GlcNAc3Man3GlcNAc2 | 3507.7 | + |
| NeuAc2Gal2GlcNAc2Man3GlcNAc2Fuc1 2.6% | 2967.6 | ++ |
| NeuAc1NeuGc1Gal2GlcNAc2Man3GlcNAc2Fuc1 | 2997.6 | +++ |
| NeuGc2Gal2GlcNAc2Man3GlcNAc2Fuc1 | 3027.6 | +++ |

++++) >5%;
+++) 2-5%;
++) 1-2%;
+ <1%

Detailed analysis of N-glycans on LM-1 was compared to data published in Arnold et al. (J. Biol. Chem. 280:29080 (2005)). Glycoprofiling of LM-1 antibody shows a complex glycan pattern. There is a significant content of high mannose structures (Man5 to Man9) and also a significant amount of sialylated glycans. Galactosylated and fucosylated glycans (e.g., G1, G2, G0F, G1F and G2F) constitute only a minor fraction of glycans. The glycan composition of LM-1 is comparable to data published by Arnold et al. on the glycosylation of human serum IgM. There are however differences in glycoforms.

The MALDI-TOF MS analysis (FIG. 5A) demonstrates the presence of both NeuAc and NeuGc on the different sialylated N-glycans. For each of the sialylated glycans, isoforms with NeuAc, NeuGc or both sialic acids are present.

Example 12

This example includes data that appears to show binding of LM-1 to a carbohydrate target antigen. This example also includes a description of binding studies with LM-1 antibody against a library of carbohydrates, and blood group antigens.

LM-1 antibody binds to a number of various tumor cells, such as one or more of a lung adenocarinoma cell line Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), and a lung squamous cell carcinoma cell line LOU-NH91 (DSMZ accession number ACC 393). Tumor cells were treated with N-glycosidase and then analyzed for binding of LM-1 to the cells, as described in Example 1.

Although the data indicate that LM-1 binding to N-glycosidase treated cells was significantly reduced, suggesting possible involvement of a carbohydrate moiety in the epitope to which LM-1 binds, subsequent data described in Example 16 indicates that LM-1 binds to a bacterially expressed antigen, meaning that carbohydrates are not necessary for LM-1 binding to antigen.

A panel of carbohydrates was screened for binding of LM-1 antibody. In particular, the panel included mono-, di-, tri, tetra- and oligosaccharides conjugated to a paolyacrylamide spacer. The carbohydrates, number of saccharides in the carbohydrates and spacer type are listed in TABLE 6.

TABLE 6

Carbohydrate conjugates

| number | carbohydrate structure | short name | number saccharides | spacer |
|---|---|---|---|---|
| 0 | HOCH$_2$(HOCH)$_4$CH$_2$NH— | aminoglucitol | | |
| 1 | GalNAcβ1-4GlcNAcβ | Lac-di-Nac | di | 1 |
| 2 | GlcNAcβ1-3Galβ- | GlcNacβ3Gal | di | 2 |
| 3 | GlcNAcβ1-6(GlcNAcβ1-3)Galβ1- | Tk | tetra | 2 |
| 4 | GalNAcβ1-4Galβ1-4Glcβ- | GA1 | tri | 1 |
| 5 | GalNAcα1-3(Fucα1-2)Galβ1-4GlcNAcβ- | A type 2 | tetra | 1 |
| 6 | Galα1-3(Fucα1-2)Galβ1-4GlcNAcβ- | B type 2 | tetra | 1 |
| 7 | Galα1-3Galβ1-4Glcβ- | Galα1-3'Lac | tri | 2 |
| 8 | GlcNAcβ1-2Galβ1-3GalNAcα- | GlcNAcβ1-2'TF | tri | 1 |
| 9 | Galα1-4GlcNAcβ- | Galα4GlcNAc | di | 1 |
| 10 | Neu5Acβ- | β-N-acetylneuraminic acid | mono | 3 |
| 11 | Glcα1-4Glcβ- | maltose | di | 1 |
| 12 | Glcα- | α-D-glucose | mono | 1 |
| 13 | Glcβ- | β-D-glucose | mono | 1 |
| 14 | Galα- | α-D-galactose | mono | 1 |
| 15 | Galβ- | β-D-galactose | mono | 1 |
| 16 | Manα- | α-D-mannose | mono | 1 |
| 17 | 6-H$_2$PO$_3$Manα- | α-D-mannose-6- | mono | 1 |
| 18 | Fucα- | α-L-fucose | mono | 1 |
| 19 | β-D-GlcNAc- | β-N-acetyl-D-glucosamine | mono | 1 |
| 20 | α-D-GalNAc- | α-N-acetyl-D- | mono | 1 |
| 21 | β-D-GalNAc- | β-N-acetyl- | mono | 1 |
| 22 | Manα1-3(Manα1-6)Manα- | Man$_3$ | tri | 1 |
| 23 | 3-O-su-Galβ- | β-D-galactose-3-sulfate | mono | 1 |
| 24 | Neu5Acα- | α-N-acetylneuraminic acid | mono | 3 |
| 25 | Neu5Acα2-3Galα1-4GlcNAcβ- | 3'SLN | tri | 1 |
| 26 | Galα1-4Galβ1-4Glcβ- | P$_k$, Gb$_3$ | tri | 2 |
| 27 | Galα1-3GalNAcβ- | Tαβ | di | 1 |
| 28 | Galβ1-3Galβ- | Galβ3Gal | di | 1 |
| 29 | Galβ1-3(Fucα1-4)GlcNAcβ- | Le$^a$ | tri | 1 |
| 30 | Fucα1-2Galβ1-3(Fucα1-4)GlcNAcβ- | Le$^b$ | tetra | 1 |
| 31 | Fucα1-2Galβ1-3GlcNAcβ- | Le$^d$, H type 1 | tri | 1 |
| 32 | Galβ1-3GlcNAcβ- | Le$^c$ | di | 1 |
| 33 | Galβ1-4(Fucα1-3)GlcNAcβ- | Le$^x$ | tri | 1 |
| 34 | Fucα1-2Galβ1-4(Fucα1-3)GlcNAcβ- | Le$^y$ | tetra | 1 |
| 35 | Galβ1-4Glcβ- | Lac | di | 1 |
| 36 | Galβ1-4GlcNAcβ- | LacNAc | di | 1 |
| 37 | Galβ1-3GalNAcα- | TF | di | 1 |
| 38 | Fucα1-3GlcNAcβ- | Fucα3GlcNAc | di | 1 |
| 39 | Fucα1-4GlcNAcβ- | Fucα4GlcNAc, Le | di | 1 |
| 40 | GalNAcα1-3GalNAcβ- | Fs-2 | di | 1 |
| 41 | GalNAcα1-3GalNAcα- | core 5 | di | 1 |
| 42 | Galα1-3GalNAcα- | Tαα | di | 1 |
| 43 | Neu5Acα2-3Galβ1-3GlcNAcβ- | 3'-SiaLe$^c$ | tri | 1 |
| 44 | Galα1-2Galβ- | Galα2Gal | di | 1 |
| 45 | Galβ1-3GalNAcβ- | Tββ | di | 1 |
| 46 | GlcNAcβ1-4GlcNAcβ- | (GlcNAc)$_2$ | di | 1 |
| 47 | Neu5Acα2-6GalNAcα- | sTn | di | 1 |
| 48 | Fucα1-2Galβ1-3GalNAcα- | H type 3 | tri | 1 |
| 49 | Neu5Acα2-3Galβ1-4Glcβ- | 3'-SL | tri | 3 |
| 50 | Neu5Acα2-3Galβ1-3(Fucα1-4)GlcNAcβ- | sLe$^a$ | tetra | 1 |
| 51 | Neu5Acα2-3Galβ1-4(Fucα1-3)GlcNAcβ- | sLe$^x$ | tetra | 1 |
| 52 | Neu5Acα2-6Galβ1-4Glcβ- | 6'-SL | tri | 3 |
| 53 | 6-O-su-GlcNAcβ- | β-N-acetyl-D-glucosamine- | mono | 1 |
| 54 | O-su-3Galβ1-3(Fucα1-4)GlcNAcβ- | 3'-O-su-Le$^a$ | tri | 1 |
| 55 | O-su-3Galβ1-4(Fucα1-3)GlcNAcβ- | 3'-O-su-Le$^x$ | tri | 1 |
| 56 | 3'-O-su-LacNAcβ- | 3'-su-LacNAc | di | 1 |
| 57 | 3'-O-su-Galβ1-3GLcNAcβ- | 3'-su-Le$^c$ | di | 4 |

TABLE 6-continued

Carbohydrate conjugates

| number | carbohydrate structure | short name | number saccharides | spacer |
|---|---|---|---|---|
| 58 | Galα1-6Glcβ- | melibiose | di | 1 |
| 59 | Galα1-3Galβ1-4GlcNAcβ- | Galα1-3'LacNAc | tri | 1 |
| 60 | GlcNAcα1-3Galβ1-3GalNAcα- | GlcNAcα1-3'TF | tri | 1 |
| 61 | Neu5Acα2-8Neu5Acα2 | (Sia)$_2$ | di | 1 |
| 62 | Neu5Acα2-8Neu5Acα2-8Neu5Acα2 | (Sia)$_3$ | tri | 1 |
| 63 | GlcNAcβ1-3Galβ1-3GalNAcα- | GlcNAcβ1-3'TF | tri | 1 |
| 64 | Galβ1-2Galβ- | Gal2βGal | di | 1 |
| 65 | Galβ1-4(6-O-su)GlcNAcβ- | 6-O-su-LacNAc | di | 1 |
| 66 | Galβ1-3(GlcNAcβ1-6)GalNAcα- | core 2 | tri | 1 |
| 67 | Fucα1-2Galβ1-3GalNAcβ- | H type 4 | tri | 1 |
| 68 | Galβ1-3GlcNAcβ1-3Galβ1-4GlcNAcβ- | LNT | tetra | 2 |
| 69 | Galβ1-4GlcNAcβ1-3Galβ1-4GlcNAcβ- | LNnT | tetra | 2 |
| 70 | Neu5Acα2-3Galβ- | GM4 | di | 1 |
| 71 | Neu5Acα2-6Galβ- | Neu5Ac6Gal | di | 1 |
| 72 | GalNAcα1-3(Fucα1-2)Galβ- | A$_{tri}$ | tri | 4 |
| 73 | Galα1-3(Fucα1-2)Galβ- | B$_{tri}$ | tri | 1 |
| 74 | GalNAcα1-3Galβ- | A$_{di}$ | di | 1 |
| 75 | Galα1-3Galβ- | B$_{di}$ | di | 1 |
| 76 | Fucα1-2Galβ1-4GlcNAcβ- | H type 2 | tri | 1 |
| 77 | 6'-su-LacNAcβ- | 6'-O-su-LacNAc | di | 1 |
| 78 | Fucα1-2Galβ- | H$_{di}$ | di | 1 |
| 79 | 3'-O-su-Galβ1-3GalNAcα- | 3'-O-su-TF | di | 1 |
| 80 | GlcNAcβ1-3Galβ1-4GlcNAcβ | GlcNAcβ1-3'LacNAc | tri | 2 |
| 81 | GalNAcβ1-3GalNAcβ- | di-GalNAcβ | di | 1 |
| 82 | Neu5Acα2-3Galβ1-3GalNAcα- | 3'-SiaTF | tri | 1 |
| 83 | GlcNAcβ1-3GalNAcα- | core 3 | di | 1 |
| 84 | GlcNAcβ1-6GalNAcα- | core 6 | di | 1 |
| 85 | GlcNAcβ1-3(GlcNAcβ1-6)GalNAcα- | core 4 | tri | 1 |
| 86 | Neu5Acα2-6(Neu5Acα2-3Galβ1- | Sia$_2$TF | tetra | 1 |
| 88 | Neu5Acα2-6Galβ1-4GlcNAcβ1-2Manα1-6(Neu5Acα2-6Galβ1-4GlcNAcβ1-2Manα1-3)Manβ1-4GlcNAcβ1-4GlcNAcβ- | YDS | oligo | 3 |
| 89 | Galβ1-4GlcNAcβ1-2Manα1-6(Galβ1-4GlcNAcβ1-2Manα1-6)Manβ1-4GlcNAcβ1-4GlcNAcβ- | 9-OS | oligo | 3 |
| 90 | GlcNAcβ1-2Manα1-6(GlcNAcβ1-2Manα1-3)Manβ1-4GlcNAcβ1-4GlcNAcβ- | 7-OS | oligo | 3 |
| 91 | Neu5Acα2-3(Neu5Acα2-6)GalNAcα- | 3,6-SiaTn | tri | 1 |
| 93 | Neu5Acα2-3Galβ1-4GlcNAcβ- | 6'-SLN | tri | 1 |

Spacers: 1 = carbohydrate-HOCH2CH2CH2NH2—; 2 = carbohydrate-HOCH2CH2NH—; 3 = carbohydrate-NHCOCH2NH—; and 4 = carbohydrate-O(CH2)3NHCO(CH2)5NH—

Screening was performed by ELISA. Briefly, carbohydrate conjugates were immobilized on a 96 well microtiter plate, blocked with 2% bovine serum albumin and incubated in a first step with the primary antibody. Detection was performed by incubating with the POD-labelled secondary rabbit anti-human IgM antibody (Dianova, code 309-035-095), development with TMB-microwell peroxidase substrate (tebu-bio, code TMB-500) for 15 minutes, and OD measurement at 450 nm against 630 nm as a reference wave length. Each probe was investigated in duplicate.

First studies were performed against a panel of 6 conjugates to find the individual antibody dilutions for the test, because positive signals should be in the OD range of 0.5 to 1.0. Moreover, two types of control studies were performed to prove the carbohydrate specificity of the obtained signals and to exclude unspecific artifacts: (i) the use of the aminoglucitol-conjugate (number 0) as a chemically comparable but non-carbohydrate antigen, and (ii) a preincubation of the carbohydrate conjugate with periodate according to Woodward (Woodward et al., J. Immunol. Meth 78:143 (1985)), which alters the carbohydrate structure. A decreased signal intensity therefore detects a carbohydrate specificity of antibody binding.

Additionally, a commercially available human IgM antibody that does not bind carbohydrates was investigated against a panel of 6 conjugates as a negative control. The studies included blank controls for each conjugate on each individual microtiter plate. Blanks represent wells without incubation with the primary antibody.

Screening was performed with a single concentration, 0.5 µg/ml LM-1, 2 µg/ml hIgM negative control, and a 1:20 dilution for the Nemod-TF2 control antibody which represents a concentration of less than 0.1 µg/ml. The NM-TF2 antibody was tested against the Galβ1-3GalNAcα-conjugate (Table 6, number 37) which is strongly recognized by this antibody. Signal intensity was always measured to a OD of more than 4.

Signal intensity of blank probes was always measured at OD<0.020. FIGS. 5B-5F show results of screening for antibody LM-1 are illustrated with respect to binding to mono-(FIG. 5B), di-(FIG. 5C), tri-(FIG. 5D), tetra-(FIG. 5E) and oligosaccharide-(FIG. 5F) conjugates, as listed in Table 6. Control bars are in order, the blank, the non-carbohydrate conjugate (Table 6, number "0"), and the positive control Nemod-TF2.

Screening revealed a low signal intensity despite high antibody concentrations compared to the positive control antibody Nemod-TF2. Moreover relatively high binding was measured for the non-carbohydrate control (0), which was not the case for the Nemod-TF2. Nevertheless binding to charged carbohydrate conjugates seemed to be enhanced as compared to uncharged carbohydrate conjugates. However, again, the data in Example 16 indicate that carbohydrates are not necessary for LM-1 binding to antigen.

To check the specificity of the signals as well as to discriminate from a high background three additional studies were performed. The conjugate 6OsuLacNAc (Table 6, number 77) was selected for these studies because the signal intensity against this conjugate was enhanced. The positive control antibody Nemod-TF2 was additionally investigated against the Galβ1-3GalNAcα-conjugate (Table 6, number 37):

(i) Binding of antibody in a series of different concentrations against the conjugate 6OsuLacNAc (Table 6, number 77), starting with a concentration where all coated antigen is bound (saturation concentration). Measurement of concentration dependent binding was started with antibody concentrations which result in maximum binding under the ELISA conditions used. LM-1 (20 µg/ml) was used for the binding to the conjugate 6OsuLacNAc. The starting concentration of Nemod-TF2 was <0.1 µg/ml (binding to conjugate number 37, Table 6). A linear relation of OD and concentration indicates an unspecific adsorption meaning there was no specific binding to this carbohydrate.

(ii) comparison of antibody binding against 6OsuLacNAc (Table 6, number 77) and the non-carbohydrate conjugate (Table 6, number 0) at four concentrations (dilution steps 1:2). Concentration dependent binding was investigated in a smaller concentration range against the conjugate 6OsuLacNAc (Table 6, number 77) as well as against the non-carbohydrate conjugate (Table 6, number 0). Measurement was not performed with control antibody Nemod-TF2, because the antibody does not bind to the non-carbohydrate conjugate. A comparison of the binding to the carbohydrate- and non-carbohydrate conjugate, may indicate to some extent a specific carbohydrate recognition.

(iii) binding to 6OsuLacNAc (Table 6, number 77) and the non-carbohydrate conjugate (Table 6, number 0) with or without periodate incubation. Mild periodate oxidation at acid pH cleaves carbohydrate vicinal hydroxyl groups (Woodward et al., J. Immunol. Meth 78:143 (1985), and is therefore a tool to check the specificity of a carbohydrate mediated antibody binding. Preincubation of the carbohydrate antigen with periodate would decrease the signal intensity of antibody binding. Binding of the LM-1 antibody was not sensitive to periodate, as compared to the Nemod-TF2 control antibody, in which a decreased signal was measured. Moreover, an increased binding was not only measured to the carbohydrate coated wells but to the non-carbohydrate coated wells too, which supports the interpretation of high background binding, possibly mediated by contamination(s) within the samples.

The data indicates absence of specific binding to any of the sugars. Thus, it seems unlikely that the carbohydrates tested reflect the target, and that a protein part may be part of the epitope.

For analysis of blood group antigens, LM-1 antibody was screened for binding to A1, A2, B and O blood groups using a standard hemagglutination assay. Hemagglutination involves red blood cells (RBCs) and can be used to identify RBC surface antigens (with known antibodies) or to screen for antibodies (with RBCs with known surface antigens). The results indicate that LM-1 did not detectably bind to any of the A1, A2, B and O blood group antigens.

For analysis of LM-1 antibody binding to lymphocytes and granulocytes. In brief, venous blood was collected from a volunteer and a Ficoll gradient was prepared to separate the blood components. Ficoll is part of Ficoll-Paque which is used in to separate blood into its components (e.g., erythrocytes, leukocytes etc.). Ficoll-Paque is placed at the bottom of a column, and blood is then slowly layered above Ficoll-Paque. After centrifugation, the following layers will be visible in the column, from top to bottom: plasma and other constituents, mono-nuclear cells (PBMC/MNC, e.g. lymphocytes), Ficoll-Paque, and erythrocytes & granulocytes which should be present in pellet form. After separation with Ficoll gradient, the different cell populations (lymphocytes, granulocytes) were washed and used for FACS analysis. Cells ($2 \times 10^5$) were subsequently incubated on ice with LM-1 antibody in a final concentration of 100 µg/ml or human isotype-matched control antibody (Chrompure human IgM, Dianova, Hamburg, Germany) in the same concentration for 15 minutes on ice, washed with PBS containing 0.01% sodium azide, and then incubated with a FITC-labeled rabbit anti-human IgM antibody (1:50, Dianova) for 15 minutes on ice. Antibodies were optimally diluted in PBS containing 0.01% sodium azide and cells were analyzed by flow cytometry (FACScan; Becton Dickinson, USA). The results indicate that LM-1 did not detectably bind to lymphocytes or granulocytes.

Example 13

This example includes a description of studies showing LM-1 antibody fragment retains cell proliferation inhibiting activity.

LM-1 antibody, as represented by an antibody produced by a hybridoma deposited as DSMZ Depsoit No. DSM ACC2623, deposited on Nov. 6, 2003, or as represented by an antibody having heavy and light chain variable region sequences set forth as SEQ ID NOs:1, 3, 5, or 7 and 11 was subjected to a buffer exchange with 100 mM sodium citrate (pH 3.5) using NAP™-10 columns (Amersham Pharmacia Biotech) prior to pepsin digestion. For each milligram of antibody, 5 µg pepsin (Sigma Aldrich, Taufkirchen, Germany) was added, followed by incubation for 10-15 min in a 37° C. water bath. The reaction was terminated by adding 1/10 volume of 3.0 M Tris (pH 8.8) followed by centrifuging at 10,000 g for 30 min. Pepsin digestion was also done with an unrelated control Human IgM antibody (Chrompure IgM, Dianova, Hamburg, Germany). Prior to apoptosis studies $F_v$ fragment and human control IgM fragment were dialyzed against PBS. SDS gel electrophoresis and Western blotting confirmed pepsin cleavage of both antibodies. The MTT cell proliferation assay described in Example 4 was used to study the effect on proliferation of BXPC-3 and MKN-45 cells.

The data indicate that LM-1 $F_v$ fragment inhibits cell proliferation of BXPC-3 and MKN-45 cells. The foregoing results indicate that LM-1 antibody fragments retain the ability to inhibit or reduce cell proliferation.

Example 14

This example includes a description of in vivo studies of LM-1 antibody. The data indicate that LM-1 antibody is effective and can reduce size of various tumors, including colon carcinoma, lung cancer, pancreatic cancer, a tumor resistant to chemotherapy, as well as tumor metastasis.

HT-29 human colon carcinoma cells are considered a model for metastasis in humans. This colon carcinoma metastasizes to liver in mice.

In brief, HT-29 cells ($1 \times 10^6$) were injected intraportally into three groups of athymic mice (10 week old Balb/c nu/nu mice, Charles River GmbH, Sulzfeld, Germany). On Days 7, 9, 11, 13 and 15 after inoculation, mice were administered 260 µg PAT-LM1 (~10.4 mg/kg, Group 1) and 260 µg non-specific IgM (Group 2) qod. Additional control animals (Group 3) did not receive any treatment (no injection). The number of animals with either macroscopic or microscopic tumor lesions on the liver at Day 60 were determined for each group.

Figure 6:
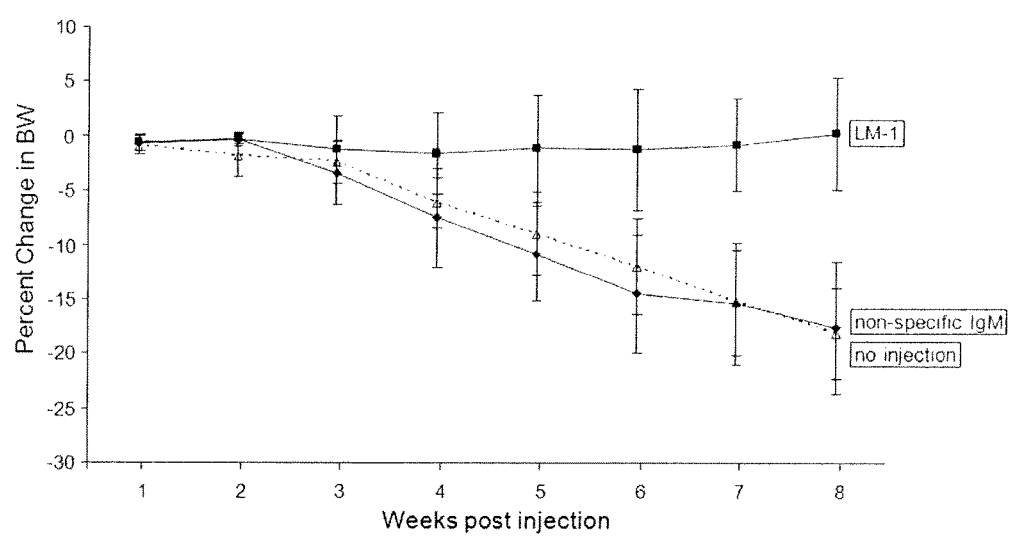
FIG. 6 shows body weight of LM-1 injected mice, which was maintained for 8 weeks post injection. Body weight in the no injection control and non-specific IgM injected control was reduced by almost 20%, due to poor health from liver metastasis.

Body weight of the LM-1 injected mice was maintained for 8 weeks post injection of HT-29 cells. In contrast, body weight in the no injection control mice and non-specific IgM injected control mice declined by almost 20% during the 60 day observation period, due to poor health from liver metastasis (FIG. 6).

Figure 7:
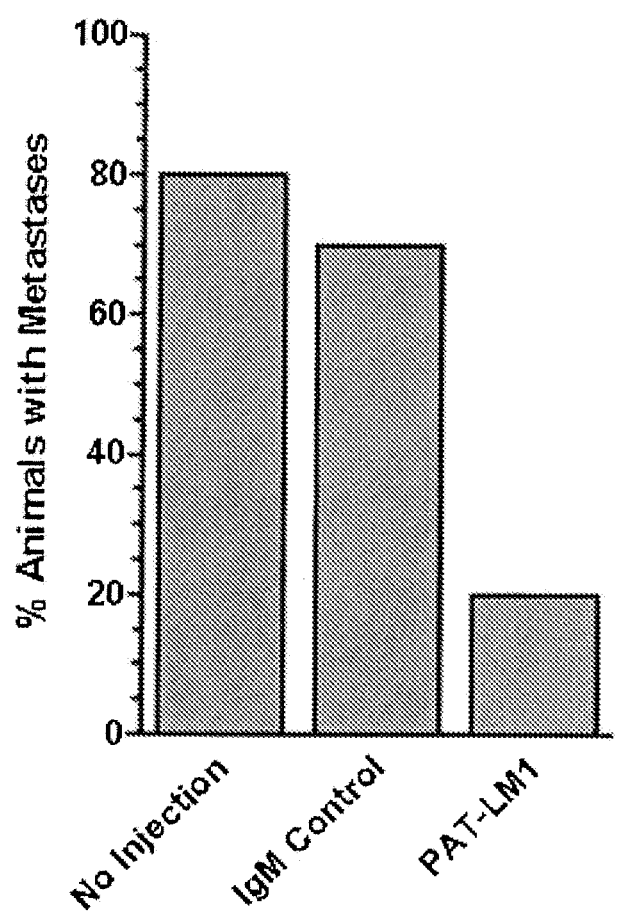
FIG. 7 shows data indicating that LM-1 antibody can reduce tumor metastasis establishment, formation, or proliferation (growth).

Multiple macroscopic and microscopic lesions on the liver occurred in about 80% of the no injection control mice, and in about 70% of the non-specific IgM control mice. In contrast, only about 20% of the LM-1 injected mice had either macroscopic or microscopic tumor lesions on the liver (FIG. 7). The foregoing results therefore indicate that LM-1 antibody can reduce tumor metastasis establishment, formation, or proliferation (growth) of metastatic cells.

The foregoing results indicate that LM-1 antibody reduces the number of metastasis in liver. LM-1 antibody treatment conserves the initial body weight of the animals after tumor cell injection, which may indicate systemic anti-tumor activity of LM-1.

A-549 is a human cell line that forms lung carcinoma in animals, and therefore can be used as an animal model of human lung carcinoma (e.g., non-small cell lung carcinoma, NSCLC). A-549 lung carcinoma cells ($2.0 \times 10^6$) were injected s.c. at day 0 into mice (C.B-17/IcrHanHsd-scid, age 6-8 weeks, n=10 per group). LM-1 antibody (200m) or control mAb (Chrompure human IgM), or vehicle control (NaCl) was administered i.p. at days 1, 3, 5, 7 and 9 to mice. Mice were sacrificed at day 17 and tumor weights and volumes were determined.

Average tumor size in mice injected with LM-1 antibody was significantly less than in mice injected with control mAb. The reduction in tumor size in mice injected with LM-1 antibody was 71%, compared to mice injected with control mAb.

Histological analysis revealed that in LM-1 treated mice, tumor lesions exhibited evidence of tumor cell apoptosis and tumor growth inhibition and regression. In LM-1 treated mice, tumor lesions also exhibited evidence of necrosis.

BXPC-3 is a human cell line that forms pancreatic cancer (carcinoma) in animals, and therefore can be used as an animal model of human pancreatic cancer. BXPC-3 cells ($2.0 \times 10^6$) were administered s.c. at day 0 to mice (C.B-17/IcrHanHsd-scid, age 6-8 weeks, n=10 per group). LM-1 antibody (200 µg) or control mAb (Chrompure human IgM) was administered i.p. every second day after the tumor became established (palpable) at day 8 (5 doses) and in week 4 (4 doses). Mice were sacrificed at day 24 and tumor volumes determined.

Size of the established pancreatic tumor in mice injected with LM-1 antibody was significantly less than in mice injected with control mAb. The reduction in tumor size in mice injected with LM-1 antibody was 44%, compared to mice injected with control mAb.

To determine LM-1 activity in an established tumor model, established A-549 cell lung carcinoma in mice was subjected to treatment with LM-1 antibody. A-549 lung carcinoma cells ($2.0 \times 10^6$) were administered s.c. at day 0 to mice (NMRI nude mice, age 6-8 weeks, n=10 per group). LM-1 antibody (1 mg/kg, 3 mg/kg, 9 mg/kg, or 27 mg/kg) or control saline or IgM mAb (Chrompure human IgM, 675 µg) was administered i.p. qod six times to mice with established tumors (14 days after lung carcinoma cell administration) every second day after tumor became established (palpable, $\approx 7$ mm$^2$). At day 14, average tumor volume was about 200 mm$^3$. Mice were sacrificed at day 27 and tumor volume determined.

Reduction of established tumor volume was dose dependent with the greatest reduction in tumor volume observed at a dose of 27 mg/kg. Tumor volume appeared to stabilize at doses of 1 and 3 mg/kg. At the 9 mg/kg dose, there was no apparent reduction of tumor volume.

The foregoing results indicate that LM-1 antibody can reduce the size of various tumor types, including colon carcinoma, lung cancer, pancreatic cancer, a tumor resistant to chemotherapy, as well as tumor cell metastasis establishment, formation, and proliferation (growth). The foregoing results also indicate that LM-1 antibody can reduce the number, size of tumors or metastasis, or stabilize the number or size of various established tumors.

Example 15

This example includes a description of LM-1 target identification and verification. The data indicate that LM-1 antibody can apparently bind to non-pou domain-containing octamer-binding protein (NONO), also known as 54 kDa nuclear RNA- and DNA-binding protein (p54nrb) and 55 kDa nuclear protein (nmt55).

Figure 8:
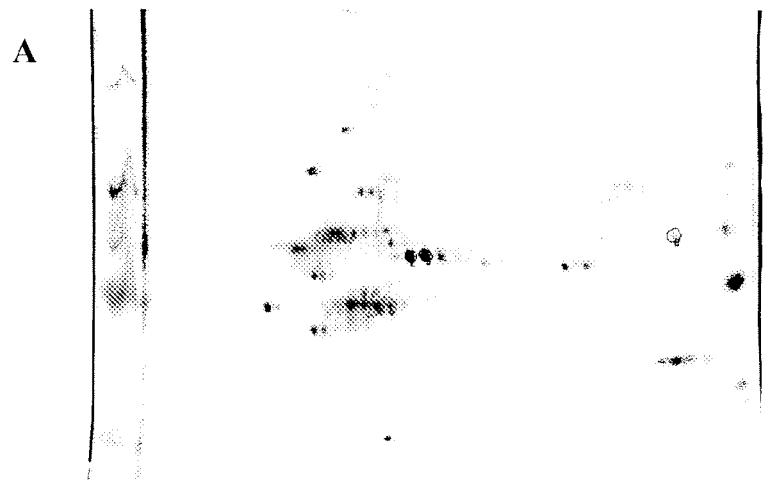
FIG. 8A-8B show BxPC3 cell membrane preparation analysis by 2D polyacrylamide gel electrophoresis (PAGE). A) Fractionated proteins transferred to PVDF membrane and stained with LM-1 antibody; and B) Spots on the PVDF membrane that bound to LM-1, which were superimposed on a silverstained PAGE, and the corresponding spots excised from the gel and subjected to MALDI-TOF analysis.
Figure 8:
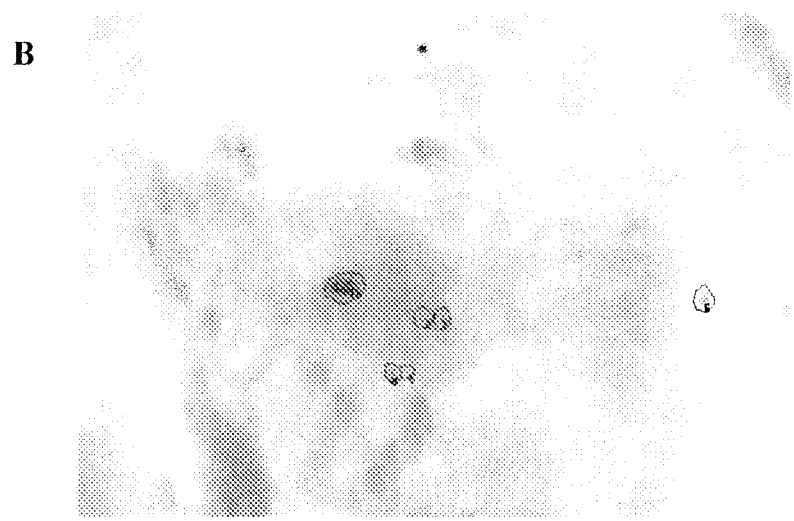

In brief, a membrane preparation of BxPC3 cells was analyzed by 2D polyacrylamide gel electrophoresis (PAGE) (Proteome Factory, Berlin, DE). Fractionated proteins (FIG. 8A) were transferred to a PVDF membrane and subsequently stained with LM-1 antibody. The indicated spots on the PVDF membrane (that bound to LM-1; FIG. 8B) were suerimposed on a silverstained PAGE, and the 8 corresponding spots were excised from the gel and subjected to MALDI-TOF analysis (Proteome Factory, Berlin, DE).

The results of the MALDI-TOF, which lists the proteins from each spot in order of probability, after comparison of identified fragments with the sequence database, were Spot 1a, Vimentin, Desmin, tubulin, alpha, keratin, and Neurofilament; Spot 1b, Vimentin, Desmin, peripherin, keratin, and Neurofilament; Spot 1c, Vimentin, Desmin, peripherin, keratin, neurofilament, and alpha-internexin; Spot 2, cytokeratin 8; Spot 3, Not identified, Gastric inhibitory polypeptide, Glucose-dependent insulinotropic peptide, phospholipase C-alpha, and protein disulfide isomerase; Spot 4, cytokeratin 18, and ATP-binding cassette protein; Spot 5, beta actin; Spot 6, 54 kDa protein, non-POU domain containing (NONO), and human splicing factor; Spot 7, Not identified, fucosyltransferase, Tumor necrosis factor receptor superfamily member 5, cystic fibrosis transmembrane conductance regulator, HECT domain containing 1, and Alu subfamily SB1; Spot 7, Not identified, fucosyltransferase, Tumor necrosis factor receptor superfamily member 5, cystic fibrosis transmembrane conductance regulator, HECT domain containing 1, and Alu subfamily SB1; Spot 8, Not identified, serine/arginine repetitive matrix 2, ras guanyl releasing protein, unnamed protein product, and mKIAA0232 protein.

Band 1: The protein was identified as calnexin [67.9 kDa/pI 4.6/gi|179832/*Homo sapiens*].

Band 2: Glutamate dehydrogenase 1 [56.3 kDa/pI 6.7/gi|4885281/*Homo sapiens*] was identified in band 2.

Band 3: The protein was identified as calnexin [67.9 kDa/pI 4.6/gi|179832/*Homo sapiens*].

Band 4: The protein of band 4 was identified as non-POU domain containing, octamer-binding, [54.3 kDa/pI 9.1/gi|34932414/*Homo sapiens*].

Band 5: Identification of this band is not really clear, perhaps due to low protein concentration in the gel band. But there is evidence that the protein band consists of non-POU domain containing, octamer-binding, [54.3 kDa/pI 9.1/gi|34932414/*Homo sapiens*].

Band 6: A mix of keratin 9 [62.3 kDa/pI 5.1/gi|55956899/*Homo sapiens*] and chaperonin [61.2 kDa/pI 5.7/gi|31542947/*Homo sapiens*] could be found in the protein band. Keratin 9 might be a contamination.

The amino acid sequence of wild type NONO (SEQ ID NO:16) with Sequences identified in LM-1 target that are identical to wild type are marked in bold (first identification).

```
  1 mqsnktfnle kqnhtprkhh qhhhqqqhhq qqqqqppppp ipangqqass qnegltidlk 61 nfrkpgektf tqrsrlfvgn lppditeeem rklfekygka gevfihkdkg fgfirletrt 121 laeiakveld nmplrgkqlr vrfachsasl tvrnlpqyvs nelleeafsv fgqveravvi 181 vddrgrpsgk givefsgkpa arkaldrcse gsfllttfpr pvtvepmdql ddeeglpekl 241 viknqqfjke reqpprfaqp gsfeyeyamr wkaliemekq qqdqvdrnik eareklemem 301 eaarhehqvm lmrqdlmrrq eelrrmeelh nqevqkrkql elrqeeerrr reeemrrqqe 361 emmrrqqegf kgtfpdareq eirmgqmamg gamginnrga mppapvpagt pappgpatmm 421 pdgtlgltpp tterfgqaat megigaiggt ppafnraapg aefapnkrrr y
```

Figure 9:
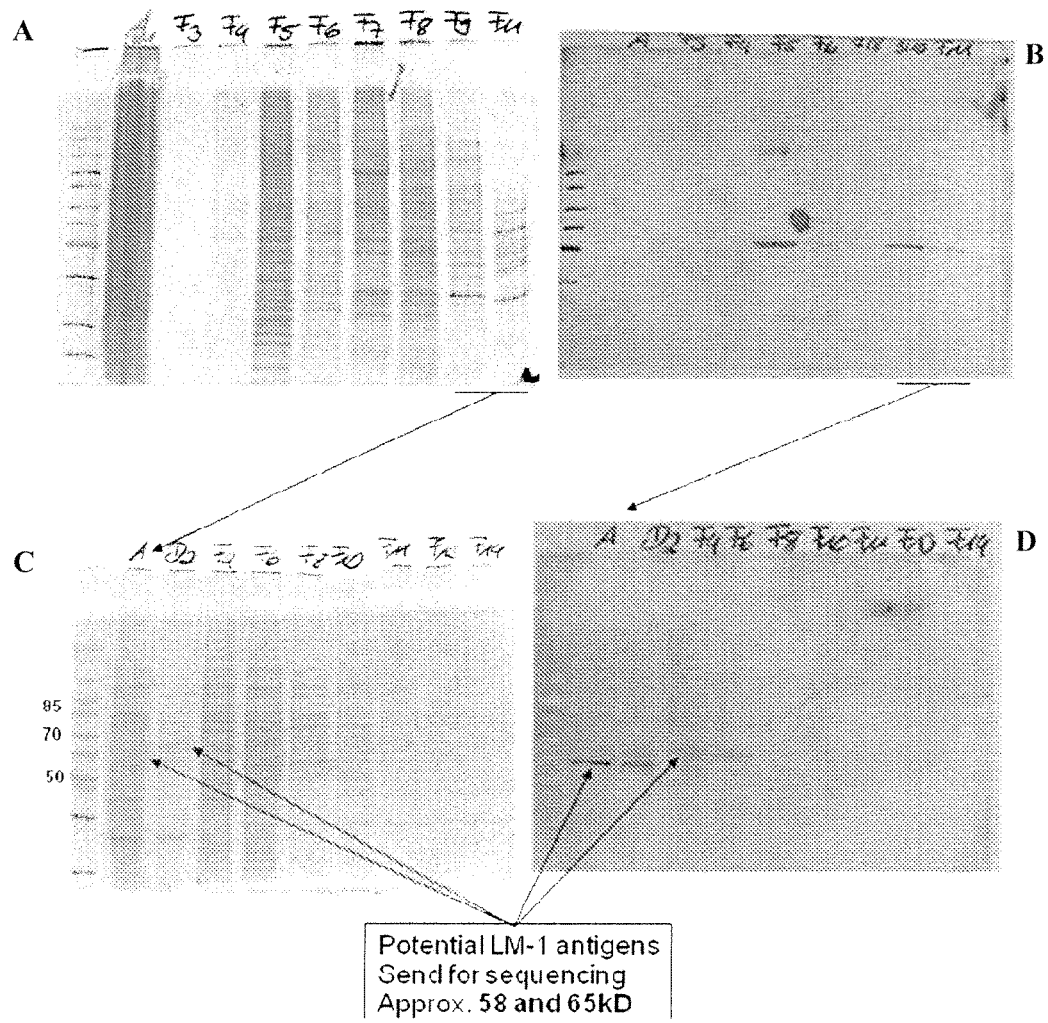
FIGS. 9A-9D show identification of LM-1 Target. A) Gel-chromatography of BXPC-3 extracts; B)-D) fractions 9 and 10 selected and subjected to anion-exchange chromatography and subsequent blotting with LM-1 antibody.

LM-1 target was also identified by Gel-chromatography of BXPC-3 extracts (FIG. 9A) and fractions 9 and 10 selected and subjected to anion-exchange chromatography and subsequent blotting with LM-1 antibody (FIGS.

The amino acid sequence of wild type NONO (SEQ ID NO: 16)with Sequences identified in LM-1 target that are identical to wild type are marked in bold (second identification).

```
  1 mqsnktfnle kqnhtprkhh qhhhqqqhhq qqqqqppppp ipangqqass qnegltidlk 61 nfrkpgektf tqrsrlfvgn lppditeeem rklfekygka gevfihkdkg fgfirletrt 121 laeiakveld nmplrgkqlr vrfachsasl tvrnlpqyvs nelleeafsv fgqveravvi 181 vddrgrpsgk givefsgkpa arkaldrcse gsfllttfpr pvtvepmdql ddeeglpekl 241 vikmqqfhke reqpprfaqp gsfeyeyamr wkaliemekq qqdqvdrnik eareklemem 301 eaarhehqvm lmrqdlmrrq eelrrmeelh nqevqkrkql elrqeeerrr reeemrrqqe 361 emmrrqqegf kgtfpdareq eirmgqmamg gamginnrga mppapvpagt pappgpatmm 421 pdgtlgltpp tterfgqaat megigaiggt ppafnraapg aefapnkrrr y
```

9B-9D). Appropriately sized stained LM-1 target proteins from the corresponding gel (58 and 65 kDa) were excised and sequenced.

In brief, protein bands were reduces and alkylated, and then digested with the protease trypsin. The resulting peptides were measured with MALDI MS in a range of 800 Da-4500 Da for obtaining a peptide mass fingerprint. A database search with the program ProFound was done against the NCBI database.

The foregoing data indicate that LM-1 binds to a new cancer target, namely a membrane bound isoform of NON-POU DOMAIN-CONTAINING OCTAMER-BINDING PROTEIN (NONO), also known as 54 kDa nuclear RNA- and DNA-binding protein (p54nrb) and 55 kDa nuclear protein (nmt55). This protein is expressed on cancer, tumor and malignant cells, and LM-1 binding induces apoptosis of the cells to which it binds.

The nmt55 gene has been reported to be mapped to chromosome Xq13.1 (70,420,158-70,437,743). Analysis of expression of 33 X-linked genes in 8 mouse/human somatic cell hybrids that contained either the human active (3 hybrids) or inactive (5 hybrids) X chromosome was reported to reveal that the nmt55 gene was expressed only in those hybrids with the active human X. The gene spans about 18 kb and consists of 12 exons ranging in size from 40 to 1,227 bp, the start codon has been reported to be in exon 3 and the stop codon in exon 12.

In order to verify the identity of LM-1 Target, siRNA transfection was performed to downregulate expression of NONO/nmt55. Binding of LM1 should disappear if NONO/nmt55 is the target.

In brief, BxPc-3 cells were transiently transfected with specific siRNA (dharmacon siGENOME Smart Pool) and were harvested 48 h after transfection. Cells were lysed and samples run on a 10% PAGE and blotted on PVDF-Membrane. The membrane blot was stained either with α-nmt55 or LM-1 IgM.

The siRNA downregulated NONO/nmt55 expression (FIG. 10A). Binding of LM-1 in siRNA transfected cells was reduced (FIG. 10B, arrow). These studies corroborate that LM-1 binds to NONO/nmt55.

Figure 11:
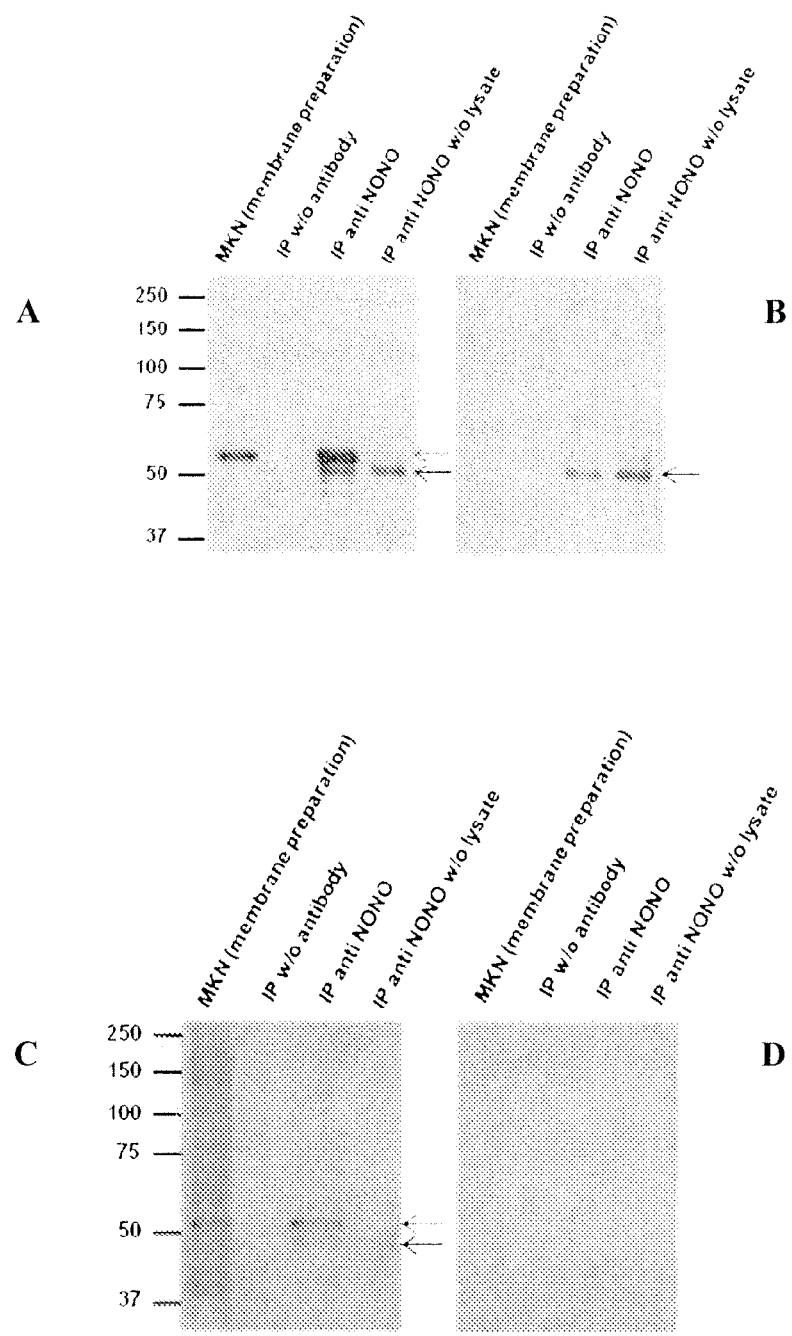
Figure 12:
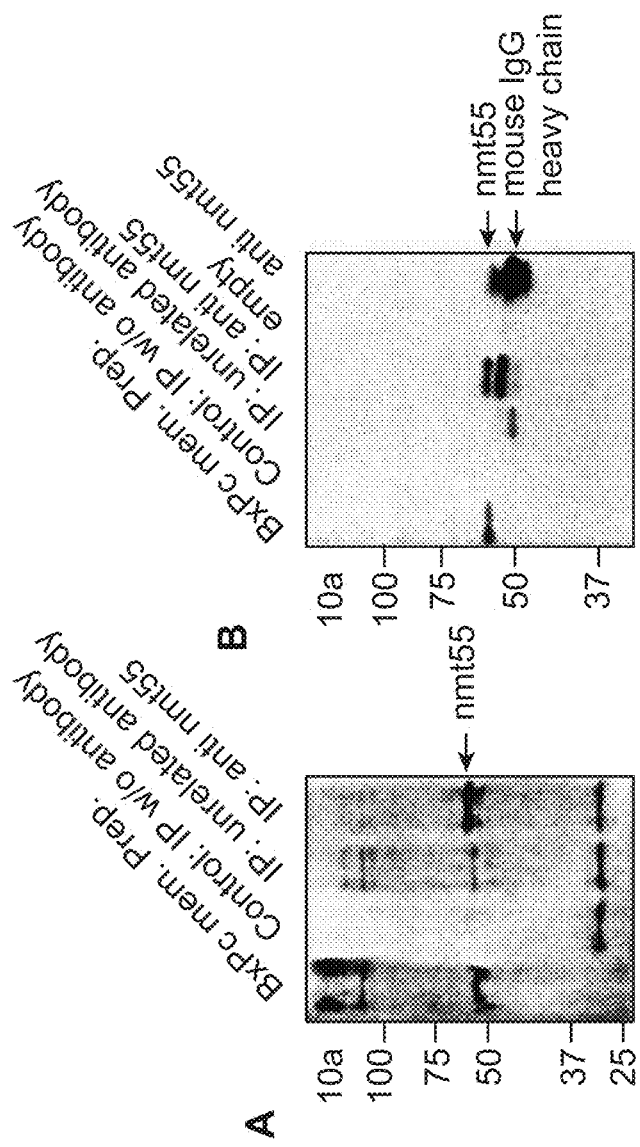
Figure 13:
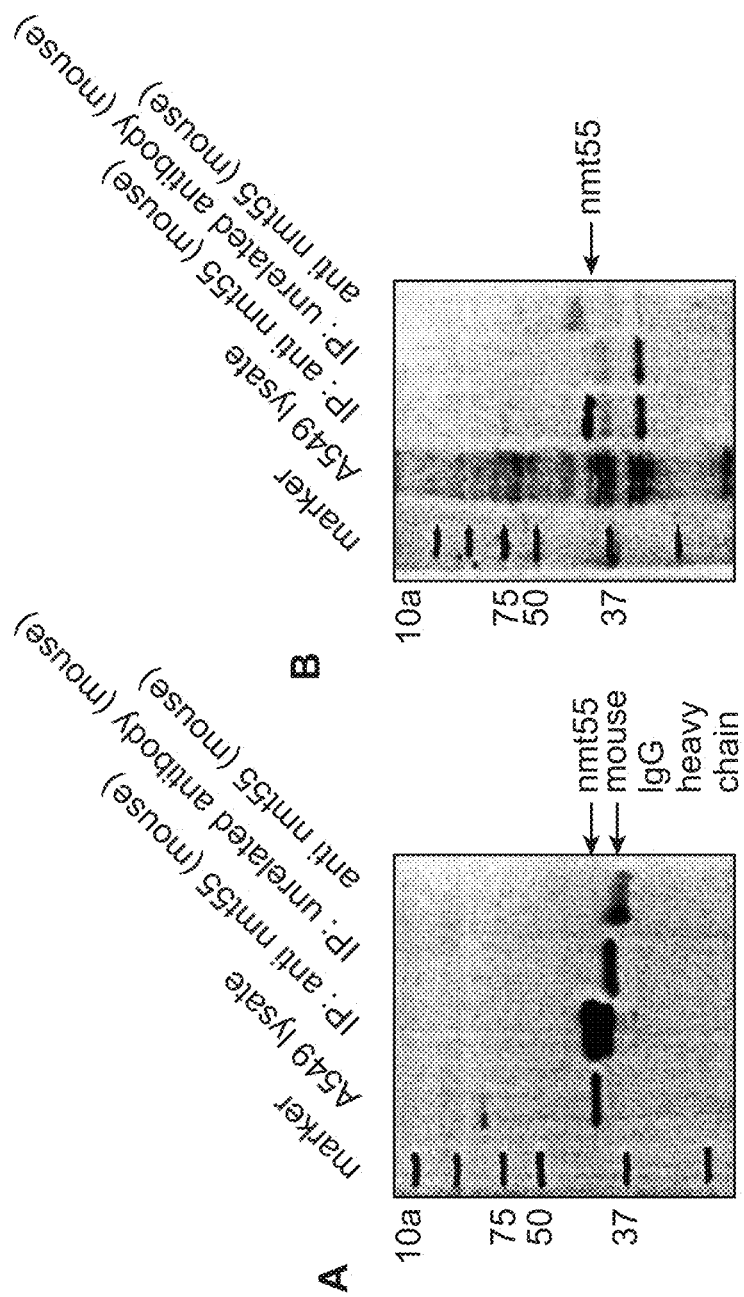

To further verify the identity of LM-1 Target, immunoprecipitation studies of MKN, BxPC-3 and A549 cell membrane preparations were performed with a commercial antibody that binds to NONO/nmt55 (Dianova, MA3-2024). The results are illustrated in FIGS. 11-13.

FIGS. 11A-11D illustrate the results with MKN cells. In brief, cell membrane extracts were immunoprecipitated with anti nmt55, and subsequently stained with anti NONO/nmt55 Mouse mAb/anti mouse IgG HRP (FIG. 11A), anti mouse IgG HRP (FIG. 11B), LM-1/anti human IgM HRP (FIG. 11C), anti human IgM HRP (FIG. 11D). The top (higher molecular weight) arrow is NONO, and the bottom (lower molecular weight) arrow is mouse heavy chain.

FIGS. 12A-12B illustrate the results with BxPC-3 cells. In brief, cell membrane extracts were immunoprecipitated with anti nmt55, and subsequently stained with LM-1 (FIG. 12A), or stained with anti NONO/nmt55 (FIG. 12B), Arrows indicate nmt55 and mouse IgG heavy chain. The results indicate that anti nmt55 antibody can precipitate the protein from the BxPC-3 cell membrane extract.

FIGS. 13A-13B illustrate the results with A549 cells. In brief, cell membrane extracts were immunoprecipitated with anti nmt55, and subsequently stained with anti NONO/nmt55 (FIG. 13A), or stained with LM-1 (FIG. 13B), Arrows indicate nmt55 and mouse IgG heavy chain. The results indicate that anti nmt55 antibody can precipitate the protein from the A549 cell membrane extract.

To further verify the identity of LM-1 Target, FACS analysis of A549, BxPC-3 and MKN cells with antibody that binds to NONO/nmt55 (Dianova, MA3-2024) or LM-1 were performed. These studies revealed that NONO/nmt55 is expressed on the cell surface of A549, BxPC-3 and MKN cells.

A549 cells were stably transfected with NONO antisense, and analyzed by FACS analysis with antibody that binds to NONO/nmt55 and LM-1. To produce vectors, human Nono cDNA (1422 bp) was amplified by polymerase chain reaction (PCR) using the human pancreatic cancer cell line BxPC. After PCR amplification, Nono full length transcript was inserted into pcDNA3.1-V5-His by TA cloning reaction (Invitrogen). This method is an undirected cloning strategy and therefore the ratio between Nono-sense (pcDNA3.1-V5-His-Nono-6×His) and -antisense (pcDNA3.1-V5-His-Nono-6×His-Anti) plasmids are around 50:50. After screening by PCR, several clones with Nono in sense (NONO-sense) and antisense (NONO-anti) direction under the control of the cytomegalovirus promoter (CMV) were identified.

A549 cells were transfected with NONO-anti using Trans-Pass transfection reagent and cells selected in 1 mg/ml G418 for 2-3 weeks. Seven stable cell lines with this antisense were established. Western blot analysis of endogenous Nono protein expression in these cells revealed significant reduction of protein levels compared to levels in control cells.

FACS studies of A549 cells transfected with NONO-anti revealed weaker binding of both NONO/nmt55 and LM-1 to the cells. The studies indicate that downregulation of NONO/nmt55 expression on the cell surface of A549 cells reduced binding of anti NONO/nmt55 and LM-1 to the cells.

NONO-sense was transfected into HEK293 using Trans-Pass transfection reagent and cells selected in 1 mg/ml G418 for 2-3 weeks. Ten stable cell clones were established that overexpressed NONO. Western blot analysis of these cells showed a stable overexpression of recombinant Nono-6×His fusion protein. These stable cell lines can be used for FACS studies or, after Nono-6×His protein purification, generation of specific target ELISA's.

To confirm that LM-1 binds to HEK293 cell transfected with NONO, 40 µg of HEK293-Nono-6×His-A9 and HEK293$^{wt}$ cell lysate was used for a western blot. After blotting immunoreactive proteins were detected using LM-1 (IgM) and a horseradish peroxidase-conjugated secondary antibody (anti-human-IgM-HRP) (FIG. 14A). To show that the LM-1-Nono interaction are target specific, the same protein probes were analyzed with a control IgM (FIG. 14B). The analysis revealed a specific interaction of LM-1 and Nono-6×His fusion protein. Different size of fusion and endogenous protein is an artifact of the recombinant protein expression in pcDNA3.1-V5-His.

Example 16

This example includes a description of studies to determine whether glycosylation of NONO protein is required for LM-1 binding.

To determine if NONO glycosylation is required for LM-1 binding, human NONO gene (pEXP5-CT) was transformed into BL21 (DE3) bacteria. After transformation, several positive bacteria clones were expressed in LB-medium induced by 1 mM IPTG. Western blot analysis demonstrated that LM-1 (IgM) bind to the bacteria expressed Nono-6×His fusion protein (FIG. 15). The fact that bacteria don't glycosylate proteins excludes the thesis that the LM-1 antibody-antigen (target) interaction requires antigen (target) glycosylation.

Example 17

This example includes a description of various LM-1 antibody variants, and binding studies. The binding studies indicate that the LM-1 antibody sequence variants retain binding capability to target antigen nmt55.

Various LM-1 antibodies were expressed as a recombinant scFv (single-chain) antibody and analyzed for binding to the target cells (A549, BxPC-3, HT-29, Hela, CRL1424 and HDFa cells). Single amino acid changes in the protein sequence of the heavy and/or light chain V (variable) domains can affect cell expression level, and possibly the affinity of the antibody to the target antigen. Nevertheless, all variants detectably bind to cells expressing target as well as bacterially expressed NONO/nmt55 as determined by an ELISA assay.

The different LM-1 scFv antibodies studies for binding are LM-1 scFv (new)-represented by SEQ ID NOs:3 and 11, 1BTA1.16VH and 1BTA1.16VL), LM-1 scFv (as represented by SEQ ID NOs:1 and 11), LM-1 scFv opt (as represented by SEQ ID NOs:9 and 13), a hybridoma derived LM-1 IgM, and LM-1 IgM (SEQ ID NOs:3 and 11) produced in a perC.6™ cell line (Percivia).

Binding analysis was performed with living cell populations of human cancer cell lines (A549, BxPC-3, HT-29, Hela, CRL1424 and HDFa cells) grown to a consistent cell density. Human antibodies were added to the cells and if they display a target antigen recognised by the antibodies then binding will occur. A secondary antibody with a fluorescent tag (FITC) is added which is then detected by FACS (Fluorescent Activated CellSorting). We use mouse anti-FLAG FITC for the LM-1 scFv proteins and mouse anti-human IgM FITC for the IgM protein.

Binding is reflected by a population shift to the right, which is considered positive, providing that this shift is greater than the negative controls. Several events can cause a "false positive" shift. Cells alone auto fluoresce, so they need to be measured, as some cell lines do this more than others. The addition of just the primary antibody causes the cells a shift as does the addition of just the secondary antibody. All of these events are considered as negative controls. Binding of the antibody to a cell line (HDFa-dermal cell line) negative for the target antigen is also performed.

A549, BxPC-3, HT-29, Hela, CRL1424 and HDFa cell lines were compared for LM-1 binding. A concentration of 10,000 cells was used for each cell line. Antibody was added at 100 ug/ml but the total amount of protein used per reaction is 20 ug. The data indicate that all forms of the LM-1 antibody studied bind to the 5 cell lines that express the target antigen.

Next, LM-1 target antigen, nmt55, was expressed in bacteria and purified using an anti-HIS resin. The Coomassie stained SDS-gel showed several bands in the 50-60 Kda region, which is the expected size. The 55 Kda band was the strongest, but not the only band. These other bands will contribute to the overall protein concentration. ELISA assays were performed. Briefly, nmt55 is coated onto the plate, blocked, then probed with the antibodies then the relevant secondary antibody-HRP is added and detected. The data indicate that all forms of the LM-1 antibody studied bind to bacterially expressed nmt55 target antigen.

Example 18

This example includes a description of generation of isotype switched LM1 IgG antibody and binding studies.

In brief, the VH region of LM1 was amplified by polymerase chain reaction (PCR) using the human LM1 IgM hybridoma. cDNA as a template using the following primer set: 5'primer-AGA TCT GCC ACC ATG GCA TGC CCT GGC TTC-3' (SEQ ID NO: 17), and 3'-primer, 5'-TGA AGA GAC GGT GAC CAT TGT CCC (SEQ ID NO: 18). The CH region of LM1 was amplified by polymerase chain reaction (PCR) using the expression vector pFUSE-CHIg-hG1 as template. Following primer set was used: 5'primer-AGC ACC AAG GGC CCA TCG GTC TTC-3' (SEQ ID NO: 19), and 3'-primer, 5'"-CTC GAG TCA TTT ACC CGG AGA CAG GGA GAG (SEQ ID NO: 20).

To produce LM1 heavy chain, the VH- and CH-region was ligated by T4 DNA ligase (New England Biolabs) and amplified by polymerase chain reaction (PCR). Following primer set was used: 5'primer-AGA TCT GCC ACC ATG GCA TGC CCT GGC TIC-3'(SEQ ID NO: 17), and 3'-primer, 5'-CTC GAG TCA TIT ACC CGG AGA CAG GGA GAG(SEQ ID NO: 20). This fragment was ligated by TA cloning into pEXP5-CT/TOPO TA vector (Invitrogen). After TA cloning, LM1 heavy chain was cut out of pEXP5-CT/TOPO TA vector by BglII/XhoI and transferred into first expression cassette of pVitro2-neo-mcs (InvivoGen).

The light chain of LM1 was amplified by polymerase chain reaction (PCR) using the human LM1 IgM hybridoma. cDNA as a template using the following primer set: 5'primer-GAT ATC TCC GCC ACC ATG GCA TGC CCT GGC TTC-3' (SEQ ID NO: 21), and 3'-primer, 5'-GTC GAC CTA TGA ACA TIC TGT AGG GGC CAC (SEQ ID NO: 22). This PCR fragment was ligated by TA cloning into pEXP5-CT/TOPO TA vector (Invitrogen). After TA cloning, LM1 light chain was cut out of pEXP5-CT/TOPO TA vector by EcoRV/Sal I and transferred into second expression cassette of pVitro2-neo-mcs (InvivoGen). The sequence of all PCR products was confirmed by DNA sequencing (Qiagen).

To confirm that the IgG form retains binding activity, antibody was produced by expression in HEK293 cells, and antibody binding to A549 and BxPc-3 cells was evaluated. The materials used for these studies included RPMI 1640 (PAA, E15-039), 10% Fetal bovine serum (PAA, A15-151), 1% Glutamin (PAA, M11-004), Cell dissociation solution (Sigma C5789), Anti-human IgG-FITC, dianova, 109-095-003, and 1×PBS.

The expression plasmid "pVitro2-LM1-HC-LC" with a stock concentration of 2.5 µg/µl and a A260/A280 ratio between 1.75 and 1.78 was utilized. The transfection procedure was performed in serum-containing medium (DMEM 1% FBS) on a surface of around 2500 $cm^2$ (16×154 $cm^2$ poly-D lysine coated well plates). In brief, HEK293 cells cultured under serum-containing conditions and collected in the middle of the exponential growth phase, were counted 24 h before to perform the transfection procedure. They were diluted to a concentration of about $2.5 \times 10^7$ cells/plate and incubated until next day. Cells were counted again and when they nearly doubled their concentration (between $5.0 \times 10^7$ cells/plate (cell density around 80%), they were transfected as described below.

For the preparation of the transfection complex, 1.5 mg endofree DNA was diluted in 40 ml fresh serum-free medium (sufficient for sixteen 150 $cm^2$ plate). After pipetting up and down to mix the solution, 10 ml PEI was added, immediately vortex-homogenized and incubated for 8 min at RT. After addition of 324 ml of serum-containing Medium (10%), the DNA:PEI complex was added to the cells and incubated at 37° C. for one hour. To remove the PEI from cells, plates are washed three times with PBS. Then, plates are filled with 70 ml serum-containing Medium (1% FBS) and incubated overnight. To remove dead cells, medium was changed and then all plates were incubated normally for 6 days at 37° C. The supernatants were stored at 4° C. for later protein purifications.

For binding studies, A549 and BxPc-3 cells cells were trypsinized with cell dissociation solution, resuspended in complete medium and set on 2×10⁵/ml. After 30 minutes on ice, cells were dispersed at 1 ml per FACS-tube and washed once with ice-cold PBS by centrifugation with 500 g and 4° C. Staining was done with indicated concentrations of IgG antibody or without antibody in 200 μl PBS. Antibodies were incubated 30 minutes on ice, then washed with ice cold PBS and secondary antibody was applied at a dilution of 1:50 in 200 μl per tube. After another 30 minutes of incubation in the dark, cells were washed twice with PBS and applied to FACS.

FACS analysis revealed that the LM1 IgG antibody binds to both A549 and BxPc-3 cells, indicating that the antibody retains antigen/epitope specificity.

Example 19

This example includes a description of additional binding studies indicating that LM-1 binds to target antigen, NONO/nmt55, at a portion that includes the N-terminal 300 amino acid sequence of NONO/nmt55.

In brief, nmt-55 was cloned into pPOW vector for secretion into *E. coli* periplasm. Primers were designed to amplify the NONO gene from the human NONO gene cloned in pEXP5-CT (described in Example 16) and introduced to the bacterial expression vector pPOW which allows secretion into the *E. coli* periplasm via the pelB secretion signal.

To express nmt-55 pPOW, a 50 ml starter culture was inoculated with freshly transformed *E. coli* BL21 (DE3) containing pPOW plasmid, encoding for full length nmt55, was grown in yeast tryptone (YT) ampicillin medium at 33° C. with shaking, approximately 250 rpm. Following overnight incubation, 25 ml of this culture was added to 175 ml of terrific broth (TB) containing ampicillin in a 2 liter Erlenmeyer flask. Culture was grown at 33° C. with shaking, approximately 250 rpm, until it reached an optical density (OD$_{600}$) of ~4.000 (~3 h), a 1 ml aliquot and stored at 4° C. for later comparison (T$_O$). Culture was then shifted to a 42° C. Incubators and continued to be grown for an additional 3 hours. Progress was checked periodically after 3 hours, once OD$_{600}$ had stabilized induction was stopped. A 1 ml aliquot was taken post-induction (T$_{FINAL}$) and stored at 4° C. for later comparison.

Cultures were transferred to 250 ml polycarbonate bottles (Nalgene) and centrifuged at 4000×g, 4° C. for 20 minutes to pellet *E. coli* cells. The media was them decanted and the pellets stored at −20° C. for protein extraction and purification using Profinia™ anti-His purification.

To extract nmt-55 pPOW, thawed pellets were thoroughly re-suspended, by pipetting and vortexing, in 15 ml of Profinia denaturing IMAC lysis buffer (Bio-Rad Laboratories) to lyse the cells. The lysate was then sonicated on ice, using a probe sonicator (10 μm amplitude), at 30 sec intervals for 4 minutes. The lysate was clarified by centrifugation (20,230×g; Eppendorf minifuge 542) in 2 ml microfuge tubes (Eppendorf) and filtered through 0.45 μm filter under vacuum. Lysate was then transferred a 50 ml sample tube (Falcon; BD) for purification.

Purification was performed via His-tag using Profinia™ denaturing immobilised metal affinity chromatography (IMAC). In brief, extracted nmt-55 was purified via Profinia™ automated IMAC protein purification. The buffers used for purification were supplied by Bio-Rad as 1.4× concentrates. Urea was added to these concentrates to obtain a final concentration of 6M urea. An IMAC (Ni-NTA) was installed into the system and the instrument set up as per manufacturer's recommendations. Profinia IMAC protocol:

| Step | Function | Buffer | ml/min | Column Volumes | Time (mins) |
|---|---|---|---|---|---|
| 1 | Water Wash | Di Water | 20 | — | 0.2 |
| 2 | Equilibrate column | Di Water | 2 | 2 | 1 |
| 3 | Equilibrate column | Buffer 1† | 2 | 5 | 2.5 |
| 4 | Load sample | N/A | 2 | X | X |
| 5 | Wash column 1 | Buffer 1† | 2 | 6 | 3 |
| 6 | Wash column 2 | Buffer 2† | 2 | 6 | 3 |
| 7 | Elute 1* | Buffer 3† | 2 | — | 3.1 |
| 8 | Elute 2 | Buffer 3† | 2 | 4 | 2 |
| 9 | Clean column | Buffer 5† | 2 | 5 | 2.5 |
| 10 | Clean column | Buffer 6† | 2 | 5 | 2.5 |
| 11 | Water wash | Di Water | 2 | 5 | 2.5 |
| 12 | Store column | Buffer 7† | 2 | 7 | 3.5 |
| 13 | Water wash | Di Water | 20 | — | 0.2 |
| 14 | Clean pump seals | Di Water | 20 | — | 0.2 |
| 15 | Clean pause | — | — | — | — |
| 16 | Clean sample port | Di Water | 20 | — | 0.2 |

†Buffer number as per Profinia position number

Buffer Exchange was performed via Amicon Ultra-15 devices. In brief, 15 ml of 1×PBS (300 mM NaCl, pH6.5) was added to an Amicon Ultra-15 centrifugal concentrator and spun at 4000 rpm (4° C.) for 15 minutes to remove any preservative on the membranes. Entire eluted sample volume (4 ml) was added to the membrane reservoir and made to 15 ml with 1×PBS (300 mM NaCl, pH6.5) and spun at 4000 rpm (4° C.) for 30 minutes. Once sample was at ~1.0 ml the flowthrough was discarded and an additional 14 ml of 1×PBS (300 mM NaCl, pH6.5) was added to the reservoir and the process repeated. Repeat an additional 2 times to ensure urea concentration is sufficiently low. Recover protein sample and measure concentration via OD280.

Polyacrylamide (PAGE) Gel Electrophoresis was carried out on T$_O$, T$_{FINAL}$ using the Invitrogen Novex NuPAGE system as per manufacturer's recommendations.

Western Blot was performed using an Invitrogen iBlot™ Gel Transfer System as per manufacturer's recommendations. Post transfer membrane was blocked using 5% skim milk TBS-T for 1 hour at room temperature. Blocking reagent was discarded and primary antibody (LM-1opt scFv, a single chain Fv variant of LM-1 with a FLAG and His tags at the C-terminus) was added at a ratio of 1:500 in 5% skim milk TBS-T (5 ml total volume) and incubated for 1 hour at room temperature (rocking). Primary antibody was then discarded and the membrane washed with 3× changes of 5 ml TBS-T at 5 minute intervals. Secondary antibody (anti-FLAG HRP conjugate) was added at a ratio of 1:1000 in 5% skim milk TBS-T and incubated for a further hour (rocking). The membrane was again washed with 3× changes of 5 ml TBS-T at 5 minute intervals and for an additional 5 minutes with TBS. Detection was via Metal Enhanced DAB Substrate colorimetric detection (Thermo Scientific).

Mass Spec Analysis of In-gel Digestion of Silver Stained Proteins was then performed. In brief, the gel band of interest from the purified nmt55 gel (FIG. 16B) was excised and placed in a 1.5 ml microfuge tube (Eppendorf) and washed twice with 300 μl of Milli Q quality water for approx 15 minutes. The gel plug was then washed 2 times with 50 μl of 50% acetonitrile/50 mM ammonium bicarbonate (pH8.0) to remove all stain from gel plug. Each wash was approximately 30 minutes in length.

The gel plug was then dehydrated with 100 μl of acetonitrile until it turned opaque, and then the liquid was decanted and the plug dried in vacuum centrifuge. The plug was then rehydrated and incubated in 10 mM dithiothreitol (DTT) in 25 mM ammonium bicarbonate at 56° C. for 1 hour, then allowed to cool to room temperature. An equal volume of 55 mM iodoacetamide in 25 mM ammonium bicarbonate was then added to the sample and incubated in the dark for 45 minutes. Following this the DTT/iodoacetamide solution was decanted and the sample washed with 25 mM ammonium bicarbonate solution for 10 minutes followed by a 10 minute dehydration with 100% acetonitrile. Again the sample was rehydrated with 25 mM ammonium bicarbonate solution for 15 minutes. This liquid was then decanted and replaced with 100% acetonitrile for 10 minutes. The liquid then decanted and the plug dried via vacuum centrifuge.

Sequence grade, modified porcine Trypsin (Promega) solution was prepared fresh by dissolving 20 to 25 µg in 200 µl mM HCl or 1% Acetic acid so that final concentration is between 100 ng/µl to 125 ng/µL. Working trypsin was made by diluting stock solution 1:10 with 25 mM ammonium bicarbonate such that final concentration=10 to 12.5 ng/µl.

Following vacuum centrifuge the dried plug was rehydrated in 20 µl of working trypsin solution for 20 minutes. Excess trypsin solution was removed with a pipette and the sample digested at 37° C. for 4 hrs. The digest was stopped by the additional of 25 µl of 10% formic acid and allowed to stand for 15 minutes. Supernatant was recovered and the gel plug was further extracted with 15 µl of 50% acetonitrile/50 mM ammonium bicarbonate for 15 minutes to recover additional peptides and pooled with initial supernatant, at this point the plug was discarded. The sample was then concentrated to 5 µl in a vacuum centrifuge and loaded directly onto an LC-MSD-ToF Mass Spectrometer for analysis.

FIG. 16A shows PAGE analysis of nmt55 expression. Gel was stained using Invitrogen SimplyBlue SafeStain. Lane 1) Novex Sharp molecular weight pre-stained protein marker. Lane 2) $T_0$ sample showing baseline level of protein expression. Lane 3) $T_{FINAL}$ showing level of nmt55 expression post heat induction at 42°.

FIG. 16B shows PAGE analysis of nmt55 following Profinia™ purification. Gel was stained using Invitrogen SimplyBlue SafeStain. Lane 1) Novex Sharp molecular weight pre-stained protein marker. Lane 2) Purified and concentrated nmt55 from periplasmic expression in E coli. Although the predicted MW of NMT55 is 55 KDa, a protein band of about 30 KDa was observed suggesting a cleavage product.

FIG. 16C shows Western blot of nmt55 following Profinia™ purification. Lane 1) Novex Sharp molecular weight pre-stained protein marker. Lane 2) Purified and concentrated nmt55 detected using LM-1opt scFv as primary antibody with an anti-FLAG monoclonal antibody conjugated with horse-radish peroxidase (HRP) as secondary antibody. A protein band of about 30 KDa was detected by the LM-1opt scFv.

The faint 30 KDa protein band from the Coomassie stained gel (FIG. 16B) was cut out and treated for mass spectral analysis as described. From the mass spectra and computer database search, several hits were identified.

SLYD_ECOLI
FKBP-type peptidyl-prolyl cis-trans isomerase slyD

OS = Escherichia coli

NONO_HUMAN
Non-POU domain-containing octamer-binding protein

OS = Homo sapiens

DEOD_ECOHS
Purine nucleoside phosphorylase deoD-type

OS = Escherichia coli

DEOD2_VIBCH
Purine nucleoside phosphorylase deoD-type 2

OS = Vibrio cholerae

DEOD_SALCH
Purine nucleoside phosphorylase deoD-type

OS = Salmonella choleraesuis

Probability Based Mowse Score was performed on the protein hits. Ions score is −10*Log(P), where P is the probability that the observed match is a random event.

Individual ions scores >51 indicate identity or extensive homology (p<0.05). Protein scores are derived from ions scores as a non-probabilistic basis for ranking protein hits.

The sequence coverage for nmt55 was 11%. The corresponding peptides (bold, underlined) of NONO identified from the mass spectrometer and database search correspond to peptide sequences in the N-terminal region of the recombinant NMT55. Thus the epitope to which LM-1 binds is present at least in the N-terminal 30 KDa domain, or from amino acids 1-300 of NONO/nmt55.

(SEQ ID NO: 16)

```
  1 MQSNKTFNLE KQNHTPRKHH QHHHQQQHHQ QQQQQPPPPP IPANGQQASS

51 QNEGLTIDLK NFRKPGEKTF TQRSRLFVGN LPPDITEEEM RKLFEKYGKA

101 GEVFIHKDKG FGFIRLETRT LAEIAKVELD NMPLRGKQLR VRFACHSASL

151 TVRNLPQYVS NELLEEAFSV FGQVERAVVI VDDRGRPSGK GIVEFSGKPA

201 ARKALDRCSE GSFLLTTFPR PVTVEPMDQL DDEEGLPEKL VIKNQQFHKE

251 REQPPRFAQP GSFEYEYAMR WKALIEMEKQ QQDQVDRNIK EAREKLEMEM

301 EAARHEHQVM LMRQDLMRRQ EELRRMEELH NQEVQKRKQL ELRQEEERRR

351 REEEMRRQQE EMMRRQQEGF KGTFPDAREQ EIRMGQMAMG GAMGINNRGA

401 MPPAPVPAGT PAPPGPATMM PDGTLGLTPP TTERFGQAAT MEGIGAIGGT

451 PPAFNRAAPG AEFAPNKRRR Y
```

What is claimed is:

1. A method of treating a metastasis of colon cancer in a subject, the method comprising:
administering to the subject an unconjugated antibody, or functional fragment thereof, which competes for binding to NONO-nmt55 with LM-1 antibody produced by a cell line DSMZ Deposit No. DSM ACC 2623, wherein the unconjugated antibody, or functional fragment thereof, comprises a heavy chain variable region comprising the three complementarity determining regions (CDRs) of the amino acid sequence shown in SEQ ID NO: 1, and a light chain variable region comprising the three CDRs of the amino acid sequence shown in SEQ ID NO: 11;
wherein said administering is effective to treat the metastasis of colon cancer in the subject.

2. The method of claim 1, wherein the unconjugated antibody, or functional fragment thereof, binds to Colo-699 (DSMZ accession number ACC 196), lung adenocarinoma cell line DV-90 (DSMZ accession number ACC 307), epidermoid lung carcinoma cell line EPLC-272H (DSMZ accession number ACC 383), or lung squamous cell carcinoma cell line LOU-NH91 (DSMZ accession number ACC 393) cells.

3. The method of claim 1, wherein the heavy chain variable region of the unconjugated antibody comprises a sequence which is at least 90% identical to the heavy chain variable region of LM-1 antibody produced by a cell line deposited as DSMZ Deposit No. DSM ACC 2623, and the light chain variable region of the unconjugated antibody comprises a sequence which is at least 90% identical to the light chain variable region of LM-1 antibody produced by a cell line deposited as DSMZ Deposit No. DSM ACC 2623.

4. The method of claim 1, wherein the unconjugated antibody, or functional fragment thereof, is an unconjugated antibody comprising a heavy chain variable region comprising the three complementarity determining regions (CDRs) of the amino acid sequence shown in SEQ ID NO: 1 and a light chain variable region comprising the three CDRs of the amino acid sequence shown in SEQ ID NO: 11.

* * * * *

SEQUENCE LISTING

<160> NUMBER OF SEQ ID NOS: 30

<210> SEQ ID NO 1
<211> LENGTH: 129
<212> TYPE: PRT
<213> ORGANISM: Homo sapiens

<400> SEQUENCE: 1

Gln Val Gln Leu Gln Glu Ser Gly Pro Gly Leu Val Lys Pro Ser Pro
1               5                   10                  15

Thr Leu Ser Leu Thr Cys Ala Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Asp Ala Arg Tyr Asp Tyr Val Trp Gly Ser Tyr Arg
            100                 105                 110

Tyr Asp Ala Phe Asp Ile Trp Gly Gln Gly Thr Met Val Thr Val Ser
        115                 120                 125

Ser

<210> SEQ ID NO 2
<211> LENGTH: 342
<212> TYPE: DNA
<213> ORGANISM: Homo sapiens

<400> SEQUENCE: 2
ccgaccctgt ccctcacctg cgctgtctct ggtggctcca tcagcagtgg tggttactac      60
tggagctgga tccgccagca cccagggaag ggcctgagt ggattgggta catctattac      120
agtgggagca cctactacaa cccgtccctc aagagtcgag ttaccatatc agtagacacg     180
tctaagaacc agttctccct gaagctgagc tctgtgactg ccgcggacac ggccgtgtat     240
tactgtgcga gagttgatgc gcgatatgat tacgtttggg ggagttatcg ttatgatgct    300
tttgatatct ggggccaagg aaccctggtc accgtctctt ca                        342

<210> SEQ ID NO 3
<211> LENGTH: 129
<212> TYPE: PRT
<213> ORGANISM: Homo sapiens

<400> SEQUENCE: 3

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
                85                  90                  95

Cys Ala Arg Val Asp Ala Arg Tyr Asp Tyr Val Trp Gly Ser Tyr Arg
            100                 105                 110

Tyr Asp Ala Phe Asp Ile Trp Gly Gln Gly Thr Met Val Thr Val Ser
        115                 120                 125

Ser

<210> SEQ ID NO 4
<211> LENGTH: 387
<212> TYPE: DNA
<213> ORGANISM: Homo sapiens

<400> SEQUENCE: 4
caggtgcagc tgcaggagtc gggcccagga ctggtgaagc cttcacagac cctgtccctc      60
acctgcgctg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagtt     300
gatgcgcgat atgattacgt ttgggggagt tatcgttatg atgctttga tatctggggc      360 caagggacaa tggtcaccgt ctcttca                                         387

<210> SEQ ID NO 5
<211> LENGTH: 129
<212> TYPE: PRT
<213> ORGANISM: Homo sapiens

<400> SEQUENCE: 5

Gln Val Gln Leu Gln Glu Ser Gly Pro Gly Leu Val Lys Pro Ser Pro
1               5                   10                  15

Thr Leu Ser Leu Thr Cys Ala Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Asp Ala Arg Tyr Asp Tyr Val Trp Gly Ser Tyr Arg
            100                 105                 110

Phe Asp Ala Phe Asp Ile Trp Gly Gln Gly Thr Met Val Thr Val Ser
        115                 120                 125

Ser

<210> SEQ ID NO 6
<211> LENGTH: 387
<212> TYPE: DNA
<213> ORGANISM: Homo sapiens

<400> SEQUENCE: 6
caggtgcagc tgcaggagtc gggcccagga ctggtgaagc cttcaccgac cctgtccctc      60
acctgcgctg tctctggtgg ctccatcagc agtggtggtt actactggag ctggatccgc     120
```

-continued

```
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagtt    300
gatgcgcgat atgattacgt ttggggagt tatcgttttg atgcttttga tatctggggc     360
caagggacaa tggtcaccgt ctcttca                                         387
```

<210> SEQ ID NO 7
<211> LENGTH: 129
<212> TYPE: PRT
<213> ORGANISM: Homo sapiens

<400> SEQUENCE: 7

```
Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Asp Ala Arg Tyr Asp Tyr Val Trp Gly Ser Tyr Arg
            100                 105                 110

Tyr Asp Ala Phe Asp Ile Trp Gly Gln Gly Thr Met Val Thr Val Ser
        115                 120                 125

Ser
```

<210> SEQ ID NO 8
<211> LENGTH: 387
<212> TYPE: DNA
<213> ORGANISM: Homo sapiens

<400> SEQUENCE: 8

```
cagctgcagc tgcaggagtc gggcccagga ctggtgaagc cttcacagac cctgtccctc    60
acctgcactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagtt    300
gatgcgcgat atgattacgt ttggggagt tatcgttatg atgcttttga tatctggggc     360
caagggacaa tggtcaccgt ctcttca                                         387
```

<210> SEQ ID NO 9
<211> LENGTH: 130
<212> TYPE: PRT
<213> ORGANISM: Homo sapiens

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Ile Ser Ser Gly
            20                  25                  30
```

Gly Tyr Tyr Trp Ser Trp Ile Arg Gln Ala Pro Gly Lys Gly Leu Glu
            35                  40                  45

Trp Val Ile Gly Tyr Ile Tyr Tyr Ser Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Val Asp Ala Arg Tyr Asp Tyr Val Trp Gly Ser Tyr
                100                 105                 110

Arg Tyr Asp Ala Phe Asp Ile Trp Gly Gln Gly Thr Leu Val Thr Val
            115                 120                 125

Ser Ser
    130

<210> SEQ ID NO 10
<211> LENGTH: 390
<212> TYPE: DNA
<213> ORGANISM: Homo sapiens

<400> SEQUENCE: 10
gaggtgcagc tggtcgagag cgggggaggc ctggtgcagc caggggggatc tctgagactg    60 agctgcgccg tgagcggcgg atctatttcc agcgggggat attattggtc ttggatcaga   120
caggctcccg gaaagggggct ggaatgggtc atcggctaca tctactacag cggcagcacc   180
tactacgccg acagcgtgaa gggccggttc accatcagcc gggacaacag caagaacacc   240
ctgtacctgc agatgaacag cctgcggggcc gaggacaccg cggtgtacta ctgcgccaga   300
gtggacgcca gatacgacta cgtgtgggggc agctacagat acgacgcctt cgacatctgg   360
ggccagggca ccctggtgac cgtgtcttct                                     390

<210> SEQ ID NO 11
<211> LENGTH: 113
<212> TYPE: PRT
<213> ORGANISM: Homo sapiens

<400> SEQUENCE: 11

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Trp Val Phe Gly Gly Gly Thr Lys Leu Thr Val Leu Gly
                100                 105                 110

Gln

<210> SEQ ID NO 12
<211> LENGTH: 339
<212> TYPE: DNA

<213> ORGANISM: Homo sapiens

<400> SEQUENCE: 12

```
cagtctgtgt tgacgcagcc gccctcagtg tctgcggccc caggacagaa ggtcaccatc      60
tcctgctctg gaagcagctc caacattggg aataattatg tatcctggta ccagcagctc    120
ccaggaacag cccccaaact cctcatttat gacaataata gcgaccctca gggattcct     180
gaccgattct ctggctccaa gtctggcacg tcagccaccc tgggcatcac cggactccag    240
actggggacg aggccgatta ttactgcgga acatgggata gcagcctgag tgctggttgg    300
gtgttcggcg gagggaccaa gctgaccgtc ctaggtcag                           339
```

<210> SEQ ID NO 13
<211> LENGTH: 115
<212> TYPE: PRT
<213> ORGANISM: Homo sapiens

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Arg Ser Gly Ser Ser Asn Ile Gly
            20                  25                  30

Asn Asn Tyr Val Ser Trp Tyr Gln Gln Lys Pro Gly Lys Ala Pro Lys
        35                  40                  45

Leu Leu Ile Tyr Asp Asn Asn Lys Glu Pro Ser Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gly Thr Trp Asp
                85                  90                  95

Ser Ser Leu Ser Ala Gly Trp Val Phe Gly Gln Gly Thr Lys Val Glu
            100                 105                 110

Ile Lys Arg
        115
```

<210> SEQ ID NO 14
<211> LENGTH: 345
<212> TYPE: DNA
<213> ORGANISM: Homo sapiens

<400> SEQUENCE: 14

```
gacatccaga tgacccagag ccccagcagc ctgagcgcca gcgtgggcga cagagtgacc      60
atcacctgca gaagcggcag cagcagcaac atcggcaaca attatgtctc ttggtatcag    120
cagaaacctg gcaaggcccc caagctgctg atctacgaca caacaaaga acccagcggc    180
gtgcccagcc ggtttagcgg cagcggctcc ggcaccgact tcaccctgac catcagcagc    240
ctgcagcccg aggatttcgc cacctactac tgtcagggga catgggatag cagcctgtcc    300
gccggctggg tgttcggcca gggaacaaag gtggagatca agaga                    345
```

<210> SEQ ID NO 15
<211> LENGTH: 241
<212> TYPE: PRT
<213> ORGANISM: Homo sapiens

<400> SEQUENCE: 15

```
Met Ala Cys Pro Gly Phe Leu Trp Ala Leu Val Ile Ser Thr Cys Leu
1               5                   10                  15
```

Glu Phe Ser Met Ala Ser Trp Ala Gln Ser Val Leu Thr Gln Pro Pro
            20                  25                  30

Ser Val Ser Ala Ala Pro Gly Gln Lys Val Thr Ile Ser Cys Ser Gly
        35                  40                  45

Ser Ser Ser Asn Ile Gly Asn Asn Tyr Val Ser Trp Tyr Gln Gln Leu
    50                  55                  60

Pro Gly Thr Ala Pro Lys Leu Leu Ile Tyr Asp Asn Asn Lys Arg Pro
65                  70                  75                  80

Ser Gly Ile Pro Asp Arg Phe Ser Gly Ser Lys Ser Gly Thr Ser Ala
                85                  90                  95

Thr Leu Gly Ile Thr Gly Leu Gln Thr Gly Asp Glu Ala Asp Tyr Tyr
            100                 105                 110

Cys Gly Thr Trp Asp Ser Ser Leu Ser Ala Gly Trp Val Phe Gly Gly
        115                 120                 125

Gly Thr Lys Leu Thr Val Leu Gly Gln Pro Lys Ala Ala Pro Ser Val
    130                 135                 140

Thr Leu Phe Pro Pro Ser Ser Glu Glu Leu Gln Ala Asn Lys Ala Thr
145                 150                 155                 160

Leu Val Cys Leu Ile Ser Asp Phe Tyr Pro Gly Ala Val Thr Val Ala
                165                 170                 175

Trp Lys Ala Asp Ser Ser Pro Val Lys Ala Gly Val Glu Thr Thr Thr
            180                 185                 190

Pro Ser Lys Gln Ser Asn Asn Lys Tyr Ala Ala Ser Ser Tyr Leu Ser
        195                 200                 205

Leu Thr Pro Glu Gln Trp Lys Ser His Lys Ser Tyr Ser Cys Gln Val
    210                 215                 220

Thr His Glu Gly Ser Thr Val Glu Lys Thr Val Ala Pro Thr Glu Cys
225                 230                 235                 240

Ser

<210> SEQ ID NO 16
<211> LENGTH: 471
<212> TYPE: PRT
<213> ORGANISM: Homo sapiens

<400> SEQUENCE: 16

Met Gln Ser Asn Lys Thr Phe Asn Leu Glu Lys Gln Asn His Thr Pro
1               5                   10                  15

Arg Lys His His Gln His His Gln Gln His His Gln Gln Gln
            20                  25                  30

Gln Gln Gln Pro Pro Pro Pro Ile Pro Ala Asn Gly Gln Gln Ala
        35                  40                  45

Ser Ser Gln Asn Glu Gly Leu Thr Ile Asp Leu Lys Asn Phe Arg Lys
    50                  55                  60

Pro Gly Glu Lys Thr Phe Thr Gln Arg Ser Arg Leu Phe Val Gly Asn
65                  70                  75                  80

Leu Pro Pro Asp Ile Thr Glu Glu Glu Met Arg Lys Leu Phe Glu Lys
                85                  90                  95

Tyr Gly Lys Ala Gly Glu Val Phe Ile His Lys Asp Lys Gly Phe Gly
            100                 105                 110

Phe Ile Arg Leu Glu Thr Arg Thr Leu Ala Glu Ile Ala Lys Val Glu
        115                 120                 125

Leu Asp Asn Met Pro Leu Arg Gly Lys Gln Leu Arg Val Arg Phe Ala
    130                 135                 140

```
Cys His Ser Ala Ser Leu Thr Val Arg Asn Leu Pro Gln Tyr Val Ser
145                 150                 155                 160

Asn Glu Leu Leu Glu Glu Ala Phe Ser Val Phe Gly Gln Val Glu Arg
                165                 170                 175

Ala Val Val Ile Val Asp Asp Arg Gly Arg Pro Ser Gly Lys Gly Ile
            180                 185                 190

Val Glu Phe Ser Gly Lys Pro Ala Ala Arg Lys Ala Leu Asp Arg Cys
        195                 200                 205

Ser Glu Gly Ser Phe Leu Leu Thr Thr Phe Pro Arg Pro Val Thr Val
    210                 215                 220

Glu Pro Met Asp Gln Leu Asp Asp Glu Glu Gly Leu Pro Glu Lys Leu
225                 230                 235                 240

Val Ile Lys Asn Gln Gln Phe His Lys Glu Arg Glu Gln Pro Pro Arg
                245                 250                 255

Phe Ala Gln Pro Gly Ser Phe Glu Tyr Glu Tyr Ala Met Arg Trp Lys
                260                 265                 270

Ala Leu Ile Glu Met Glu Lys Gln Gln Asp Gln Val Asp Arg Asn
                275                 280                 285

Ile Lys Glu Ala Arg Glu Lys Leu Glu Met Glu Met Glu Ala Ala Arg
290                 295                 300

His Glu His Gln Val Met Leu Met Arg Gln Asp Leu Met Arg Arg Gln
305                 310                 315                 320

Glu Glu Leu Arg Arg Met Glu Glu Leu His Asn Gln Glu Val Gln Lys
                325                 330                 335

Arg Lys Gln Leu Glu Leu Arg Gln Glu Glu Arg Arg Arg Arg Glu
                340                 345                 350

Glu Glu Met Arg Arg Gln Gln Glu Glu Met Met Arg Arg Gln Gln Glu
                355                 360                 365

Gly Phe Lys Gly Thr Phe Pro Asp Ala Arg Glu Gln Glu Ile Arg Met
                370                 375                 380

Gly Gln Met Ala Met Gly Gly Ala Met Gly Ile Asn Asn Arg Gly Ala
385                 390                 395                 400

Met Pro Pro Ala Pro Val Pro Ala Gly Thr Pro Ala Pro Pro Gly Pro
                405                 410                 415

Ala Thr Met Met Pro Asp Gly Thr Leu Gly Leu Thr Pro Thr Thr
                420                 425                 430

Glu Arg Phe Gly Gln Ala Ala Thr Met Glu Gly Ile Gly Ala Ile Gly
                435                 440                 445

Gly Thr Pro Pro Ala Phe Asn Arg Ala Ala Pro Gly Ala Glu Phe Ala
        450                 455                 460

Pro Asn Lys Arg Arg Arg Tyr
465                 470

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 17
agatctgccg ccaccatggc atgccctggc ttc                           33

<210> SEQ ID NO 18
<211> LENGTH: 24
<212> TYPE: DNA
```

```
<213> ORGANISM: Artificial Sequence
<220> FEATURE:
<223> OTHER INFORMATION: Description of Artificial Sequence: Primer

<400> SEQUENCE: 18
tgaagagacg gtgaccattg tccc                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
agcaccaagg gcccatcggt cttc                                              24

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
ctcgagtcat ttacccggag acagggagag                                        30

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
gatatctccg ccaccatggc atgccctggc ttc                                    33

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
gtcgacctat gaacattctg taggggccac                                        30

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
atgcagagta ataaaacttt taac                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 24
gtatcggcga cgtttgtttg gggc                                              24
```

-continued

```
<210> SEQ ID NO 25
<211> LENGTH: 12
<212> TYPE: PRT
<213> ORGANISM: Homo sapiens

<400> SEQUENCE: 25

Val Ser Gly Gly Ser Ile Ser Ser Gly Gly Tyr Tyr
1               5                   10

<210> SEQ ID NO 26
<211> LENGTH: 16
<212> TYPE: PRT
<213> ORGANISM: Homo sapiens

<400> SEQUENCE: 26

Tyr Ile Tyr Tyr Ser Gly Ser Thr Tyr Tyr Asn Pro Ser Leu Lys Ser
1               5                   10                  15

<210> SEQ ID NO 27
<211> LENGTH: 19
<212> TYPE: PRT
<213> ORGANISM: Homo sapiens

<400> SEQUENCE: 27

Val Asp Ala Arg Tyr Asp Tyr Val Trp Gly Ser Tyr Arg Tyr Asp Ala
1               5                   10                  15

Phe Asp Ile

<210> SEQ ID NO 28
<211> LENGTH: 13
<212> TYPE: PRT
<213> ORGANISM: Homo sapiens

<400> SEQUENCE: 28

Ser Gly Ser Ser Ser Asn Ile Gly Asn Asn Tyr Val Ser
1               5                   10

<210> SEQ ID NO 29
<211> LENGTH: 8
<212> TYPE: PRT
<213> ORGANISM: Homo sapiens

<400> SEQUENCE: 29

Asp Asn Asn Lys Arg Pro Ser Gly
1               5

<210> SEQ ID NO 30
<211> LENGTH: 12
<212> TYPE: PRT
<213> ORGANISM: Homo sapiens

<400> SEQUENCE: 30

Gly Thr Trp Asp Ser Ser Leu Ser Ala Gly Trp Val
1               5                   10
```